United States Patent
Isaksen et al.

(10) Patent No.: US 11,931,385 B2
(45) Date of Patent: *Mar. 19, 2024

(54) FEED ADDITIVE COMPOSITION

(71) Applicant: DUPONT NUTRITION BIOSCIENCES APS, Copenhagen K (DK)

(72) Inventors: Mai Faurschou Isaksen, Hojbjerg (DK); Marion Bernardeau, Caen (FR); Luis Fernando Romero Millan, Wilshire (GB); Elijah G. Kiarie, Guelph (CA); Susan Lund Arent, Brabrand (DK); Päivi Nurminen, Siuntio (FI); Sofia Forssten, Kantvik (FI); Daniel Petri, Waukesha, WI (US); Elizabeth Ann Galbraith, Wauwatosa, WI (US); Mari Ellen Davis, Waukesha, WI (US)

(73) Assignee: DUPONT NUTRITION BIOSCIENCES APS, Kongens Lyngby (DK)

( * ) Notice: Subject to any disclaimer, the term of this patent is extended or adjusted under 35 U.S.C. 154(b) by 57 days.

This patent is subject to a terminal disclaimer.

(21) Appl. No.: 17/368,282

(22) Filed: Jul. 6, 2021

(65) Prior Publication Data

US 2022/0040241 A1 Feb. 10, 2022

Related U.S. Application Data

(60) Continuation of application No. 16/149,708, filed on Oct. 2, 2018, now abandoned, which is a division of application No. 14/609,911, filed as application No. PCT/EP2013/066254 on Aug. 2, 2013, now abandoned.

(60) Provisional application No. 61/679,084, filed on Aug. 3, 2012.

(51) Int. Cl.
| | |
|---|---|
| A61K 35/742 | (2015.01) |
| A23K 10/16 | (2016.01) |
| A23K 10/18 | (2016.01) |
| A23K 20/189 | (2016.01) |
| A23K 50/30 | (2016.01) |
| A23K 50/60 | (2016.01) |
| A23K 50/75 | (2016.01) |
| A61K 35/747 | (2015.01) |
| A61K 38/47 | (2006.01) |

(52) U.S. Cl.
CPC ............ *A61K 35/742* (2013.01); *A23K 10/16* (2016.05); *A23K 10/18* (2016.05); *A23K 20/189* (2016.05); *A23K 50/30* (2016.05); *A23K 50/60* (2016.05); *A23K 50/75* (2016.05); *A61K 35/747* (2013.01); *A61K 38/47* (2013.01); *A23V 2400/11* (2023.08); *C12Y 302/01008* (2013.01); *C12Y 302/01021* (2013.01)

(58) Field of Classification Search
None
See application file for complete search history.

(56) References Cited

PUBLICATIONS

Lin et al. "Hydrolytic enzyme of cellulose for complex formulation applied research", Applied Biochemistry and Biotechnology, vol. 164, pp. 23-33 (Year: 2011).*

* cited by examiner

*Primary Examiner* — Michelle F. Paguio Frising

(57) ABSTRACT

A feed additive composition comprising a direct fed microbial (DFM), in combination with a xylanase (e.g. endo-1,4-β-d-xylanase) and a β-glucanase (and optionally a further fibre degrading enzyme).

8 Claims, 1 Drawing Sheet
Specification includes a Sequence Listing.

FEED ADDITIVE COMPOSITION

CROSS-REFERENCE TO RELATED APPLICATIONS

The present application is a continuation of U.S. patent application Ser. No. 16/149,708, filed Oct. 2, 2018, which is a divisional of U.S. patent application Ser. No. 14/609,911, filed Jan. 30, 2015, which is a 371 of International Patent Application No. PCT/EP2013/066254, filed Aug. 2, 2013, which claims priority to U.S. Provisional Patent Application No. 61/679,084, which was filed on Aug. 3, 2012, and all of which are herein incorporated by reference.

REFERENCE TO A SEQUENCE LISTING

The contents of the electronic submission of the text file Sequence Listing, named 20210706_NB31601USPCN_SequenceListing.txt; was created on Jul. 6, 2021 and is 30,125 bytes in size, which is hereby incorporated by reference in its entirety.

FIELD OF INVENTION

The present invention relates to methods for improving feed compositions using a specific direct fed microbial in combination with a xylanase and a ß-glucanase, and to a feed additive composition comprising a direct fed microbial in combination with a xylanase and a β-glucanase. The present invention further relates to uses and kits.

BACKGROUND OF THE INVENTION

Supplemental enzymes are used as additives to animal feed, particularly poultry and swine feeds, as a means to improve nutrient utilization and production performance characteristics. Enzyme blends are available to improve the nutritional value of diets containing cereal grains, soybean meal, animal protein meals, or high fibre food and industrial by-products.

The concept of direct fed microbials (DFM) involves the feeding of live beneficial microbes to animals like chickens or pigs, such that when administered in adequate amounts confer a health benefit on the host. Probiotics is another term for this category of feed additives. Probiotics or DFM have been shown to improve animal performance in controlled studies. DFM includes direct fed bacteria and or yeast-based products.

Although combinations of DFMs with some enzymes have been contemplated, the interaction between DFMs and enzymes has never been fully understood. The present invention relates to novel specific combinations which surprisingly significantly improve production performance characteristics of animals.

Continued pressure on global feed grain markets has resulted in trends for the swine and poultry industries to seek alternative cost-effective ingredient options such as co-products (by-products) from the biofuel and milling industries. However, a characteristic of alternative ingredients is the high content of non-starch polysaccharides (NSP; fibre) which for the non-ruminants, are of low nutritive value as they are indigestible, limit the nutrient intake of an animal and negatively influence energy and nutrient utilization. It follows that successful application of alternative fibrous ingredients in monogastric diets will be dependent on the availability of technologies for efficiently utilizing the energy contained in the dietary fibre, mitigating risks associated with their anti-nutritional properties and potential economic benefits when formulated correctly into diets.

SUMMARY OF INVENTION

A seminal finding of the present invention is that the degradation of dietary material derived from plant cell wall particles which is high in non-starch polysaccharides (NSP) by xylanases can be optimized for improved animal performance when combining xylanase and a β-glucanase with one or more specific direct fed-microbials (DFMs) selected for their capacity to digest plant cell wall structural carbohydrates and/or their capacity of producing Short Chain Fatty Acids (SCFA) from pentoses (e.g. arabinoxylans) contained in the NSP fraction of ingredients in anaerobic conditions.

The reason why this combination improves performance is that the solubilisation of fibre, specifically hemicellulose, from the diet is maximized in the gastro intestinal tract (GIT) of the animals. This solubilisation of hemicellulose would not always be sufficient to increase performance because C5-sugars released are not an efficient source of energy for animals when they are absorbed (Savory C., J. Br. J. Nut. 1992, 67: 103-114), but they are a more efficient source of energy when converted into short chain fatty acids (SCFA) either by microorganisms in the GIT or by DFMs.

Therefore the energy value from plant products (e.g. wheat, corn, oats, barley and cereals co-products (by-products) or mixed grain diet readily accessible for monogastrics) can be optimized by combining xylanase and a β-glucanase and specific DFMs that can either produce SCFAs from NSP fraction pentoses in anaerobic conditions or that can modulate the microbial populations in the GIT to increase SCFA production from the sugars released. The DFMs may adapt their metabolism to synergistically increase the fibre hydrolysis in combination with xylanase and β-glucanase. Using DFMs with fibrolytic enzymes can provide additional benefits and maximize the benefits of the carbohydrases.

Specific DFMs selected for their enzymatic activities can be considered as a glycan-driven bacterial food chain. The specifically selected DFMs taught herein may preferentially utilize dietary fibres, a trait that allows them to carry out the initial glycan digestion steps to liberate shorter, more soluble polysaccharides for other bacteria, e.g. other endogenous GIT microflora. The specific DFMs have been selected for their metabolism which adjusts according to the glycans released by enzymes (e.g. xylanase and β-glucanase) to improve the efficacy of the enzymes taught herein and the DFM(s) combination compared to use of a combination of enzymes alone or the use of DFM(s) alone.

Without wishing to be bound by theory, in the present invention dietary material derived from plant cell wall particles which is rich in source-specific glycans, such as cellulose, hemicellulose and pectin (plant material) or glycosaminoglycans enter the distal gut in particulate forms that are attacked by the specific DFMs glycan degraders which are capable of directly binding to these insoluble particles and digesting their glycan components. After this initial degradation of glycan-containing particles, more-soluble glycan fragments can be digested by secondary glycan degraders present in the caecum, which contribute to the liberated pool of short-chain fatty acid (SOFA) fermentation products that is derived from both types of degraders. As SCFAs arise from carbohydrate fermentation and/or protein fermentation and deamination by the indigenous anaerobic microflora in the GIT, SOFA concentration can be an index of the anaerobic-organism population. SOFA may actually provide a number of benefits to the host animal, acting as metabolic fuel for intestine, muscle, kidney, heart, liver and brain tissue, and also affording bacteriostatic and bacteriocidal properties against organisms such as *Salmonella* and *E. coli*.

The nutritional value of fibre in non-ruminants can mainly be derived through short chain fatty acids (SOFA) production via fermentation of solubilized or degraded fibres by effective fibre degrading enzymes (e.g. a xylanase and a β-glucanase, suitably in combination with a further fibre degrading enzyme). Feed xylanase alone is not enough to use fibrous ingredients in animal (especially non-ruminant) diets. A large array of chemical characteristics exists among plant-based feed ingredients. An enzyme application depends on the characteristics of the plant (feed) material. By way of example only, in wheat grain arabinoxylans predominates, however in wheat middlings (a co-product or by-product of wheat milling), the content of β-glucan increases from $8\ g^{-1}$ DM (in grain) to an excess of $26\ g\ kg^{-1}$ DM.

SCFAs have different energy values and some can serve as precursors of glucose and some can contribute to the maintenance of intestinal integrity and health. The inventors have found that the specific combinations taught herein preferentially move the fermentation process in an animal's GIT towards the production of more valuable/useful SCFA's such as butyric acid and/or propionic acids.

In one aspect, the present invention provides a feed additive composition comprising a direct fed microbial (DFM), in combination with a xylanase and a β-glucanase, wherein the DFM is selected from the group consisting of an enzyme producing strain; a C5 sugar-fermenting strain; a short-chain fatty acid-producing strain; a fibrolytic, endogenous microflora-promoting strain; or combinations thereof.

The present invention further provides a method for:
i) improving the performance of a subject, or
ii) for improving digestibility of a raw material in a feed (e.g. nutrient digestibility, such as amino acid digestibility), or
iii) for improving nitrogen retention, or
iv) for improving feed conversion ratio (FCR), or
v) for improving weight gain in a subject, or
vi) for improving feed efficiency in a subject, or
vii) for shifting the fermentation process in the subject's gastrointestinal tract towards the production of butyric acid and/or propionic acid,
which method comprising administering to a subject a direct fed microbial (DFM), in combination with a xylanase and a β-glucanase, wherein the DFM is selected from the group consisting of an enzyme producing strain; a C5 sugar-fermenting strain; a short-chain fatty acid-producing strain; a fibrolytic, endogenous microflora-promoting strain; or combinations thereof.

The present invention yet further provides a premix comprising a feed additive composition according to the present invention or a direct fed microbial (DFM), a xylanase and a β-glucanase, wherein the DFM is selected from the group consisting of an enzyme producing strain; a C5 sugar-fermenting strain; a short-chain fatty acid-producing strain; a fibrolytic, endogenous microflora-promoting strain; or combinations thereof, and at least one vitamin and/or at least one mineral.

In a yet further aspect, the present invention provides a feed comprising a feed additive composition according to the present invention or a premix according to the present invention. The present invention yet further provides a feed comprising a direct fed microbial (DFM), in combination with a xylanase and a β-glucanase, wherein the DFM is selected from the group consisting of an enzyme producing strain; a C5 sugar-fermenting strain; a short-chain fatty acid-producing strain; a fibrolytic, endogenous microflora-promoting strain; or combinations thereof.

In another aspect, there is provided a method of preparing a feedstuff comprising admixing a feed component with a feed additive composition according to the present invention or a premix according to the present invention.

A further aspect of the present invention is a method of preparing a feedstuff comprising admixing a feed component with a direct fed microbial (DFM), in combination with a xylanase and a β-glucanase, wherein the DFM is selected from the group consisting of an enzyme producing strain; a C5 sugar-fermenting strain; a short-chain fatty acid-producing strain; a fibrolytic, endogenous microflora-promoting strain; or combinations thereof The present invention yet further provides use of a direct fed microbial (DFM), in combination with a xylanase and a β-glucanase, wherein the DFM is selected from the group consisting of an enzyme producing strain; a C5 sugar-fermenting strain; a short-chain fatty acid-producing strain; a fibrolytic, endogenous microflora-promoting strain; or combinations thereof:
i) for improving the performance of a subject, or
ii) for improving digestibility of a raw material in a feed (e.g. nutrient digestibility, such as amino acid digestibility), or
iii) for improving nitrogen retention), or
iv) for improving feed conversion ratio (FCR), or
v) for improving weight gain in a subject, or
vi) for improving feed efficiency in a subject, or
vii) for shifting the fermentation process in the subject's gastrointestinal tract towards the production of butyric acid and/or propionic acid.

A further aspect relates to a kit comprising a direct fed microbial (DFM), a xylanase and a 3-glucanase, wherein the DFM is selected from the group consisting of an enzyme producing strain; a C5 sugar-fermenting strain; a short-chain fatty acid-producing strain; a fibrolytic, endogenous microflora-promoting strain; or combinations thereof (and optionally at least one vitamin and/or optionally at least one mineral) and instructions for administration.

DETAILED DESCRIPTION OF THE INVENTION

Figure 1A:
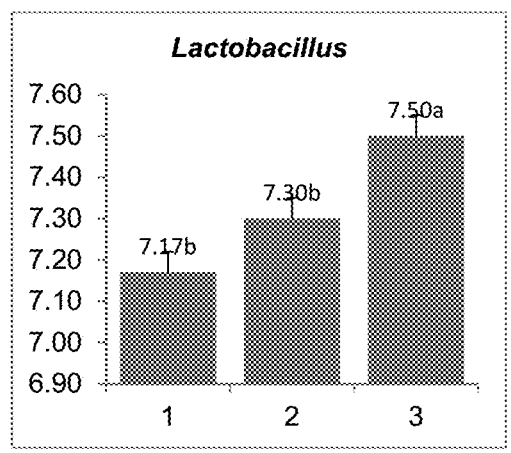
FIG. 1A and FIG. 1B show the effects of xylanase and β-glucanase without or with *Bacillus* direct fed microbial (DFM) on fecal *Lactobacillus* (FIG. 1A) and *E. coli* (FIG. 1B) counts (log transformed colony forming unit/gram of feces, $Log_{10}$ cfu/g).

Preferably the enzyme(s) used in the present invention are exogenous to the DFM. In other words the enzyme(s) are preferably added to or admixed with the DFM.

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

The headings provided herein are not limitations of the various aspects or embodiments of this disclosure which can be had by reference to the specification as a whole. Accordingly, the terms defined immediately below are more fully defined by reference to the specification as a whole.

Amino acids are referred to herein using the name of the amino acid, the three letter abbreviation or the single letter abbreviation.

The term "protein", as used herein, includes proteins, polypeptides, and peptides.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The terms "protein" and "polypeptide" are used interchangeably herein. In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

All E.C. enzyme classifications referred to herein relate to the classifications provided in Enzyme Nomenclature—Recommendations (1992) of the nomenclature committee of the International Union of Biochemistry and Molecular Biology—ISBN 0-12-226164-3.

Other definitions of terms may appear throughout the specification. Before the exemplary embodiments are described in more detail, it is to understand that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "an enzyme" includes a plurality of such candidate agents and reference to "the feed" includes reference to one or more feeds and equivalents thereof known to those skilled in the art, and so forth.

The publications discussed herein are provided solely for their disclosure prior to the filing date of the present application. Nothing herein is to be construed as an admission that such publications constitute prior art to the claims appended hereto.

The enzymes for use in the present invention can be produced either by solid or submerged culture, including batch, fed-batch and continuous-flow processes. Culturing is accomplished in a growth medium comprising an aqueous mineral salts medium, organic growth factors, the carbon and energy source material, molecular oxygen, and, of course, a starting inoculum of one or more particular microorganism species to be employed.

The DFM for use in the present invention may be an enzyme producing strain.

The DFM for use in the present invention may be a C5 sugar-fermenting strain.

The DFM for use in the present invention may be a short-chain fatty acid-producing strain.

The DFM for use in the present invention may be a fibrolytic, endogenous microflora-promoting strain.

The enzyme producing strain and/or the C-5 sugar-fermenting strain and/or the short-chain fatty acid-producing strains and/or the fibrolytic, endogenous microflora-promoting strain according to the present invention may be selected from the group consisting of the following genera: *Bacillus, Enterococcus, Lactobacillus, Propionibacterium* and combinations thereof. The enzyme producing strain and/or the C-5 sugar-fermenting strain and/or the short-chain fatty acid-producing strains and/or the fibrolytic, endogenous microflora-promoting strain according to the present invention may be at least one strain selected from the *Bacillus* genus, particularly *Bacillus subtilis, B. licheniformis, B. amyloliquefaciens* or *B. pumilus*.

The enzyme producing strain and/or the C-5 sugar-fermenting strain and/or the short-chain fatty acid-producing strains and/or the fibrolytic, endogenous microflora-promoting strain according to the present invention may be at least one strain selected from the *Enterococcus* genus, particularly *Enterococcus faecium*.

The enzyme producing strain and/or the C-5 sugar-fermenting strain and/or the short-chain fatty acid-producing strains and/or the fibrolytic, endogenous microflora-promoting strain according to the present invention may be selected from the group consisting of: *Bacillus subtilis* AGTP BS3BP5, *Bacillus subtilis* AGTP BS442, *B. subtilis* AGTP BS521, *B. subtilis* AGTP BS918, *Bacillus subtilis* AGTP BS1013, *B. subtilis* AGTP BS1069, *B. subtilis* AGTP 944, *Bacillus subtilis* BS 2084 (NRRL B-50013), *Bacillus subtilis* LSSAO1 (NRRL B-50104), *Bacillus subtilis* 3A-P4 (PTA-6506), *Bacillus subtilis* 22C-P1 (PTA-6508), *Bacillus licheniformis* BL21 (NRRL B-50134), *Bacillus subtilis* BS-27 (NRRL B-50105), *Bacillus subtilis* BS18 (NRRL B-50633), *Bacillus subtilis* 15A-P4 (PTA-6507), *Bacillus subtilis* BS278 (NRRL B-50634), *Bacillus licheniformis* BL842 (NRRL B-50516), *B. pumilus* AGTP BS 1068, *B. pumilus* KX11-1, *Enterococcus faecium* I D7, *Propionibacterium acidipropionici* P169, *Lactobacillus rhamnosus* CNCM-I-3698, *Lactobacillus farciminis* CNCM-I-3699, or a strain having all the characteristics thereof, any derivative or variant thereof, and combinations thereof.

The enzyme producing strain and/or the C-5 sugar-fermenting strain and/or the short-chain fatty acid-producing strains and/or the fibrolytic, endogenous microflora-promoting strain for use in the present invention is preferably a viable bacterium.

The enzyme producing strain and/or the C-5 sugar-fermenting strain and/or the short-chain fatty acid-producing strains and/or the fibrolytic, endogenous microflora-promoting strain for use in the present invention may be in the form of an endospore.

The xylanase for use in the present invention is preferably an endo-1,4-β-d-xylanase (E.C. 3.2.1.8).

In some embodiments preferably the xylanase and the β-glucanase are used in combination with at least one further fibre degrading enzyme. The (further) fibre degrading enzyme may be selected from the group consisting of a cellobiohydrolase (E.C. 3.2.1.176 and E.C. 3.2.1.91), a β-glucosidase (E.C. 3.2.1.21), a β-xylosidase (E.C. 3.2.1.37), a feruloyl esterase (E.C. 3.1.1.73), an α-arabinofuranosidase (E.C. 3.2.1.55), a pectinase (e.g. an endopolygalacturonase (E.C. 3.2.1.15), an exopolygalacturonase (E.C. 3.2.1.67) or a pectate lyase (E.C. 4.2.2.2)), or combinations thereof.

Suitably there may be more than one further fibre degrading enzyme, suitably more than two, suitably more than three, suitably more than four, suitably more than five.

Suitably the feed additive composition according to the present invention or the composition comprising a DFM in combination with a xylanase, a β-glucanase and at least one further degrading enzyme move the fermentation process in the subject's gastrointestinal tract towards the production of butyric acid and/or propionic acid.

Direct Fed Microbial (DFM)

The term "microbial" herein is used interchangeably with "microorganism".

The DFM for use in the present invention may be any suitable DFM which is an "enzyme producing strain"—such as an enzyme producing *Bacillus* strain. To determine if a DFM is an "enzyme producing strain" the DFM assay defined herein as "enzyme producing DFM assay" may be used. A DFM is considered to be an enzyme producing DFM if it is classed as an enzyme producing DFM using the "enzyme producing DFM assay" taught herein.

The DFM for use in the present invention may be any suitable DFM which is a "C5 sugar-fermenting strain". To determine if a DFM is a "C5 sugar-fermenting strain" the DFM assay defined herein as "C5 sugar-fermenting DFM assay" may be used. A DFM is considered to be a C5 sugar-fermenting DFM if it is classed as C5 sugar fermenting using the "C5 sugar-fermenting DFM assay" taught herein.

The DFM for use in the present invention may be any suitable DFM which is a "short chain fatty acid (SCFA)-producing strain". To determine if a DFM is a "SOFA-producing strain" the DFM assay defined herein as "SOFA-producing DFM assay" may be used. A DFM is considered to be a SOFA-producing DFM if it is classed as SOFA producing using the "SOFA-producing DFM assay" taught herein.

The DFM for use in the in present invention may be any suitable DFM which is a "fibrolytic, endogenous microflora-promoting strain". To determine if a DFM is a "fibrolytic, endogenous microflora-promoting strain" the DFM assay defined herein as " "fibrolytic, endogenous microflora-promoting DFM assay" may be used. A DFM is considered to be a fibrolytic, endogenous microflora-promoting DFM if it promotes or stimulates endogenous fibrolytic microflora using the assay taught herein.

The DFM for use in the present invention may be any suitable DFM which is an "enzyme producing strain", a "C5 sugar-fermenting strain", a "SOFA-producing strain", a "fibrolytic, endogenous microflora-promoting strain" or combinations thereof.

Suitably the DFM for use in the present invention may be a DFM which is a strain that would be classified as being an "enzyme producing strain" and/or a "C5 sugar-fermenting strain" and/or a "SOFA-producing strain" and/or a "fibrolytic, endogenous microflora-promoting strain". Suitably the DFM may be a strain that is classified as having more than one type of activity, e.g. at least 2, suitably at least 3, suitably all 4 activities, e.g. enzyme producing activity, C5 sugar-fermenting activity, SOFA-producing activity and/or fibrolytic, endogenous microflora-promoting activity.

The DFMs according to the present invention provide benefits to animals fed high levels of high-fibre plant by-products, such as dried distillers grains with solubles (DDGS).

Enzyme Producing DFM Assay:

High-throughput screening of these test strains was performed by replicate spot plating of 2 microliters liquid culture onto 15.0 ml of various substrate media types of interest in 100×100×15 mm grid plates. Cellulase, α-amylase, zeinase, soy protease, esterase, lipase and xylanase activities were determined based on specific substrate utilization by the individual strains. Media components used to assay the substrate utilization properties from enzymatic activity of the environmentally derived strains are described in Table 1. Assay plates were left to dry for 30 minutes following culture application, and then incubated at 32° C. for 24 hours. Enzymatic activities for each strain were determined by measuring the zone of substrate degradation in millimeters, as indicated by clearing of the surrounding edge of colony growth. Mean values from replicate plates were recorded.

TABLE 1

Media components used to assay the enzymatic activities illustrated by substrate utilization properties of environmentally derived *Bacillus*.

| Plate Assay | Media Composition | Extra Visualization Requirements |
|---|---|---|
| α-Amylase | Nutrient Agar, 2% Corn Starch | .05% Iodine Stain Solution |
| Soy Protease | Nutrient agar, 2% Purified Soy Protein | None; Measure Zone of Clearing in opaque media |
| Cellulase | 0.1% Ammonium Sulfate, 0.1% Potassium Phosphate Dibasic, 0.1% Yeast Extract, 1.0% Polypeptone, 1.5% Agar, 0.75% Carboxymethyl Cellulose (CMC) | 30 minute 0.05% Congo Red Dye stain, followed by 1M NaCl rinse. |
| Esterase/ Lipase | 1.0% Polypeptone, 1.5% Agar, 0.5% Yeast Extract, 1.5% Tween 80, 1.5% Tributyrin, 0.01% Victoria Blue B Dye (filtered). | None; Measure Zone of Clearing in opaque media |
| Zeinase | Nutrient Agar, 2% Purified Zein, solubilized in 70% methanol | None; Measure Zone of Clearing in opaque media |
| Xylanase | Nutrient Agar, 2% Xylan | None; Measure Zone of Clearing in opaque media |

In one embodiment the enzyme producing strain produces one or more the following enzyme activities: cellulase activity, α-amylase activity, xylanase activity, esterase activity, lipase activity, β-mannanase activity, protease activity (e.g. zeinase or soy protease activity) and combinations thereof.

In one embodiment preferably the enzyme producing strain produced one or more of the following enzyme activities: cellulose activity, xylanase activity β-mannanase activity, or combinations thereof.

In one embodiment the enzyme producing DFM is a strain selected from the group consisting of the species *Bacillus subtilis, Bacillus pumilus, Bacillus licheniformis, Bacillus amyloliquefaciens* or mixtures thereof.

In one embodiment preferably the enzyme producing DFM strain is selected from the group consisting of:
Bacillus subtilis AGTP BS3BP5 (NRRL B-50510),
Bacillus subtilis AGTP BS442 (NRRL B-50542),
Bacillus subtilis AGTP BS521 (NRRL B-50545),
Bacillus subtilis AGTP BS918 (NRRL B-50508),
Bacillus subtilis AGTP BS1013 (NRRL B-50509),
Bacillus pumilus AGTP BS 1068 (NRRL B-50543),
Bacillus subtilis AGTP BS1069 (NRRL B-50544),
Bacillus subtilis AGTP 944 (NRRL B-50548),
Bacillus pumilus AGTP KXII-1 (NRRL B-50546),
Bacillus subtilis 15A-P4 (PTA-6507),
Bacillus subtilis BS 2084 (NRRL B-50013),
Bacillus subtilis LSSAO1 (NRRL B-50104),
Bacillus subtilis 3A-P4 (PTA-6506),
Bacillus subtilis 22C-P1 (PTA-6508),
Bacillus licheniformis BL21 (NRRL B-50134),
Bacillus subtilis BS-27 (NRRL B-50105),
Bacillus subtilis BS18 (NRRL B-50633),
Bacillus subtilis BS278 (NRRL B-50634),
Bacillus licheniformis BL842 (NRRL B-50516).
or any derivative or variant thereof,
and combinations thereof.

The enzyme producing strain of DFM may be one or more of the strains taught in U.S. 61/527,371 and U.S. 61/526,881, both of which are incorporated herein by reference.

C5 Sugar Fermenting DFM Assay:

*Bacillus* strains are grown overnight on plates of Tryptic soy agar (Difco) at 32° C., and lactic acid bacteria are grown overnight on MRS agar (Difco) under anaerobic conditions at 37° C. API 50 CHB and API 50 CHL media (bioMerieux, Marcy l'Etoile, France) are inoculated with pure culture DFM (either *Bacillus* or lactic acid bacteria respectively) and applied to API 50CH® strips as per manufacturer's instructions. Strips are incubated at 32° C. (*Bacillus*) or 37° C. under anaerobic conditions (lactic acid bacteria) and monitored at 24 and 48 hours for colorimetric changes.

There term "C5 sugar" as used herein means any sugar having 5 carbons. C5 sugars may be referred to herein as pentoses.

The C5 sugars include D-arabinose, L-arabinose, D-ribose, D-xylose and L-xylose.

In one embodiment the C5 sugar-fermenting strain of DFM is selected from the group consisting of:
Bacillus subtilis 15A-P4 (PTA-6507)
Bacillus subtilis AGTP BS918 (NRRL B-50508)
Bacillus subtilis BS 2084 (NRRL B-50013)
Bacillus subtilis LSSAO1 (NRRL B-50104)
Enterococcus faecium I D7
Lactobacillus lactis DJ6 (PTA 6102)
Lactococcus lactis ID7 (PTA 6103),
or combinations thereof.

Short Chain Fatty Acid (SCFA)-Producing DFM Assay:

A 1% vol/vol inoculum of a 48 hr culture of a DFM is used to inoculate 10 ml tubes of modified Sodium Lactate Broth (NLB) (1% sodium lactate; Sigma-Aldrich, St Louis, MO; 1% tryptone; Oxoid Ltd., Hampshire, England, 0.5% yeast extract; Oxoid Ltd. and 0.5% $KH_2PO_4$) devoid of sodium lactate and supplemented with a commensurate amount (1% wt/vol) of one of nine different carbohydrates (lactate, glucose, galactose, arabinose, sucrose, starch, xylose, cellobiose, fructose; Sigma-Aldrich, St. Louis, MO). Cultures are grown under anaerobic conditions at 32° C., and after 0, 24, 48, and 72 hours of incubation, duplicate tubes are centrifuged at 5000×g for 10 min and spent broth collected from each culture. Production of short chain fatty acids in the spent broth was measured via high performance liquid chromatography (HPLC). Duplicate 1 ml samples of spent culture broth are removed from each sampling tube and mixed with 10 ml 0.005M H2504. Three mls of each diluted sample are filtered through a 0.2 micron filter into HPLC vials and capped. Samples are analysed for acetate, lactate, propionic acid, and butyric acid with a Waters 2695 separation module (Milford, Ma) using a 300×7.8 mm Bio-Rad (Hercules, CA) Aminex HPX-87H column. All analytes are detected with a Waters 2410 RI detector.

In one embodiment the short chain fatty acid (SCFA)-producing strain may be *Propionibacterium acidipropionici* P169.

In another embodiment the short chain fatty acid (SCFA)-producing strain may be *Enterococcus faecium* I D7.

The term "short chain fatty acid" as used herein includes volatile fatty acids as well as lactic acid.

In one embodiment the SCFA may be selected from the group consisting of: acetic acid, propionic acid, butyric acid, isobutyric acid, valeric acid, isovaleric acid, 2-methylbutyric acids and lactic acid.

In one embodiment the SCFA may be butyric acid.

FIBROLYTIC, ENDOGENOUS MICROFLORA-PROMOTING DFM ASSAY: A pen trial is conducted to determine the effects of a DFM on broiler chickens compared to a control without DFM. Samples are collected on days 11 and 42 of the trial. At each sampling date one bird is collected from each pen for a total of eight birds per treatment. Birds are euthanized and the total gastrointestinal tract (GIT) from below the gizzard to the ileal-cecal junction is collected from each bird. Cecal samples from each bird are sliced open and digesta and cecal tissue are collected in a whirl-pak bag and masticated in 99 ml of 0.1% peptone at 7.0 strokes/s for seconds to release mucosa-associated bacterial cells from the cecal tissue. Aliquots of the masticated solution containing bacteria from the cecal mucosa and digesta are flash-frozen in liquid nitrogen and stored at −20° C. until further analysis. Genomic DNA is isolated from 250 µl of each sample by phenol chloroform extraction and purified using Roche Applied Science High Pure PCR Template Purification Kit (Roche Diagnostics Corp., Indianapolis, IN). DNA from two birds per treatment is pooled in equal amounts and submitted for pyrosequencing as a single sample, resulting in four samples per treatment from each age. Bacterial tag-encoded FLX amplicon pyrosequencing is performed as described previously (Dowd, et al BMC Microbiol. 2008 Jul. 24; 8:125). The V1-V3 region of the 16S rRNA gene is amplified in each pooled sample using the primers 28 F (5'-GAGTTTGATCNTGGCTCAG) and 519R (5'-GTNTTACNGCGGCKGCTG). Pyrosequencing data is processed and analysed using the Qiime v.1.4.0. software pipeline. Briefly, raw sequence data is screened and trimmed based on quality. All sequences are trimmed to 350 bp.

Sequences are binned by individual samples based on barcode sequences. Barcode tags and primers are removed from the sequences and non-bacterial ribosomal sequences are removed. Sequences are clustered into operational taxonomic units (OTUs) at 97% similarity using uclust. Representative sequences from each OTU are then aligned using PyNAST and taxonomy is assigned by sequence comparison to known bacterial 16S rRNA gene sequences in the SILVA database using the RDP classifier. A random subsampling of sequences is performed to normalize each sample so that the same number of sequences are analyzed. Analysis of Variance (ANOVA) analysis is used to determine if any fibrolytic microflora (taxa) are significantly affected by treatment. The term "fibrolytic microflora" as used herein means a group of microorganisms that are able to process complex plant polysaccharides due to their ability to synthesize cellulolytic and hemicellulolytic enzymes.

The term "endogenous" as used herein means present in (or originating in) the GIT of a subject (e.g. an animal). In other words the fibrolytic, endogenous microflora is not a DFM. The fibrolytic, endogenous microflora is not added to the subject's feed.

Preferably the enzyme producing strain and/or the C-5 sugar-fermenting strain and/or the short-chain fatty acid-producing strains and/or the fibrolytic, endogenous microflora-promoting strain for use in the present invention comprises a viable microorganism. Preferably the enzyme producing strain and/or the C-5 sugar-fermenting strain and/or the short-chain fatty acid-producing strains and/or the fibrolytic, endogenous microflora-promoting strain comprises a viable bacterium or a viable yeast or a viable fungi.

In one preferred embodiment the enzyme producing strain and/or the C-5 sugar-fermenting strain and/or the short-chain fatty acid-producing strains and/or the fibrolytic, endogenous microflora-promoting strain comprises a viable bacterium.

The term "viable microorganism" means a microorganism which is metabolically active or able to differentiate.

In one embodiment the enzyme producing strain and/or the C-5 sugar-fermenting strain and/or the short-chain fatty acid-producing strains and/or the fibrolytic, endogenous microflora-promoting strain may be a spore forming bacterium and hence the term DFM may be comprised of or contain spores, e.g. bacterial spores. Therefore in one embodiment the term "viable microorganism" as used herein may include microbial spores, such as endospores or conidia.

In another embodiment the enzyme producing strain and/or the C-5 sugar-fermenting strain and/or the short-chain fatty acid-producing strains and/or the fibrolytic, endogenous microflora-promoting strain in the feed additive composition according to the present invention is not comprised of or does not contain microbial spores, e.g. endospores or conidia.

The microorganism may be a naturally occurring microorganism or it may be a transformed microorganism. The microorganism may also be a combination of suitable microorganisms. In some aspects, the enzyme producing strain and/or the C-5 sugar-fermenting strain and/or the short-chain fatty acid-producing strains and/or the fibrolytic, endogenous microflora-promoting strain according to the present invention may be one or more of the following: a bacterium, a yeast or a fungi.

Preferably the enzyme producing strain and/or the C-5 sugar-fermenting strain and/or the short-chain fatty acid-producing strains and/or the fibrolytic, endogenous microflora-promoting strain according to the present invention is a probiotic microorganism.

In the present invention, the term direct fed microbial (DFM) encompasses direct fed bacteria, direct fed yeast, direct fed fungi and combinations thereof.

Preferably the enzyme producing strain and/or the C-5 sugar-fermenting strain and/or the short-chain fatty acid-producing strains and/or the fibrolytic, endogenous microflora-promoting strain is a direct fed bacterium.

Suitably the enzyme producing strain and/or the C-5 sugar-fermenting strain and/or the short-chain fatty acid-producing strains and/or the fibrolytic, endogenous microflora-promoting strain may comprise a bacterium from one or more of the following genera: *Bacillus, Lactobacillus, Propionibacterium* and combinations thereof.

In one embodiment the enzyme producing strain and/or the C-5 sugar-fermenting strain and/or the short-chain fatty acid-producing strains and/or the fibrolytic, endogenous microflora-promoting strain may be a strain selected from the *Bacillus* genus.

In one embodiment the enzyme producing strain and/or the C-5 sugar-fermenting strain and/or the short-chain fatty acid-producing strains and/or the fibrolytic, endogenous microflora-promoting strain may be selected from the following *Bacillus* spp: *Bacillus subtilis, Bacillus cereus, Bacillus licheniformis, B. pumilus, B. coagulans, B. amyloliquefaciens, B. stearothermophilus, B. brevis, B. alkalophilus, B. clausii, B. halodurans, B. megaterium, B. circulans, B. lautus, B. thuringiensis* and *B. lentus* strains.

In at least some embodiments the *B. subtilis* strain(s) is (are) *Bacillus subtilis* AGTP BS3BP5, *Bacillus subtilis* AGTP BS442, *B. subtilis* AGTP BS521, *B. subtilis* AGTP BS918, *Bacillus subtilis* AGTP BS1013, *B. subtilis* AGTP BS1069, *B. subtilis* AGTP 944.

In at least some embodiments the *B. subtilis* strain(s) is (are) *Bacillus subtilis* 15A-P4 (PTA-6507), LSSA01 (NRRL B-50104).

In at least some embodiments the *B. pumilus* strain is *B. pumilus* AGTP BS 1068 or *B. pumilus* KX11-1.

Strains 3A-P4 (PTA-6506), 15A-P4 (PTA-6507) and 22C-P1 (PTA-6508) are publically available from American Type Culture Collection (ATCC). Strains 2084 (NRRL B-500130); LSSA01 (NRRL-B-50104); BS27 (NRRL B-50105) are publically available from the Agricultural Research Service Culture Collection (NRRL). Strain *Bacillus subtilis* LSSA01 is sometimes referred to as *B. subtilis* 8. These strains are taught in U.S. Pat. No. 7,754,469 B2. Danisco USA, Inc. of Waukesha, Wisconsin, USA deposited under the Budapest Treaty the following biological deposits with the Agricultural Research Service Culture Collection (NRRL) with the dates of the original deposits and accession numbers detailed below:

| Deposit | Accession Number | Deposit date |
| --- | --- | --- |
| *Bacillus subtilis* AGTP BS3BP5 | NRRL B-50510 | 13 May 2011 |
| *Bacillus subtilis* AGTP BS442 | NRRL B-50542 | 4 Aug. 2011 |
| *Bacillus subtilis* AGTP BS521 | NRRL B-50545 | 4 Aug. 2011 |
| *Bacillus subtilis* AGTP BS918 | NRRL B-50508 | 13 May 2011 |
| *Bacillus subtilis* AGTP BS1013 | NRRL B-50509 | 13 May 2011 |

-continued

| Deposit | Accession Number | Deposit date |
|---|---|---|
| Bacillus subtilis AGTP BS1069 | NRRL B-50544 | 4 Aug. 2011 |
| Bacillus subtilis AGTP 944 | NRRL B-50548 | 11 Aug. 2011 |
| Bacillus pumilus AGTP BS1068 | NRRL B-50543 | 4 Aug. 2011 |
| Bacillus pumilus AGTP KXII-1 | NRRL B-50546 | 5 Aug. 2011 |
| Bacillus subtilis BS18 | NRRL B-50633 | 9 Jan. 2012 |
| Bacillus subtilis BS278 | NRRL B-50634 | 9 Jan. 2012 |
| Bacillus licheniformis BL842 | NRRL B-50516 | 20 May 2011 |

Danisco USA, Inc. of Waukesha, Wisconsin, USA has authorised DuPont Nutrition Biosciences ApS of Langebrogade 1, PO Box 17, DK-1001, Copenhagen K, Denmark to refer to these deposited biological materials in this patent application and has given unreserved and irrevocable consent to the deposited material being made available to the public.

AgTech Products, Inc. of W227 N752 Westmound Drive, Waukesha, WI 53186, USA deposited under the Budapest Treaty the following biological deposit with the Agricultural Research Service Culture Collection (NRRL) with the date of the original deposit and accession number detailed below:

| Bacillus licheniformis BL21 | NRRL B-50134 | 15 Apr. 2008 |
|---|---|---|

AgTech Products, Inc has authorised DuPont Nutrition Biosciences ApS of Langebrogade 1, PO Box 17, DK-1001, Copenhagen K, Denmark to refer to this deposited biological material in this patent application and has given unreserved and irrevocable consent to the deposited material being made available to the public.

The table below summarises the enzyme producing capabilities of the selected strains using the "Enzyme producing DFM assay" above:

Summary of direct fed microbial candidate strains enzymatic activity.[a]

TABLE 2

Cellulase, xylanase, and β-mannanase activities of Bacillus strains.

| Isolate Name | CMCase (Cellulase) | Xylanase | β-Mannanase[1] |
|---|---|---|---|
| BS27 | 0.0 | 4.0 | 3.0 |
| BL21 | 3.0 | 0.0 | 2.5 |
| BL842 | 1.0 | 0.0 | 2.5 |
| BS18 | 3.0 | 3.0 | 3.5 |
| 15AP4 | 4.0 | 2.0 | 2.5 |
| 22CP1 | 3.0 | 5.0 | 2.0 |
| 3AP4 | 4.0 | 2.5 | 1.5 |
| BS278 | 4.0 | 3.0 | 1.0 |
| LSSAO1 | 3.5 | 4.0 | 3.3 |
| BS2084 | 4.0 | 3.0 | 1.0 |
| BS3BP5 | 3.3 | 3.0 | N/A |
| BS442 | 1.8 | 2.5 | 2.0 |
| BS521 | 6.0 | 4.0 | 2.0 |
| BS918 | 4.0 | 5.5 | 3.3 |
| BS1013 | 6.5 | 4.0 | 2.5 |

TABLE 2-continued

Cellulase, xylanase, and β-mannanase activities of Bacillus strains.

| Isolate Name | CMCase (Cellulase) | Xylanase | β-Mannanase[1] |
|---|---|---|---|
| BP1068 | 3.0 | 6.0 | 4.5 |
| BS1069 | 4.0 | 4.0 | 2.5 |
| 944 | 6.5 | 3.5 | 1.0 |
| KXII-1 | 2.5 | 5.0 | N/A |

[1]Mannanase (e.g. β-mannanase) is the name given to a class of enzymes which can hydrolyze 1,4-β-D-glycosidic bonds of β-mannan, galactomannan and glucomannan into mannan oligosaccharides and mannose, thus breaking down mannan containing hemicellulose, one of the major components of plant cell walls. β-mannanase is endo-1,4-β-D-mannanase (E.C. 3.2.1.78).

Suitably the enzyme producing strain and/or the C-5 sugar-fermenting strain and/or the short-chain fatty acid-producing strains and/or the fibrolytic, endogenous microflora-promoting strain for use in the present invention may be a strain selected from the Propionibacterium genus. In one embodiment the DFM for use in the present invention may be selected from the species Propionibacterium acidipropionici.

In one embodiment the DFM for use in the present invention is Propionibacterium acidipropionici P169.

Agtech Products, Inc. of W227 N752 Westmound Dr. Waukesha, WI 53186, USA deposited on 28 Jul. 2003 under the Budapest Treaty Propionibacterium acidipropionici P169 with the American Type Culture Collection (ATCC), Manassas, VA 20110-2209, USA as Accession no. PTA-5271. Propionibacterium acidipropionici P169 was referenced in granted patent U.S. Pat. No. 6,951,643B2 and is publically available from ATCC.

In one embodiment the enzyme producing strain and/or the C-5 sugar-fermenting strain and/or the short-chain fatty acid-producing strains and/or the fibrolytic, endogenous microflora-promoting strain for use in the present invention may be a strain from the Enterococcus genus. In one embodiment the DFM for use in the present invention may be selected from the species Enterococcus faecium.

In one embodiment the DFM for use in the present invention may be Enterococcus faecium ID7.

Lactococcus lactis ID7 (which was later reclassified as Enterococcus faecium ID7) was deposited on 22 Jun. 2004 under the Budapest Treaty as Lactococcus lactis ID7 with the American Type Culture Collection (ATCC), Manassas, VA 20110-2209, USA as Accession no. PTA-6103. Lactococcus lactis ID7 (which was later reclassified as Enterococcus faecium ID7) was referenced in granted patent U.S. Pat. No. 7,384,628 and is publically available from ATCC. When "Enterococcus faecium ID7" is used herein it will be understood that this organism's name is interchangeable with "Lactococcus lactis ID7" which was deposited as Accession no. PTA-6103. Enterococcus faecium ID7 is also publically available from Danisco Animal Nutrition, Denmark.

In one embodiment the enzyme producing strain and/or the C-5 sugar-fermenting strain and/or the short-chain fatty acid-producing strains and/or the fibrolytic, endogenous microflora-promoting strain for use in the present invention may be a strain from Lactobacillus genus. In one embodiment the enzyme producing strain and/or the C-5 sugar-fermenting strain and/or the short-chain fatty acid-producing strains and/or the fibrolytic, endogenous microflora-promoting strain may be selected from the following Lactobacillus spp: Lactobacillus buchneri, Lactobacillus acidophilus, Lactobacillus casei, Lactobacillus kefiri, Lactobacillus bifidus, *Lactobacillus brevis, Lactobacillus helveticus, Lactobacillus paracasei, Lactobacillus rhamnosus, Lactobacillus salivarius, Lactobacillus curvatus, Lactobacillus bulgaricus, Lactobacillus sakei, Lactobacillus reuteri, Lactobacillus fermentum, Lactobacillus farciminis, Lactobacillus lactis, Lactobacillus delbreuckii, Lactobacillus plantarum, Lactobacillus paraplantarum, Lactobacillus farciminis, Lactobacillus rhamnosus, Lactobacillus* crispatus, *Lactobacillus* gasseri, *Lactobacillus johnsonii* and *Lactobacillus jensenii*, and combinations of any thereof.

In one embodiment the DFM may be selected from one or more of the following strains: *Lactobacillus rhamnosus* CNCM-I-3698 and *Lactobacillus farciminis* CNCM-I-3699. These strains were deposited at the Collection Nationale de Cultures de Microorganims (CNCM) 25, Rue due Docteur Roux, F75724 Paris Cedex 15, France on 8 Dec. 2006 by Sorbial, Route de Spay 72700 Allonnes, France and all right, title and interest in the deposits were subsequently transferred to Danisco France SAS of 20, Rue de Brunel, 75017 Paris, France. Danisco France SAS has authorised DuPont Nutrition Biosciences ApS of Langebrogade 1, PO Box 17, DK-1001, Copenhagen K, Denmark to refer to these deposited biological materials in this patent application and have given unreserved and irrevocable consent to the deposited material being made available to the public.

In at least some embodiments the DFM may be selected from *Lactobacillus lactis* DJ6 (PTA 6102) and/or *Lactococcus lactis* ID7 (PTA 6103).

AgTech Products, Inc. of W227 N752 Westmound Drive, Waukesha, WI 53186, USA deposited under the Budapest Treaty the following biological deposits with the American Type Culture Collection (ATCC), Manassas, VA 20110-2209, USA with the dates of the original deposits and accession numbers detailed below:

| | | |
|---|---|---|
| *Lactobacillus lactis* DJ6 | PTA 6102 | 22 Jun. 2004 |
| *Lactococcus lactis* ID7 | PTA 6103 | 22 Jun. 2004 |

AgTech Products, Inc. has authorised DuPont Nutrition Biosciences ApS of Langebrogade 1, PO Box 17, DK-1001, Copenhagen K, Denmark to refer to these deposited biological materials in this patent application and has given unreserved and irrevocable consent to the deposited material being made available to the public.

In at least one embodiment, more than one of the strain(s) described herein is (are) combined.

Therefore the enzyme producing strain and/or the C-5 sugar-fermenting strain and/or the short-chain fatty acid-producing strain and/or the fibrolytic, endogenous microflora-promoting strain used in the present invention may be a combination of at least two, suitably at least three, suitably at least four DFM strains described herein, e.g. DFM strains selected from the group consisting of *Bacillus subtilis* AGTP BS3BP5, *Bacillus subtilis* AGTP BS442, *B. subtilis* AGTP BS521, *B. subtilis* AGTP BS918, *Bacillus subtilis* AGTP BSI 013, *B. subtilis* AGTP BSI 069, *B. subtilis* AGTP 944, *B. pumilus* AGTP BS 1068, *B. pumilus* KXI 1-1, *Propionibacterium* P169, *Lactobacillus rhamnosus* CNCM-I-3698 or *Lactobacillus farciminis* CNCM-I-3699.

In one embodiment preferably the DFM may be one or more of the group consisting of *Bacillus subtilis* AGTP BS3BP5, *Bacillus subtilis* AGTP BS442, *B. subtilis* AGTP BS521, *B. subtilis* AGTP BS918, *Bacillus subtilis* AGTP BSI 013, *B. subtilis* AGTP BSI 069, *B. subtilis* AGTP 944, *B. pumilus* AGTP BS 1068, *B. pumilus* KXI 1-1 and a combination thereof.

Any *Bacillus, Lactobacillus* or *Propionibacterium* derivative or variant is also included and is useful in the methods described and claimed herein.

In some embodiments, *Bacillus* variant strains having all the characteristics of *Bacillus subtilis* AGTP BS3BP5, *Bacillus subtilis* AGTP BS442, *B. subtilis* AGTP BS521, *B. subtilis* AGTP BS918, *Bacillus subtilis* AGTP BSI 013, *B. subtilis* AGTP BSI 069, *B. subtilis* AGTP 944, *B. pumilus* AGTP BS 1068 or *B. pumilus* KXI 1-1 are also included and are useful in the methods described and claimed herein.

As used herein, a "variant" has at least 80% identity of genetic sequences with the disclosed strains using random amplified polymorphic DNA polymerase chain reaction (RAPD-PCR) analysis. The degree of identity of genetic sequences can vary. In some embodiments, the variant has at least 85%, 90%, 95%, 96%, 97%, 98% or 99% identity of genetic sequences with the disclosed strains using RAPD-PCR analysis.

Six primers that can be used for RAPD-PCR analysis include the following: Primer 1 (5'-GGTGCGGGAA-3'), Primer 2 (5'-GTTTCGCTCC-3'), Primer 3 (5'-GTAGACCCGT-3'), Primer 4 (5'-AAGAGCCCGT-3'), Primer 5 (5'-AACGCGCAAC-3'), Primer 6 (5'-CCCGTCAGCA-3'). RAPD analysis can be performed using Ready-to-Go™ RAPD Analysis Beads (Amersham Biosciences, Sweden), which are designed as pre-mixed, pre-dispensed reactions for performing RAPD analysis.

The direct fed bacterium used in the present invention may be of the same type (genus, species and strain) or may comprise a mixture of genera, species and/or strains.

Preferably the DFM to be used in accordance with the present invention is a microorganism which is generally recognised as safe and, which is preferably GRAS approved.

A skilled person will readily be aware of specific species and or strains of microorganisms from within the genera described herein which are used in the food and/or agricultural industries and which are generally considered suitable for animal consumption.

Preferably, the DFM used in accordance with the present invention is one which is suitable for animal consumption.

Advantageously, where the product is a feed or feed additive composition, the viable DFM should remain effective through the normal "sell-by" or "expiration" date of the product during which the feed or feed additive composition is offered for sale by the retailer. The desired lengths of time and normal shelf life will vary from feedstuff to feedstuff and those of ordinary skill in the art will recognise that shelf-life times will vary upon the type of feedstuff, the size of the feedstuff, storage temperatures, processing conditions, packaging material and packaging equipment.

In some embodiments it is important that the DFM is tolerant to heat, i.e. is thermotolerant. This is particularly the case where the feed is pelleted. Therefore in one embodiment the DFM may be a thermotolerant microorganism, such as a thermotolerant bacteria, including for example *Bacillus* spp.

In some embodiments it may be preferable that the DFM is a spore producing bacteria, such as Bacilli, e.g. *Bacillus* spp. Bacilli are able to from stable endospores when conditions for growth are unfavorable and are very resistant to heat, pH, moisture and disinfectants.

Suitably the DFM is not an inactivated microorganism.

In one embodiment the DFM may be a viable or inviable microorganism which is used in isolated or semi-isolated form. The DFM may be used in combination with or without the growth medium in which it was cultured.

In one embodiment, the DFM is capable of producing colony forming units when grown on an appropriate media. The appropriate media may comprise (or consist of) a feed or a feed constituent.

In one embodiment, the DFM is incapable of producing colony forming units when grown on an appropriate media. The appropriate media may comprise (or consist of) a feed or a feed constituent.

Irrespective of whether the DFM is capable or incapable of producing colony forming units when grown on an appropriate media—the cells may be still metabolically active (e.g. even if they are unable to divide).

In one embodiment the DFM may be administered as inviable cells.

In one embodiment the DFM may be administered as a viable microorganism.

The DFM may be dosed appropriately.

Suitably dosages of DFM in the feed may be between about $1\times10^3$ CFU/g feed to about $1\times10^9$ CFU/g feed, suitably between about $1\times10^4$ CFU/g feed to about $1\times10^8$ CFU/g feed, suitably between about $7.5\times10^4$ CFU/g feed to about $1\times10^7$ CFU/g feed.

In one embodiment the DFM is dosed in the feedstuff at more than about $1\times10^3$ CFU/g feed, suitably more than about $1\times10^4$ CFU/g feed, suitably more than about $7.5\times10^4$ CFU/g feed. Suitably dosages of DFM in the feed additive composition may be between about $1\times10^5$ CFU/g composition to about $1\times10^{13}$ CFU/g composition, suitably between about $1\times10^6$ CFU/g composition to about $1\times10^{12}$ CFU/g composition, suitably between about $3.75\times10^7$ CFU/g composition to about $1\times10^{11}$ CFU/g composition.

In one embodiment the DFM is dosed in the feed additive composition at more than about $1\times10^5$ CFU/g composition, suitably more than about $1\times10^6$ CFU/g composition, suitably more than about $3.75\times10^7$ CFU/g composition.

In a preferred embodiment the DFM may be dosed in the feed additive composition at between about $5\times10^7$ to about $1\times10^9$ CFU/g, suitably at between about $1\times10^8$ to about $5\times10^8$ CFU/g composition.

In another preferred embodiment the DFM may be dosed in the feed additive composition at between about $5\times10^3$ to about $5\times10^5$ U/g, suitably at between about $1\times10^4$ to about $1\times10^5$ CFU/g composition.

Fibre Degrading Enzymes

The DFM as taught herein may be used in combination with at least one xylanase and at least one β-glucanase (and optionally at least one further fibre degrading enzyme).

β-glucanase or endo-glucanase is the name given to a class of enzymes which can hydrolyze (1,3)-β-D-glycosidic and/or (1,4)-β-D-glycosidic bonds of (1,4)-β-glucan, (1,3; 1,4)-β-glucan and cellulose into glucose oligosaccharides and glucose, thus breaking down cellulose and hemicellulose, the major components of plant cell walls.

The β-glucanase for use in the present invention may be any commercially available β-glucanase.

In one embodiment the β-glucanase is an endoglucanase, e.g. an endo-1,4-β-D-glucanase (classified as E.C. 3.2.1.4).

Suitably, the β-glucanase for use in the present invention may be a β-glucanase from *Bacillus, Trichoderma, Aspergillus, Thermomyces, Fusarium* and *Penicillium*.

In one embodiment the fibre degrading enzyme may be a β-glucanase produced from one or more of the expression hosts selected from the group consisting of: *Bacillus lentus, Aspergillus niger, Trichoderma reesei, Penicillium funiculosum, Trichoderma longibrachiatum, Humicola insolens, Bacillus amyloliquefaciens, Aspergillus aculeatus, Aspergillus aculeatus*.

In one embodiment the fibre degrading enzyme may be one or more of the following commercial products which comprises at least a 8-glucanase fibre degrading enzyme:

Econase® GT or Econase® BG (available from AB Vista), Rovabio Excel® (available from Adisseo), Endo-feed® DC and Amylofeed® (available from Andres Pintaluba S.A.), AveMix® XG10 (from Aveve), Natugrain®, Natugrain®TS, or Natugrain® TS/L (available from BASF), Avizyme® 1210, Avizyme® SX, Grindazym® GP, Grindazym® GV, Porzyme® 8100, Porzyme® 9102, Porzyme® tp100, AXTRA® XB, Avizyme® 1100, Avizyme® 1110, Avizyme® 1202, Porzyme® sf or Porzyme® SP (available from Danisco Animal Nutrition), Bio-Feed Plus®, Ronozyme A®, Ronozyme VP® or Roxazyme G2® (available from DSM), Hostazym C® (available from Huvepharma), Kemzyme W dry or Kemzyme W liquid (available from Kemin), Biogalactosidase BL (available from Kerry Ingredients), Safizyme G (available from Le Saffre), or Feedlyve AGL (available from Lyven).

In one embodiment the 8-glucanase may be obtained from Axtra®XB.

β-glucanase may be dosed in any suitable amount.

In one embodiment the 8-glucanase for use in the present invention may be present in the feedstuff in a range of about 50 BGU/kg feed to about 50000 BGU/kg feed, suitably about 100 BGU/kg feed to about 1000 BGU/kg feed.

The β-glucanase for use in the present invention may be present in the feedstuff in a range of about 75 BGU/kg feed to about 400 BGU/kg feed, suitably about 150 BGU/kg feed to about 200 BGU/kg feed.

In one embodiment the β-glucanase is present in the feedstuff at less than 1000 BGU/kg feed, suitably less than about 500 BGU/kg feed, suitably less than 250 BGU/kg feed.

In one embodiment the β-glucanase is present in the feedstuff at more than 75 BGU/kg feed, suitably more than 100 BGU/kg feed.

Suitably, the β-glucanase is present in the feed additive composition in the range of about 150 BGU/g composition to about 3000 BGU/g composition, suitably in the range of about 300 BGU/g composition to about 1500 BGU/g composition.

In one embodiment the β-glucanase is present in the feed additive composition at less than 5000 BGU/g composition, suitably at less than 4000 BGU/g composition, suitably at less than 3000 BGU/g composition, suitably at less than 2000 BGU/g composition.

In one embodiment the β-glucanase is present in the feed additive composition at more than BGU/g composition, suitably at more than 100 BGU/g composition, suitably at more than 125 BGU/g composition.

In some embodiments the activity of β-glucanase can be calculated using the "β-glucanase Activity Assay (BGU)" as taught herein.

In one embodiment the β-glucanase for use in the present invention may have β-glucanase activity as determined using the "β-glucanase Activity Assay (CMC U/g)" taught herein.

The term "fibre degrading enzyme" as used herein may include one or more of the following fibre degrading enzymes: a xylanase (e.g. an endo-1,4-β-D-xylanase (E.C. 3.2.1.8) or a 1,4 β-xylosidase (E.C. 3.2.1.37)), a β-glucanase (E.C. 3.2.1.4), a cellobiohydrolase (E.C. 3.2.1.176 and E.C. 3.2.1.91), a 8-glucosidase (E.C. 3.2.1.21), a feruloyl esterase (E.C. 3.1.1.73), an α-arabinofuranosidase (E.C. 3.2.1.55), a pectinase (e.g. an endopolygalacturonase (E.C. 3.2.1.15), an exopolygalacturonase (E.C. 3.2.1.67) or a pectate lyase (E.C. 4.2.2.2)), or combinations thereof.

The term "further fibre degrading enzyme" as used herein may include one or more of the following fibre degrading enzymes: a cellobiohydrolase (E.C. 3.2.1.176 and E.C. 3.2.1.91), a β-glucosidase (E.C. 3.2.1.21), a β-xylosidase (E.C. 3.2.1.37), a feruloyl esterase (E.C. 3.1.1.73), an α-arabinofuranosidase (E.C. 3.2.1.55), a pectinase (e.g. an endopolygalacturonase (E.C. 3.2.1.15), an exopolygalacturonase (E.C. 3.2.1.67) or a pectate lyase (E.C. 4.2.2.2)), or combinations thereof.

It will also be understood by a person skilled in the art that "a further fibre degrading enzyme" may encompass multiple further fibre degrading enzymes.

In one embodiment the DFM as taught herein may be used in combination with at least one xylanase, at least one β-glucanase and at least one further fibre degrading enzyme.

In another embodiment the DFM as taught herein may be used in combination with at least one xylanase, at least one β-glucanase and two (or at least two) further fibre degrading enzymes.

In another embodiment the DFM as taught herein may be used in combination with at least one xylanase, at least one β-glucanase and three (or at least three) further fibre degrading enzymes.

In another embodiment the DFM as taught herein may be used in combination with at least one xylanase, at least one β-glucanase and four (or at least four) further fibre degrading enzymes.

In one embodiment the DFM as taught herein may be used in combination with a broth or a solid-state fermentation product containing measurable enzyme activity or activities of the present invention.

In one embodiment the DFM as taught herein may be used in combination with the enzymes of the present invention, which enzymes are in isolated or purified form.

In one embodiment the DFM as taught herein may be used in combination with the enzymes of the present invention, which enzymes are exogenous to the DFM in the composition (e.g. if the DFM is an enzyme producing strain).

Preferably, the fibre degrading enzyme(s) is present in the feedstuff in the range of about 0.05 to 5 g of enzyme protein per metric ton (MT) of feed (or mg/kg).

Suitably, each fibre degrading enzyme may be present in the feedstuff in the range of about to 5 g of enzyme protein per metric ton (MT) of feed (or mg/kg).

Suitably, the fibre degrading enzymes in total are present in the feedstuff in the range of about 0.05 to 5 g of enzyme protein per metric ton (MT) of feed (or mg/kg).

Preferably, the fibre degrading enzyme(s) is present in the feed additive composition (or premix) in the range of about 0.05 to 100 mg protein/g of composition (e.g. at a total inclusion in the diet of 50 to 1000 g/MT).

Suitably, each fibre degrading enzyme is present in the feed additive composition (or premix) in the range of about 0.05 to 100 mg protein/g of composition (e.g. at a total inclusion in the diet of 50 to 1000 g/MT).

Suitably, the fibre degrading enzymes in total is present in the feed additive composition (or premix) in the range of about 0.05 to 100 mg protein/g of composition (e.g. at a total inclusion in the diet of 50 to 1000 g/MT).

In a preferred embodiment the fibre degrading enzyme (e.g. each fibre degrading enzyme or the fibre degrading enzymes in total) may be in the feed additive composition (or premix) in the range of about 50 to about 700 g/MT of feed. Suitably the fibre degrading enzyme (e.g. each fibre degrading enzyme or the fibre degrading enzymes in total) may be in the feed additive composition (or premix) at about 100 to about 500 g/MT of feed.

In one embodiment the further fibre degrading enzyme(s) for use in the present invention may comprise (or consist essentially of, or consist of) a cellobiohydrolase (E.C. 3.2.1.176 and E.C. 3.2.1.91).

In another embodiment the further fibre degrading enzyme(s) for use in the present invention may comprise (or consist essentially of, or consist of) a β-glucosidase (E.C. 3.2.1.21).

Suitably the further fibre degrading enzyme may comprise (or consist essentially of, or consist of) a cellobiohydrolase (E.C. 3.2.1.176 and E.C. 3.2.1.91), a β-glucosidase (E.C. 3.2.1.21) or combinations thereof.

In another one embodiment the further fibre degrading enzyme(s) for use in the present invention may comprise (or consist essentially of, or consist of) a β-xylosidase (E.C. 3.2.1.37). In one embodiment the fibre degrading enzyme(s) for use in the present invention may comprise (or consist essentially of, or consist of) a feruloyl esterase (E.C. 3.1.1.73).

In another embodiment the further fibre degrading enzyme for use in the present invention may comprise (or consist essentially of, or consist of) an α-arabinofuranosidase (E.C. 3.2.1.55). In a yet further embodiment the further fibre degrading enzyme(s) for use in the present invention may comprise (or consist essentially of, or consist of) a pectinase (e.g. an endopolygalacturonase (E.C. 3.2.1.15), an exopolygalacturonase (E.C. 3.2.1.67) or a pectate lyase (E.C. 4.2.2.2)).

In a preferred embodiment the further fibre degrading enzyme(s) for use in the present invention may comprise (or consist essentially of, or consist of) one or more (suitably two or two or more, suitably three) pectinase(s) selected from the group consisting of: an endopolygalacturonase (E.C. 3.2.1.15), an exopolygalacturonase (E.C. 3.2.1.67) and a pectate lyase (E.C. 4.2.2.2).

In one embodiment the further fibre degrading enzyme(s) for use in the present invention may comprise (or consist essentially of, or consist of) a cellobiohydrolase (E.C. 3.2.1.176 and E.C. 3.2.1.91), a β-glucosidase (E.C. 3.2.1.21), a β-xylosidase (E.C. 3.2.1.37), a feruloyl esterase (E.C. 3.1.1.73), an α-arabinofuranosidase (E.C. 3.2.1.55), and/or a pectinase (e.g. an endopolygalacturonase (E.C. 3.2.1.15), an exopolygalacturonase (E.C. 3.2.1.67) or a pectate lyase (E.C. 4.2.2.2).

The present invention relates to the combination of at least one xylanase, with at least one β-glucanase and at least one specific DFM as taught herein.

In a preferred embodiment, the at least one xylanase, the at least one β-glucanase and the at least one specific DFM as taught herein may be combined with a further fibre degrading enzyme as taught herein.

The present invention further relates to the combination of at least one xylanase and at least one β-glucanase, with at least two, such as at least three or at least four or at least five, further fibre degrading enzymes and at least one specific DFM as taught herein.

Xylanase is the name given to a class of enzymes which degrade the linear polysaccharide beta-1,4-xylan into xylose, thus breaking down hemicellulose, one of the major components of plant cell walls.

The xylanase for use in the present invention may be any commercially available xylanase. Suitably the xylanase may be an endo-1,4-β-d-xylanase (classified as E.C. 3.2.1.8).

In one embodiment preferably the xylanase is an endoxylanase, e.g. an endo-1,4-β-d-xylanase. The classification for an endo-1,4-β-d-xylanase is E.C. 3.2.1.8.

In one embodiment the present invention relates to a DFM in combination with an endoxylanase, e.g. an endo-1,4-β-d-xylanase, and another enzyme.

All E.C. enzyme classifications referred to here relate to the classifications provided in Enzyme Nomenclature—Recommendations (1992) of the nomenclature committee of the International Union of Biochemistry and Molecular Biology—ISBN 0-12-226164-3.

Suitably, the xylanase for use in the present invention may be a xylanase from *Bacillus* or *Trichoderma*.

In one embodiment the xylanase may be a xylanase comprising (or consisting of) an amino acid sequence shown herein as SEQ ID No. 1, a xylanase comprising (or consisting of) an amino acid sequence shown herein as SEQ ID No. 2 or a xylanase comprising (or consisting of) an amino acid sequence shown herein as SEQ ID No. 3 (FveXyn4), a xylanase from *Trichoderma reesei*, Econase XT™ or Rovabio Excel™.

In one embodiment the xylanase may be the xylanase in Axtra XAP® or Avizyme 1502® or AxtraXB™, both commercially available products from Danisco A/S.

In one preferred embodiment the xylanase for use in the present invention may be one or more of the xylanases in one or more of the commercial products below:

| Commercial Name ® | Company | Xylanase type | Xylanase source |
|---|---|---|---|
| Allzyme PT | Alltech | endo-1,4-β-xylanase | *Aspergillus Niger* |
| Amylofeed | Andrés Pintaluba S.A | endo-1,4-β-xylanase | *Aspergillus Niger* (phoenicis) |
| Avemix 02 CS | Aveve | endo-1,4-β-xylanase | *Trichoderma reesei* |
| AveMix XG 10 | Aveve, NL | endo-1,4-β-xylanase | *Trichoderma reesei* |
| Avizyme 1100 | Danisco | endo-1,4-β-xylanase | *Trichoderma longibrachiatum* |
| Avizyme 1110 | Danisco | endo-1,4-β-xylanase | *Trichoderma longibrachiatum* |
| Avizyme 1202 | Danisco | endo-1,4-β-xylanase | *Trichoderma longibrachiatum* |
| Avizyme 1210 | Danisco | endo-1,4-β-xylanase | *Trichoderma longibrachiatum* |
| Avizyme 1302 | Danisco | endo-1,4-β-xylanase | *Trichoderma longibrachiatum* |
| Avizyme 1500 | Danisco | endo-1,4-β-xylanase | *Trichoderma longibrachiatum* |
| Avizyme 1502 | Danisco | endo-1,4-β-xylanase | *Trichoderma longibrachiatum* |
| Avizyme 1505 | Danisco | endo-1,4-β-xylanase | *Trichoderma longibrachiatum* |
| Avizyme SX | Danisco | endo-1,4-β-xylanase | *Trichoderma longibrachiatum* |
| Axtra XAP | Danisco | endo-1,4-β-xylanase | *Trichoderma longibrachiatum* |
| Axtra XB | Danisco | endo-1,4-β-xylanase | *Trichoderma longibrachiatum* |
| Belfeed MP100 | Beldem | endo-1,4-β-xylanase | *Bacillus subtilis* |
| Biofeed Combi | Novozymes A/S | endo-1,4-β-xylanase | Produced in *Aspergillus oryzae* carrying a gene from *Thermomyces lanuginosis* and *Aspergillus aculeatus* |
| Biofeed Plus | DSM | endo-1,4-β-xylanase | *Humicola insolens* |
| Biofeed Wheat | Novozymes A/S | endo-1,4-β-xylanase | Produced in *Aspergillus oryzae* carrying a gene from *Thermomyces lanuginosis* |
| Danisco Glycosidase (TPT/L) | Danisco Animal Nutrition | endo-1,4-β-xylanase | *Trichoderma reesei* |
| Danisco Xylanase | Danisco | endo-1,4-β-xylanase | *Trichoderma reesei* |
| Econase Wheat Plus | ABenzymes/ABVista | endo-1,4-β-xylanase | *Trichoderma reesei* |
| Econase XT | ABVista | endo-1,4-β-xylanase | *Trichoderma reesei* |
| Endofeed ® DC | Andres Pintaluba S.A. | endo-1,4-β-xylanase | *Aspergillus Niger* |
| Feedlyve AXC | Lyven | endo-1,4-β-xylanase | *Trichoderma koningii* |
| Feedlyve AXL | Lyven | endo-1,4-β-xylanase | *Trichoderma longibrachiatum* |
| Grindazym GP | Danisco | endo-1,4-β-xylanase | *Aspergillus Niger* |
| Grindazym GV | Danisco | endo-1,4-β-xylanase | *Aspergillus Niger* |
| Hostazym X | Huvepharma | endo-1,4-β-xylanase | *Trichoderma longibrachiatum* |
| Kemzyme Plus Dry | Kemin | endo-1,4-β-xylanase | *Trichoderma viride* |
| Kemzyme Plus Liquid | Kemin | endo-1,4-β-xylanase | *Trichoderma viride* |

| Commercial Name ® | Company | Xylanase type | Xylanase source |
| --- | --- | --- | --- |
| Kemzyme W dry | Kemin | endo-1,4-β-xylanase | *Trichoderma viride* |
| Kemzyme W liquid | Kemin | endo-1,4-β-xylanase | *Trichoderma viride* |
| Natugrain | BASF | endo-1,4-β-xylanase | *Trichoderma longibrachiatum* |
| Natugrain TS Plus | BASF | endo-1,4-β-xylanase | *Aspergillus Niger* |
| Natugrain Wheat | BASF | endo-1,4-β-xylanase | *Aspergillus Niger* |
| Natugrain ® TS/L | BASF | endo-1,4-β-xylanase | *Aspergillus Niger* |
| Natuzyme | Bioproton | endo-1,4-β-xylanase | *Trichoderma longibrachiatum/ Trichoderma reesei* |
| Nutrase Xyla | Nutrex | endo-1,4-β-xylanase | *Bacillus subtilis* |
| Porzyme 8100 | Danisco | endo-1,4-β-xylanase | *Trichoderma longibrachiatum* |
| Porzyme 8300 | Danisco | endo-1,4-β-xylanase | *Trichoderma longibrachiatum* |
| Porzyme 9102 | Danisco | endo-1,4-β-xylanase | *Trichoderma longibrachiatum* |
| Porzyme 9310/Avizyme 1310 | Danisco | endo-1,4-β-xylanase | *Trichoderma longibrachiatum* |
| Porzyme tp100 | Danisco | endo-1,4-β-xylanase | *Trichoderma longibrachiatum* |
| Ronozyme AX | DSM | endo-1,4-β-xylanase | *Thermomyces lanuginosus* gene expressed in *Aspergillus oryzae* |
| Ronozyme WX | DSM/Novozymes | endo-1,4-β-xylanase | *Thermomyces lanuginosus* gene expressed in *Aspergillus oryzae* |
| Rovabio Excel | Adisseo | endo-1,4-β-xylanase | *Penicillium funiculosum* |
| Roxazyme G2 | DSM/Novozymes | endo-1,4-β-xylanase | *Trichoderma longibrachiatum* |
| Safizym X | Le Saffre | endo-1,4-β-xylanase | *Trichoderma longibrachiatum* |
| Xylanase | Lyven | endo-1,4-β-xylanase | *Trichoderma longibrachiatum* |

In one embodiment the xylanase may be a xylanase comprising (or consisting of) a polypeptide sequence shown herein as SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, or SEQ ID No. 12; or a variant, homologue, fragment or derivative thereof having at least 75% identity (such as at least 80%, 85%, 90%, 95%, 98% or 99% identity) with SEQ ID No. 1 or SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, or SEQ ID No. 12; or a polypeptide sequence which comprises SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, or SEQ ID No. 12 with a conservative substitution of at least one of the amino acids.

In one embodiment the xylanase may comprise a polypeptide sequence shown herein as SEQ ID No. 1, SEQ ID No. 2 or SEQ ID No. 3, or a variant, homologue, fragment or derivative thereof having at least 98.5% (e.g. at least 98.8 or 99 or 99.1 or 99.5%) identity with SEQ ID No. 1 or SEQ ID No. 2 or SEQ ID No. 3

SEQ ID No. 1:
mklssflytaslvaa*IPTAIEPR* QAADSINKLIKN

KGKLYYGTITDPNLLGVAKDTAIIKADFGAVTPEN

SGKWDATEPSQGKFNFGSFDQVVNFAQQNGLKVRG

HTLVWHSQLPQVVVKNINDKATLTKVIENHVTQVV

GRYKGKIYAWDVVNEIFEWDGTLRKDSHFNNVFGN

DDYVGIAFRAARKADPNAKLYINDYSLDSGSASKV

TKGMVPSVKKWLSQGVPVDGIGSQTHLDPGAAGQI

QGALTALANSGVKEVAITELDIRTAPANDYATVTK

ACLNVPKCIGITVWGVSDKNSWRKEHDSLLFDANY

NPKPAYTAVVNALR

SEQ ID No. 2:
*IPTAIEPR* QAADSINKLIKNKGKLYYGTITDPNLL

GVAKDTAIIKADFGAVTPENSGKWDATEPSQGKFN

-continued
FGSFDQVVNFAQQNGLKVRGHTLVWHSQLPQVVVK

NINDKATLTKVIENHVTQVVGRYKGKIYAWDVVNE

IFEWDGTLRKDSHFNNVFGNDDYVGIAFRAARKAD

PNAKLYINDYSLDSGSASKVTKGMVPSVKKWLSQG

VPVDGIGSQTHLDPGAAGQIQGALTALANSGVKEV

AITELDIRTAPANDYATVTKACLNVPKCIGITVWG

VSDKNSWRKEHDSLLFDANYNPKPAYTAVVNALR

SEQ ID No. 3:
QAADSINKLIKNKGKLYYGTITDPNLLGVAKDTAI

IKADFGAVTPENSGKWDATEPSQGKFNFGSFDQVV

NFAQQNGLKVRGHTLVWHSQLPQVVVKNINDKATL

TKVIENHVTQVVGRYKGKIYAWDVVNEIFEWDGTL

RKDSHFNNVFGNDDYVGIAFRAARKADPNAKLYIN

DYSLDSGSASKVTKGMVPSVKKWLSQGVPVDGIGS

QTHLDPGAAGQIQGALTALANSGVKEVAITELDIR

TAPANDYATVTKACLNVPKCIGITVWGVSDKNSWR

KEHDSLLFDANYNPKPAYTAVVNALR

SEQ ID No. 4:
mklssflytaslvaaIPTAIEPR QASDSINKLIKN

KGKLYYGTITDPNLLGVAKDTAIIKADFGAVTPEN

SGKWDATEPSQGKFNFGSFDQVVNFAQQNGLKVRG

HTLVWHSQLPQVVVKNINDKATLTKVIENHVTNVV

GRYKGKIYAWDVVNEIFDWDGTLRKDSHFNNVFGN

DDYVGIAFRAARKADPNAKLYINDYSLDSGSASKV

TKGMVPSVKKWLSQGVPVDGIGSQTHLDPGAAGQI

QGALTALANSGVKEVAITELDIRTAPANDYATVTK

ACLNVPKCIGITVWGVSDKNSWRKEHDSLLFDANY

NPKAAYTAVVNALR

SEQ ID No. 5:
*IPTAIEPR* QASDSINKLIKNKGKLYYGTITDPNLL

GVAKDTAIIKADFGAVTPENSGKWDATEPSQGKFN

FGSFDQVVNFAQQNGLKVRGHTLVWHSQLPQVVVK

NINDKATLTKVIENHVTNVVGRYKGKIYAWDVVNE lFDWDGTLRKDSHFNNVFGNDDYVGIAFRAARKAD

PNAKLYINDYSLDSGSASKVTKGMVPSVKKWLSQG

VPVDGIGSQTHLDPGAAGQIQGALTALANSGVKEV

AITELDIRTAPANDYATVTKACLNVPKCIGITVWG

VSDKNSWRKEHDSLLFDANYNPKAAYTAVVNALR

SEQ ID No. 6:
QASDSINKLIKNKGKLYYGTITDPNLLGVAKDTAI

IKADFGAVTPENSGKWDATEPSQGKFNFGSFDQVV

NFAQQNGLKVRGHTLVWHSQLPQVVVKNINDKATL

TKVIENHVTNVVGRYKGKIYAWDVVNElFDWDGTL

-continued
RKDSHFNNVFGNDDYVGIAFRAARKADPNAKLYIN

DYSLDSGSASKVTKGMVPSVKKWLSQGVPVDGIGS

QTHLDPGAAGQIQGALTALANSGVKEVAITELDIR

TAPANDYATVTKACLNVPKCIGITVWGVSDKNSWR

KEHDSLLFDANYNPKAAYTAVVNALR

SEQ ID No. 7:
mvsfkylflaasalgala**APVEVEESSWFNETALH

EFAERAGTPSSTGWNNGYYYSFVVTDNGGTVNYQN

GNGGSYSVQWKDTGNFVGGKGWNPGSARTINYSGS

FNPSGNAYLTVYGVVTTNPLVEYYIVENYGTYNPG

NGGTYRGSVYSDGANYNIYTATRYNAPSIEGDKTF

TQYWSVRQSKRTGGTVTTANHFNAWAQLGMSLGTH

NYQIVATEGYQSSGSSSITVY**

SEQ ID No. 8:
APVEVEESSWFNETALHEFAERAGTPSSTGWNNGY

YYSFVVTDNGGTVNYQNGNGGSYSVQWKDTGNFVG

GKGWNPGSARTINYSGSFNPSGNAYLTVYGVVTTN

PLVEYYIVENYGTYNPGNGGTYRGSVYSDGANYNI

YTATRYNAPSIEGDKTFTQYWSVRQSKRTGGTVTT

ANHFNAWAQLGMSLGTHNYQIVATEGYQSSGSSSI

TVY

SEQ ID No. 9:
AGTPSSTGWNNGYYYSFVVTDNGGTVNYQNGNGGS

YSVQWKDTGNFVGGKGWNPGSARTINYSGSFNPSG

NAYLTVYGVVTTNPLVEYYIVENYGTYNPGNGGTY

RGSVYSDGANYNIYTATRYNAPSIEGDKTFTQYWS

VRQSKRTGGTVTTANHFNAWAQLGMSLGTHNYQIV

ATEGYQSSGSSSITVY

SEQ ID No. 10:
MVSFTSLLAAVSAVTGVMALPSAQPVDGMSVVERD

PPTNVLDKRTQPTTGTSGGYYFSFVVTDTPNSVTY

TNGNGGQFSMQWSGNGNHVGGKGVVMPGTSRTIKY

SGSYNPNGNSYLAVYGVVTRNPLIEYYIVENFGTY

NPSSGGQKKGEVNVDGSVYDIYVSTRVNAPSIDGN

KTFQQYWSVRRNKRSSGSVNTGAHFQAWKNVGLNL

GTHDYQILAVEGYYSSGSASMTVSQ

SEQ ID No. 11:
*LPSAQPVDGMSVVERDPPTNVLDK*RTQPTTGTSGG

YYFSFVVTDTPNSVTYTNGNGGQFSMQWSGNGNHV

GGKGVVMPGTSRTIKYSGSYNPNGNSYLAVYGVVT

RNPLIEYYIVENFGTYNPSSGGQKKGEVNVDGSVY

-continued

```
DIYVSTRVNAPSIDGNKTFQQYWSVRRNKRSSGSV

NTGAHFQAWKNVGLNLGTHDYQILAVEGYYSSGSA

SMTVSQ

SEQ ID No. 12:
TQPTTGTSGGYYFSFVVTDTPNSVTYTNGNGGQFS

MQWSGNGNHVGGKGWMPGTSRTIKYSGSYNPNGNS

YLAVYGVVTRNPLIEYYIVENFGTYNPSSGGQKKG

EVNVDGSVYDIYVSTRVNAPSIDGNKTFQQYWSVR

RNKRSSGSVNTGAHFQAWKNVGLNLGTHDYQILAV

EGYYSSGSASMTVSQ
```

Preferably, the xylanase is present in the feedstuff in range of about 500 XU/kg to about 16,000 XU/kg feed, more preferably about 750 XU/kg feed to about 8000 XU/kg feed, and even more preferably about 1000 XU/kg feed to about 4000 XU/kg feed In one embodiment the xylanase is present in the feedstuff at more than about 500 XU/kg feed, suitably more than about 600 XU/kg feed, suitably more than about 700 XU/kg feed, suitably more than about 800 XU/kg feed, suitably more than about 900 XU/kg feed, suitably more than about 1000 XU/kg feed.

In one embodiment the xylanase is present in the feedstuff at less than about 16,000 XU/kg feed, suitably less than about 8000 XU/kg feed, suitably less than about 7000 XU/kg feed, suitably less than about 6000 XU/kg feed, suitably less than about 5000 XU/kg feed, suitably less than about 4000 XU/kg feed.

Preferably, the xylanase is present in the feed additive composition in range of about 100 XU/g to about 320,000 XU/g composition, more preferably about 300 XU/g composition to about 160,000 XU/g composition, and even more preferably about 500 XU/g composition to about 50,000 XU/g composition, and even more preferably about 500 XU/g composition to about 40,000 XU/g composition.

In one embodiment the xylanase is present in the feed additive composition at more than about 100 XU/g composition, suitably more than about 200 XU/g composition, suitably more than about 300 XU/g composition, suitably more than about 400 XU/g composition, suitably more than about 500 XU/g composition.

In one embodiment the xylanase is present in the feed additive composition at less than about 320,000 XU/g composition, suitably less than about 160,000 XU/g composition, suitably less than about 50,000 XU/g composition, suitably less than about 40,000 XU/g composition, suitably less than about 30000 XU/g composition.

The xylanase activity can be expressed in xylanase units (XU) measured as taught in the "Xylanase Activity Assay (XU)" taught herein. See also Bailey, M. J. Biely, P. and Poutanen, K., Journal of Biotechnology, Volume 23, (3), May 1992, 257-270 the teaching of which is incorporated herein by reference.

In one embodiment suitably the enzyme is classified using the E.C. classification above, and the E.C. classification designates an enzyme having that activity when tested in the "Xylanase Activity Assay (XU)" taught herein for determining 1 XU.

In one embodiment the xylanase for use in the present invention may have xylanase activity as determined using the "Xylanase Activity Assay (ABX U/g)" taught herein.

Enzyme Activities and Assays

In one embodiment the feed additive composition may comprise a DFM in combination with a xylanase and a β-glucanase.

In one embodiment xylanase activity may be calculated using the "Xylanase Activity Assay (XU)" taught herein.

In another embodiment the β-glucanase activity may be calculated using the "β-glucanase Activity Assay (BGU)" taught herein.

Suitably, the DFM in combination with a xylanase and a β-glucanase may be dosed as set out in the table below:

|  | Dosage of constituent per g or per kg of final feedstuff |
|---|---|
| Xylanase (e.g. endo-1,4-β-d-xylanase) activity | 500-16000 XU/kg (preferably 2500-4000 XU/kg) |
| β-glucanase activity | 50-5000 BGU/kg (preferably 200-400 BGU/kg) |
| DFM | $1 \times 10^4$-$1 \times 10^9$ CFU/g (preferably $5 \times 10^4$-$5 \times 10^8$ CFU/g) |

The enzyme activity presented in units may be calculated for each enzyme as taught in the preceding sections.

In some embodiments the feed additive composition may comprise a DFM in combination with a xylanase, a β-glucanase and a further fibre degrading enzyme as taught herein.

Suitably the DFM, xylanase, β-glucanase and further fibre degrading enzyme may be dosed as set out in the table below:

|  | Dosage of constituent per g or per kg of final feedstuff |
|---|---|
| Xylanase (e.g. endo-1,4-β-d-xylanase) activity | 500-16000 (preferably 2500-4000 XU/kg) |
| β-glucanase activity | 100-2500 CMC U/kg (preferably 800-1000 CMC U/kg) |
| DFM | $1 \times 10^3$-$1 \times 10^9$ CFU/g (preferably $5 \times 10^4$-$5 \times 10^8$ CFU/g) |
| Further fibre degrading enzymes (e.g. of another xylanase and a beta-glucosidase) | >800 ABX U/kg (preferably >1200 ABX U/kg) >500 pNPG U/kg (preferably >800 pNPG U/kg) |

In one embodiment preferably the feedstuff comprises the following:
  a xylanase at at least 1000 XU/kg to 5000 XU/kg (suitably at at least 2000 XU/kg to 4500 XU/kg) of feed;
  a β-glucanase at at least 100 BGU/kg to 4000 BGU/kg (suitably at at least 150 BGU/kg to 3000 BGU/kg); and
  a DFM as taught herein at at least 50,000 CFU/g to 200,000 CFU/g (suitably at at least 70,000 CFU/g to 175,000 CFU/g) of feed.

In another embodiment preferably the feedstuff comprises the following:
  a xylanase at at least 1000 XU/kg to 5000 XU/kg (suitably at at least 2000 XU/kg to 4500 XU/kg) of feed;
  a β-glucanase at at least 100 BGU/kg to 4000 BGU/kg (suitably at at least 150 BGU/kg to 3000 BGU/kg); and
  a DFM as taught herein at at least 37,500 CFU/g to 100,000 CFU/g (suitably at at least 37,500 CFU/g to 75,000 CFU/g) of feed.

In another embodiment preferably the feedstuff comprises the following:

a xylanase at at least 1000 XU/kg to 5000 XU/kg (suitably at at least 2000 XU/kg to 4500 XU/kg) of feed;

a β-glucanase at at least 200-2000 CMC U/kg (suitably at least 500-1500 CMC U/kg) of feed;

a DFM as taught herein at at least 50,000 CFU/g to 200,000 CFU/g (suitably at at least 70,000 CFU/g to 175,000 CFU/g) of feed; and a further fibre degrading enzyme mix comprising at least 800-3500 ABX U/kg (suitably at least 1000-2750 ABX U/g) of feed and 500-3000 pNPG U/kg (suitably at least 600-2000 pNPG U/kg) of feed.

In another embodiment preferably the feedstuff comprises the following:

a xylanase at at least 1000 XU/kg to 5000 XU/kg (suitably at at least 2000 XU/kg to 4500 XU/kg) of feed;

a β-glucanase at at least 200-2000 CMC U/kg (suitably at least 500-1500 CMC U/kg) of feed;

a DFM as taught herein at at least 37,500 CFU/g to 100,000 CFU/g (suitably at at least 37,500 CFU/g to 75,000 CFU/g) of feed; and a further fibre degrading enzyme mix comprising at least 800-3500 ABX U/kg (suitably at least 1000-2750 ABX U/g) of feed and 500-3000 pNPG U/kg (suitably at least 600-2000 pNPG U/kg) of feed.

In one embodiment the DFM may be dosed in accordance with the number of units of xylanase present in the composition. In one embodiment the DFM may be dosed in the range from $6.25 \times 10^1$ CFU DFM: 1 XU enzyme to $2 \times 10^9$ CFU DFM: 1 XU enzyme; preferably in the range from $1.88 \times 10^4$ CFU DFM: 1 XU enzyme to $1.0 \times 10^7$ CFU DFM: 1 XU enzyme. The DFM taught herein may be used in combination with a xylanase and a β-glucanase.

In another embodiment the DFM taught herein may be used in combination with a xylanase, a β-glucanase and a further fibre degrading enzyme. In a preferred embodiment the further fibre degrading enzyme may be a β-glucosidase.

In one embodiment the xylanase for use in the present invention may have xylanase activity as determined using the "Xylanase Activity Assay (ABX U/g)" taught herein.

In a further embodiment the β-glucanase for use in the present invention may have β-glucanase activity as determined using the "β-glucanase Activity Assay (CMC U/g)" taught herein.

In a yet further embodiment the β-glucosidase for use in the present invention may have β-glucosidase activity as determined using the "β-glucosidase Activity Assay (pNPG U/g)" taught herein.

In one embodiment the DFM taught herein may be used in combination with a xylanase and a β-glucanase, wherein the xylanase and β-glucanase have the activities set out in the tables below:

|  | Range of activity in Units/g of each enzyme activity in the composition |
|---|---|
| Xylanase (e.g endo-1,4-β-d-xylanase) activity | 1500-6000 ABX U/g[1] |
| β-glucanase activity | 500-4000 CMC U/g[2] |
| Xylanase (e.g. endo-1,4-β-d-xylanase) activity | 2000-6000 ABX U/g[1] (preferably >3000 ABX u/g) |
| β-glucanase activity | 1000-3500 CMC U/g[2] (preferably about 2000-2600) CMC u/g) |

[1]One ABX unit is defined as the amount of enzyme required to generate 1 μmol of xylose reducing sugar equivalents per minute at 50° C. and pH 5.3.
[2]One CMC unit of activity liberates 1 μmol of reducing sugars (expressed as glucose equivalents) in one minute at 50° C. and pH 4.8.

In a preferred embodiment, the DFM taught herein may be used in combination with a xylanase, a β-glucanase and a β-glucosidase wherein the xylanase, β-glucanase and β-glucosidase have the activities set out in the tables below:

|  | Range of activity in Units/g of each enzyme activity in the composition |
|---|---|
| Xylanase (e.g. endo-1,4-β-d-xylanase) activity | 1500-6000 ABX U/g[1] |
| β-glucanase activity | 500-4000 CMC U/g[2] |
| β-glucosidase activity | 200-3500 pNPG U/g[3] |
| Xylanase (e.g. endo-1,4-β-d-xylanase) activity | 2000-6000 ABX U/g[1] (preferably >3000 ABX U/g) |
| β-glucanase activity | 1000-3500 CMC U/g[2] (preferably about 2000-2600) CMC U/g) |
| β-glucosidase activity | 300-3000 pNPG U/g[3] (preferably >2000 pNPG U/g) |

[1]One ABX unit is defined as the amount of enzyme required to generate 1 μmol of xylose reducing sugar equivalents per minute at 50° C. and pH 5.3.
[2]One CMC unit of activity liberates 1 μmol of reducing sugars (expressed as glucose equivalents) in one minute at 50° C. and pH 4.8.
[3]One pNPG unit denotes 1 μmol of nitro-phenol liberated from para-nitrophenyl-B-D-glucopyranoside per minute at 50° C. and pH 4.8.

In one embodiment the xylanase and β-glucanase for use in the present invention may comprise (or consist essentially of, or consist of) more than about 3000 ABX u/g of xylanase activity and about 2000-2600 CMC u/g of β-glucanase activity, respectively.

Suitably the xylanase, β-glucanase and β-glucosidase for use in the present invention may comprise (or consist essentially of, or consist of) more than about 3000 ABX u/g of xylanase activity, about 2000-2600 CMC u/g of β-glucanase activity and more than about 2000 pNPG u/g of β-glucosidase activity, respectively.

In one embodiment the xylanase for use in the present invention may comprise (or consist essentially of, or consist of) at least 2000 ABX u/g xylanase activity (suitably at least 2500 ABX u/g activity, suitably at least 3000 ABX u/g activity) as determined using the "Xylanase Activity Assay (ABX U/g)".

Suitably, the xylanase for use in the present invention may comprise (or consist essentially of, or consist of) about 2000 to about 5000 ABX u/g xylanase activity (suitably at least about 2500 to about 4000 ABX u/g activity, suitably at least about 3000 to about 4000 ABX u/g activity) as determined using the "Xylanase Activity Assay (ABX U/g)".

In another embodiment the β-glucanase for use in the present invention may comprise (or consist essentially of, or consist of) at least 1000 CMC u/g β-glucanase activity (suitably at least 1500 CMC u/g activity, suitably at least 2000 CMC u/g activity) as determined using the "β-glucanase Activity Assay (CMC U/g)".

Suitably, the β-glucanase for use in the present invention may comprise (or consist essentially of, or consist of) about 600 to about 4000 CMC u/g β-glucanase activity (suitably at least about 1000 to about 3000 CMC u/g activity, suitably at least about 1500 to about 2600 CMC u/g activity) as determined using the "β-glucanase Activity Assay (CMC U/g)".

In a further embodiment the β-glucosidase for use in the present invention may comprise (or consist essentially of or consist of) at least 300 pNPG u/g β-glucosidase activity (suitably at least 500 pNPG u/g activity, suitably at least 1000 pNPG u/g activity or suitably at least 2000 pNPG u/g activity) as determined using the "β-glucosidase Activity Assay (pNPG U/g)".

Suitably, the β-glucosidase for use in the present invention may comprise (or consist essentially of, or consist of) about 200 to about 4000 pNPG u/g β-glucosidase activity (suitably at least about 300 to about 3000 pNPG u/g activity, suitably at least about 1000 to about 3000 pNPG u/g activity or suitably at least about 2000 to about 3000 pNPG u/g activity) as determined using the "β-glucosidase Activity Assay (pNPG U/g)".

Suitably, the DFM taught herein may be used in combination with a xylanase and a β-glucanase comprising (or consisting essentially of or consisting of) at least 2000 ABX u/g xylanase activity (suitably at least 2500 ABX u/g activity, suitably at least 3000 ABX u/g activity) as determined using the "Xylanase Activity Assay (ABX U/g)"; and at least 1000 CMC u/g β-glucanase activity (suitably at least 1500 CMC u/g activity, suitably at least 2000 CMC u/g activity) as determined using the "β-glucanase Activity Assay (CMC U/g)".

Suitably, the DFM taught herein may be used in combination with a xylanase, a β-glucanase and a β-glucosidase comprising (or consisting essentially of, or consisting of) at least 2000 ABX u/g xylanase activity (suitably at least 2500 ABX u/g activity, suitably at least 3000 ABX u/g activity) as determined using the "Xylanase Activity Assay (ABX U/g)"; and at least 1000 CMC u/g β-glucanase activity (suitably at least 1500 CMC u/g activity, suitably at least 2000 CMC u/g activity) as determined using the "β-glucanase Activity Assay (CMC U/g)"; and at least 300 pNPG u/g β-glucosidase activity (suitably at least 500 pNPG u/g activity, suitably at least 1000 pNPG u/g activity or suitably at least 2000 pNPG u/g activity) as determined using the "β-glucosidase Activity Assay (pNPG U/g)".

In one embodiment the DFM taught herein may be used in combination with a xylanase and a β-glucanase comprising (or consisting essentially of, or consisting of) about 2000 to about 5000 ABX u/g xylanase activity (suitably at least about 2500 to about 4000 ABX u/g activity, suitably at least about 3000 to about 4000 ABX u/g activity) as determined using the "Xylanase Activity Assay (ABX U/g)"; and about 600 to about 4000 CMC u/g β-glucanase activity (suitably at least about 1000 to about 3000 CMC u/g activity, suitably at least about 1500 to about 2600 CMC u/g activity) as determined using the "β-glucanase Activity Assay (CMC U/g)".

Suitably, the DFM taught herein may be used in combination with a xylanase, a β-glucanase and a β-glucosidase comprising (or consisting essentially of, or consisting of) about 2000 to about 5000 ABX u/g xylanase activity (suitably at least about 2500 to about 4000 ABX u/g activity, suitably at least about 3000 to about 4000 ABX u/g activity) as determined using the "Xylanase Activity Assay (ABX U/g)"; about 600 to about 4000 CMC u/g β-glucanase activity (suitably at least about 1000 to about 3000 CMC u/g activity, suitably at least about 1500 to about 2600 CMC u/g activity) as determined using the "β-glucanase Activity Assay (CMC U/g)"; and about 200 to about 4000 pNPG u/g β-glucosidase activity (suitably at least about 300 to about 3000 pNPG u/g activity, suitably at least about 1000 to about 3000 pNPG u/g activity or suitably at least about 2000 to about 3000 pNPG u/g activity) as determined using the "β-glucosidase Activity Assay (pNPG U/g)".

"Xylanase Activity Assay (XU)"

The xylanase activity can be expressed in xylanase units (XU) measured at pH 5.0 with AZCL-arabinoxylan (azurine-crosslinked wheat arabinoxylan, Xylazyme 100 mg tablets, Megazyme) as substrate. Hydrolysis by endo-(1-4)-ß-D-xylanase (xylanase) produces water soluble dyed fragments, and the rate of release of these (increase in absorbance at 590 nm) can be related directly to enzyme activity. The xylanase units (XU) are determined relatively to an enzyme standard (Danisco Xylanase, available from Danisco Animal Nutrition) at standard reaction conditions, which are 40° C., 10 min reaction time in McIlvaine buffer, pH 5.0.

The xylanase activity of the standard enzyme is determined as amount of released reducing sugar end groups from an oat-spelt-xylan substrate per min at pH 5.3 and 50° C. The reducing sugar end groups react with 3, 5-Dinitrosalicylic acid and formation of the reaction product can be measured as increase in absorbance at 540 nm. The enzyme activity is quantified relative to a xylose standard curve (reducing sugar equivalents). One xylanase unit (XU) is the amount of standard enzyme that releases 0.5 µmol of reducing sugar equivalents per min at pH 5.3 and 50° C.

"Xylanase Activity Assay (Abx U/g)"

The xylanase activity can be expressed in acid birchwood xylanase units (ABX U) measured at pH 5.3 with birchwood 4-O methyl glucuronoxylan as substrate. Pipette 1.8 ml of 1% birchwood 4-O methyl glucuronoxylan substrate solution into each test tube. Incubate for 10-minutes, allowing to equilibrate at 50° C. Pipette 0.2 ml of enzyme dilution using positive displacement pipettes or equivalent. Vortex to mix. Incubate each sample at 50° C. for exactly 5 minutes. Add 3 ml of 1% 3,5 nitrosalicylic acid sodium salt (DNS) solution and mix. Cover the tops of the test tubes with caps to prevent evaporation. Place test tubes in a boiling bath for exactly 5 minutes. Cool test tubes for 10 minutes in ice/water bath. Incubate test tube for minutes at room temperature. Transfer test tube contents to cuvettes and measure at 540 nm against deionised water. Correct the absorbance for background colour by subtracting the corresponding enzyme blank. The enzyme activity is quantified relative to a xylose standard curve (reducing sugar equivalents).

One ABX unit is defined as the amount of enzyme required to generate 1 µmol of xylose reducing sugar equivalents per minute at 50° C. and pH 5.3.

"β-Glucanase Activity Assay (CMC U/g)"

The β-glucanase activity can be expressed in CMC units measured at pH 4.8 with carboxylmethyl cellulose sodium salt (CMC) as substrate. Pipette 1 ml of 1% carboxylmethyl cellulose sodium salt (CMC) solution (prepared with 0.05M sodium acetate buffer) into sample and blank tubes. Incubate tubes in a 50° C. water bath for 10 minutes. Pipette 1 ml of enzyme dilution at 15 second intervals to the sample tubes. Mix tubes after each addition. After 10 minute, add 3 ml of 1% 3,5 dinitrosalicylic acid sodium salt (DNS) in the same order and timing as the enzyme addition to the sample tubes. Add 3 ml of DNS to the sample blank tubes. After adding the DNS remove the test tubes to another rack not in the 50° C. water bath. Add 1 ml of diluted enzyme to the corresponding sample blank. Cap the tubes and boil for exactly 5 minutes. Remove from the 100° C. water bath and place in an ice bath for 10 minutes. Leave at room temperature for 10-15 minutes. Transfer to 3 ml cuvettes. Using the reagent blank to zero the spectrophotometer, each sample is read at 540 nm against de-ionised water. The enzyme activity is quantified relative to a glucose standard curve (reducing sugar equivalents). One CMC unit of activity liberates 1 μmol of reducing sugars (expressed as glucose equivalents) in one minute at 50° C. and pH 4.8.

"β-Glucanase Activity Assay (BGU)"

The beta-glucanase activity can be expressed in beta-glucanase units (BGU) measured at pH with AZCL-glucan (azurine-cross linked barley β-glucan, Glucazyme 100 mg tablets, Megazyme) as substrate. Hydrolysis by beta-glucanase produces soluble dyed fragments, and the rate of release of these (increase in absorbance at 590 nm) can be related directly to enzyme activity. The beta-glucanase units (BGU) are determined relatively to an enzyme standard (Multifect BGL, available from Danisco Animal Nutrition) at standard reaction conditions, which are 50° C., 10 min reaction time in 0.1 M acetate buffer, pH 5.0.

The beta-glucanase activity of the standard enzyme is determined as amount of released reducing sugar end groups from a barley glucan substrate per min at pH 5.0 and 50° C. The reducing sugar end groups react with 3,5-Dinitrosalicylic acid and formation of the reaction product can be measured as an increase in absorbance at 540 nm. The enzyme activity is quantified relative to a glucose standard curve (reducing sugar equivalents). One beta-glucanase unit (BGU) is the amount of standard enzyme that releases 2.4 μmol of reducing sugar equivalents per min at pH 5.0 and 50° C.

"μ-Glucosidase Activity Assay (pNPG U/g)"

The β-glucosidase activity can be expressed in pNPG units measured at pH 4.8 with para-nitrophenyl-B-D-glucopyranoside (pNPG) as substrate. Pipette 1 ml of 3% nitrophenyl-beta-D-glucopyranoside (pNPG) solution (prepared with 0.05M sodium acetate buffer) into duplicate test tubes for each sample and control. Place into 50° C. water bath for 5 minutes. Add 200 μl of control or sample to their respective duplicate tubes at intervals of 15-30 seconds. To the reagent blank tube, add 200 μl of sodium acetate buffer. Vortex each tube after addition of sample. Let the tubes incubate for exactly 10 minutes. After the 10 minutes incubation, add 500 μl of 1M sodium carbonate solution to stop the reaction. Vortex each tube after the addition and place the tube in a rack outside of the water bath. Add 10 ml of milli-Q water to each tube and vortex to mix. Using the reagent blank to zero the spectrophotometer, the concentration of the 4-nitrophenol is measured by reading each sample at 400 nm.

One pNPG unit denotes 1 μmol of nitro-phenol liberated from para-nitrophenyl-B-D-glucopyranoside per minute at 50° C. and pH 4.8.

Advantages

The interaction of DFMs with the xylanase and the β-glucanase (and optionally at least one further fibre degrading enzyme) is complicated and without wishing to be bound by theory, it is very surprising that we can see an increase in the production of short chain fatty acids in the GIT of animals.

The combination of the specific DFMs taught herein with at least one xylanase and at least one β-glucanase (and optionally at least one further fibre degrading enzyme) has been found to be particularly advantageous in feedstuffs and/or in a subject which is fed a feedstuff which is high in fibrous by-products (e.g. from the biofuel and milling industries).

It has been surprisingly found that the nutritional value and digestibility of feedstuffs comprising substantial quantities (sometimes 30-60%) of fibrous by-products (having a high content of non-starch polysaccharides, e.g. fibre) can be significantly improved, as can the performance and weight gain of a subject fed such feedstuffs.

One advantage of the present invention is the improvement of feed conversion ratio (FCR) observed by using the combination of the present invention.

Without wishing to be bound in theory the degradation of dietary material derived from plant cell wall particles which is high in non-starch polysaccharides (NSP) by xylanases can be optimized for improved animal performance when combining xylanase (e.g. endo-1,4-β-d-xylanase) with one or more β-glucanase (and optionally in combination with one or more further fibre degrading enzymes (e.g. a cellobiohydrolase (E.C. 3.2.1.176 and E.C. 3.2.1.91), a β-glucosidase (E.C. 3.2.1.21), a β-xylosidase (E.C. 3.2.1.37), a feruloyl esterase (E.C. 3.1.1.73), an α-arabinofuranosidase (E.C. 3.2.1.55), a pectinase (e.g. an endopolygalacturonase (E.C. 3.2.1.15), an exopolygalacturonase (E.C. 3.2.1.67) or a pectate lyase (E.C. 4.2.2.2)), or combinations thereof)) and one or more specific direct fed-microbials (DFMs) selected for their capacity to produce enzymes and/or their capacity of producing Short Chain Fatty Acids (SCFA) from NSP fraction pentoses in anaerobic conditions and/or their capacity to promote endogenous populations of fibrolytic microflora in a subject's GIT and/or their capacity to degrade C5-sugars.

The reason why this combination improves performance is that the solubilisation of fibre, specifically hemicellulose, from the diet is maximized in the gastro intestinal tract (GIT) of the animals. This solubilisation of hemicellulose would not always be sufficient to increase performance because C5-sugars released are not an efficient source of energy for animals when they are absorbed (Savory C. J. Br. J. Nut. 1992, 67: 103-114), but they are a more efficient source of energy when converted into short chain fatty acids (SOFA) either by microorganisms in the GIT or by DFMs.

Therefore the energy value from plant products (e.g. wheat, corn, oats, barley and cereals co-products (by-products) or mixed grain diet readily accessible for monogastrics) can be optimized by combining xylanase (e.g. endo-1,4-β-d-xylanase) and β-glucanase (and optionally at least one other fibre degrading enzyme (including but not limited to a cellobiohydrolase (E.C. 3.2.1.176 and E.C. 3.2.1.91), a β-glucosidase (E.C. 3.2.1.21), a β-xylosidase (E.C. 3.2.1.37), a feruloyl esterase (E.C. 3.1.1.73), an α-arabinofuranosidase (E.C. 3.2.1.55), a pectinase (e.g. an endopolygalacturonase (E.C. 3.2.1.15), an exopolygalacturonase (E.C. 3.2.1.67) or a pectate lyase (E.C. 4.2.2.2)), or combinations thereof)) and specific DFMs that can produce SCFAs from NSP fraction pentoses in anaerobic conditions and/or that can modulate the microbial populations in the GIT to increase SOFA production from the sugars released and/or that can utilise C-5 sugars. The DFMs may adapt their metabolism to synergistically increase the fibre hydrolysis in combination with xylanase and β-glucanase (and optionally at least one further fibre degrading enzyme). Using DFMs that can produce (fibrolytic) enzymes can provide additional benefits and maximize the benefits of the added enzymes.

Specific DFMs selected for their enzymatic activities can be considered as a glycan-driven bacterial food chain. The specifically selected DFMs taught herein may preferentially utilize dietary fibres, a trait that allows them to carry out the initial glycan digestion steps to liberate shorter, more soluble polysaccharides for other bacteria, e.g. other endogenous GIT microflora. The specific DFMs have been selected for their metabolism which adjusts according to the glycans released by enzymes (e.g. xylanase and β-glucanase (and optionally at least one further fibre degrading enzyme)) to improve the efficacy of the enzymes taught herein and the DFM(s) combination compared to use of a combination of enzymes alone or the use of DFM(s) alone.

Without wishing to be bound by theory, in the present invention dietary material derived from plant cell wall particles which is rich in source-specific glycans, such as cellulose, hemicellulose and pectin (plant material) or glycosaminoglycans enter the distal gut in particulate forms that are attacked by the specific DFMs glycan degraders which are capable of directly binding to these insoluble particles and digesting their glycan components. After this initial degradation of glycan-containing particles, more-soluble glycan fragments can be digested by secondary glycan degraders present in the caecum, which contribute to the liberated pool of short-chain fatty acid (SOFA) fermentation products that is derived from both types of degraders. As SCFAs arise from carbohydrate fermentation and/or protein fermentation and deamination by the indigenous anaerobic microflora in the GIT, SOFA concentration can be an index of the anaerobic-organism population. SOFA may actually provide a number of benefits to the host animal, acting as metabolic fuel for intestine, muscle, kidney, heart, liver and brain tissue, and also affording bacteriostatic and bacteriocidal properties against organisms such as *Salmonella* and *E. coli*.

The nutritional value of fibre in non-ruminants can mainly be derived through short chain fatty acids (SOFA) production via fermentation of solubilized or degraded fibres by effective fibre degrading enzymes (e.g. xylanases and β-glucanase and/or a further fibre degrading enzyme as taught herein). Feed xylanase alone is not enough to use fibrous ingredients in animal (especially non-ruminant) diets. A large array of chemical characteristics exists among plant-based feed ingredients. Enzyme application depends on the characteristics of the plant (feed) material. By way of example only, in wheat grain arabinoxylans predominates, however in wheat middlings (a co-product (by-product) of wheat milling), the content of β-glucan increases from 8 $g^{-1}$ DM (in grain) to an excess of 26 g $kg^{-1}$ DM. An enzyme matrix containing a complex of xylanase and β-glucanase (and optionally at least one further fibre degrading enzyme) can improve the nutritional value of feedstuffs high in co-product(s) (by-product(s)) based diets.

SCFAs have different energy values and some can serve as precursors of glucose and some can contribute to the maintenance of intestinal integrity and health. The inventors have found that the specific combinations taught herein preferentially move the fermentation process in an animal's GIT towards the production of more valuable/useful SOFA.

Without wishing to be bound by theory, the present inventors have found that NSPs can be effectively degraded by a combination of a DFM according to the present invention and a xylanase and a β-glucanase (and optionally at least one further fibre degrading enzyme). In addition, it has been found that this specific combination releases C-5 sugars which usually have only marginal nutritional value to the animal. However, using combinations as claimed herein it is possible to have microorganisms in the GIT (either the DFM of the present invention) or endogenous fibrolytic microflora (which are stimulated by the combinations (of DFM) of the present invention) convert these C-5 sugars into useful and nutritionally valuable components, namely short chain fatty acids. These short chain fatty acids can be utilised by the animal. Thus the system improves the nutritional value of a feedstuff for an animal.

Advantageously, the combination of a direct fed microbial, a xylanase and a β-glucanase (and optionally at least one further fibre degrading enzyme) as taught herein surprisingly increases fibre degradation in a feed additive composition, premix, feed or feedstuff, which leads to improved performance of a subject. In particular, the combination of the present invention improves digestibility of a raw material in a feed resulting in an increase in nutrient bioavailability (e.g. nutrient digestibility) and metabolizable energy therein.

Formulation of the DFM with the Enzymes

The DFM of the present invention and the enzymes may be formulated in any suitable way to ensure that the formulation comprises viable DFMs and active enzymes.

In one embodiment the DFM and enzymes may be formulated as a dry powder or a granule. The dry powder or granules may be prepared by means known to those skilled in the art, such as in a microingredients mixer.

For some embodiments the DFM and/or the enzyme(s) may be coated, for example encapsulated. Suitably the DFM and enzymes may be formulated within the same coating or encapsulated within the same capsule. Alternatively one or two or three or four of the enzymes may be formulated within the same coating or encapsulated within the same capsule and the DFM could be formulated in a coating separate to the one or more or all of the enzymes. In some embodiments, such as where the DFM is capable of producing endospores, the DFM may be provided without any coating. In such circumstances, the DFM endospores may be simply admixed with one or two or three or four enzymes. In the latter case, the enzymes may be coated, e.g. encapsulated, for instance one or more or all of the enzymes may be coated, e.g. encapsulated. The enzymes may be encapsulated as mixtures (i.e. comprising one or more, two or more, three or more or all) of enzymes or they may be encapsulated separately, e.g. as single enzymes. In one preferred embodiment all four enzymes may be coated, e.g. encapsulated, together.

In one embodiment the coating protects the enzymes from heat and may be considered a thermoprotectant.

In one embodiment the feed additive composition is formulated to a dry powder or granules as described in WO2007/044968 (referred to as TPT granules) incorporated herein by reference. In some embodiments the DFM (e.g. DFM endospores for example) may be diluted using a diluent, such as starch powder, lime stone or the like.

In another embodiment the feed additive composition may be formulated by applying, e.g. spraying, the enzyme(s) onto a carrier substrate, such as ground wheat for example.

In one embodiment the feed additive composition according to the present invention may be formulated as a premix. By way of example only the premix may comprise one or more feed components, such as one or more minerals and/or one or more vitamins.

In one embodiment the DFM and/or enzymes for use in the present invention are formulated with at least one physiologically acceptable carrier selected from at least one of maltodextrin, limestone (calcium carbonate), cyclodextrin, wheat or a wheat component, sucrose, starch, $Na_2SO_4$, Talc, PVA, sorbitol, benzoate, sorbiate, glycerol, sucrose, propylene glycol, 1,3-propane diol, glucose, parabens, sodium chloride, citrate, acetate, phosphate, calcium, metabisulfite, formate and mixtures thereof.

Packaging

In one embodiment the feed additive composition and/or premix and/or feed or feedstuff according to the present invention is packaged.

In one preferred embodiment the feed additive composition and/or premix and/or feed or feedstuff is packaged in a bag, such as a paper bag.

In an alternative embodiment the feed additive composition and/or premix and/or feed or feedstuff may be sealed in a container. Any suitable container may be used.

By-Products

The animal feed industry has seen an increased feeding of by-products, e.g. from biofuel processing, to animals (raising this form of animal feed from 0-10% to the current extremes of 30-60%). These diet cost savings have been a great opportunity for industry to save on feed input costs, but come with a set of challenges as well. The by-products are often high fibre (e.g. at least approximately 40% fibre) products. Consequently the inclusion of high-fibre by-product (e.g. DDGS) can have negative impact on animal growth performance and carcass characteristics. In addition to the negative effects on animal growth and carcass quality, alterations in nutrient digestibility have implications for manure (e.g. swine-manure) handling, storage and decomposition.

The term "by-product" as used herein means any fibrous plant material, e.g. one which comprises at least approximately 20% or 30% fibre).

In one embodiment the term by-product means any by-product of a high fibre feed material.

In one embodiment the by-product as referred to herein may be selected from one or more of the following products: corn germ meal, corn bran, Hominy feed, corn gluten feed, Distillers Dried Grain Solubles (DDGS), Distillers Dried Grain (DDG), gluten meal, wheat shorts, wheat middlings or combinations thereof.

In one embodiment the feedstuff of the present invention comprises a fibrous by-product such as corn germ meal, corn bran, Hominy feed, corn gluten feed, Distillers Dried Grain Solubles (DDGS), Distillers Dried Grain (DDG), gluten meal, wheat shorts, wheat middlings or combinations thereof.

In one embodiment the subject to which the DFM, xylanase and β-glucanase (and optionally at least one further fibre degrading enzyme) combination of the present invention or feed additive composition of the present invention is administered, is also fed a feedstuff comprising a fibrous by-product such as corn germ meal, corn bran, Hominy feed, corn gluten feed, Distillers Dried Grain Solubles (DDGS), Distillers Dried Grain (DDG), gluten meal, wheat shorts, wheat middlings or combinations thereof.

Breakdown or Degradation

The enzyme (or composition comprising the enzyme) of the present invention or as disclosed herein may be used to breakdown (degrade) insoluble arabinoxylan (AXinsol) or soluble arabinoxylan (AXsol) or combinations thereof, or degradation products of AXinsol. The term "breakdown" or "degrade" in synonymous with hydrolyses.

Non-Starch Polysaccharides (NSPs)

A major part of common vegetable feed ingredients consists of carbohydrates, making carbohydrates a crucial factor in animal production. Beside well digestible nutrients, such as starch and sugars, the carbohydrate fraction of vegetable origin includes indigestible (fibrous) components, such as cellulose, hemicellulose, pectins, beta-glucans and lignin.

All of these poorly digestible components, excluding lignin, are classified as a group referred to herein as non-starch polysaccharides (NSPs). The NSP fraction is well known for the anti-nutritional effects it can exert.

In one embodiment the term fibre may be used interchangeably with the term NSPs.

Within the group of NSP, hemicellulose itself is a heterogenous subgroup predominantly made up of xylans, arabinans, galatans, glucans and mannans. Arabinoxylan is the principal NSP-fraction in several of the most important feed raw materials, including wheat and corn.

Arabinoxylan (AX)

The term "arabinoxylans" (AX) as used herein means a polysaccharide consisting of a xylan backbone (1,4-linked xylose units) with L-arabinofuranose (L-arabinose in its 5-atom ring form) attached randomly by $1\alpha \rightarrow 2$ and/or $1\alpha \rightarrow 3$ linkages to the xylose units throughout the chain. Arabinoxylan is a hemicellulose found in both the primary and secondary cell walls of plants. Arabinoxylan can be found in the bran of grains such as wheat, maize (corn), rye, and barley.

Arabinoxylan (AX) is found in close association with the plant cell wall, where it acts as a glue linking various building blocks of the plant cell wall and tissue, give it both structural strength and rigidity.

Since xylose and arabinose (the constituents of arabinoxylans) are both pentoses, arabinoxylans are usually classified as pentosans.

AX is the principal Non Starch Polysaccharide (NSP)-fraction in several of the most important feed raw material, including wheat and corn.

Its abundance, location within vegetable material and molecular structure cause AX to have a severe, negative impact on feed digestibility, effectively reducing the nutritional value of the raw materials in which it is present. This makes AX an important anti-nutritional factor, reducing animal production efficiency.

AXs can also hold substantial amounts of water (which can be referred to as their water holding capacity)—this can cause soluble arabinoxylans to result in (high) viscosity—which is a disadvantage in many applications.

Water Insoluble Arabinoxylan (AXinsol)

Water-insoluble arabinoxylan (AXinsol) also known as water-unextractable arabinoxylan (WU-AX) constitutes a significant proportion of the dry matter of plant material.

In wheat AXinsol can account for 6.3% of the dry matter.

In wheat bran and wheat DDGS AXinsol can account for about 20.8% or 13.4% of the dry matter (w/w).

In rye AXinsol can account for 5.5% of the dry matter.

In corn AXinsol can account for 5.1% of the dry matter.

In corn DDGS AXinsol can account for 12.6% of the dry matter.

AXinsol causes nutrient entrapment in feed. Large quantities of well digestible nutrients such as starch and proteins remain either enclosed in clusters of cell wall material or bound to side chains of the AX. These entrapped nutrients will not be available for digestion and subsequent absorption in the small intestine.

Water-Soluble Arabinoxylan (AXsol)

Water-soluble arabinoxylan (AXsol) also known as water extractable arabinoxylan (WE-AX) can cause problems in biofuel production and/or malting and/or brewing and/or in feed as they can cause increased viscosity due to the water-binding capacity of AXsol.

In feed AXsol can have an anti-nutritional effect particularly in monogastrics as they cause a considerable increase of the viscosity of the intestinal content, caused by the extraordinary water-binding capacity of AXsol. The increase viscosity can affect feed digestion and nutrient use as it can prevent proper mixing of feed with digestive enzymes and bile salts and/or it slows down nutrient availability and absorption and/or it stimulates fermentation in the hindgut.

In wheat AXsol can account for 1.8% of the dry matter. In wheat bran and wheat DDGS AXsol can account for about 1.1% or 4.9% of the dry matter (w/w).

In rye AXsol can account for 3.4% of the dry matter.

In barley AXsol can account for 0.4-0.8% of the dry matter.

In corn AXsol can account for 0.1% of the dry matter. In corn DDGS AXinsol can account for of the dry matter.

In addition, however, to the amount of AXsol present in plant material, when a xylanase solubilises AXinsol in the plant material this can release pentosans and/or oligomers which contribute to AXsol content of the plant material.

One significant advantage of some of the xylanases disclosed herein is that they have the ability to both solubilise AXinsol as well as to rapidly and efficiently breakdown the solubilised oligomers and/or pentosans thus the enzymes are able to solubilise AXinsol without increasing viscosity and/or decreasing viscosity.

A breakdown of AXsol can decrease viscosity.

A breakdown of AXsol can release nutrients.

Viscosity

The present invention can be used to reduce viscosity in any process where the water-binding capacity of AXsol causes an undesirable increase in viscosity.

The present invention relates to reducing viscosity by breaking down (degrading) AXsol or by breaking down (degrading) the polymers and/or oligomers produced by solubilising AXinsol. In the present invention a reduction in viscosity can be calculated by comparing one sample comprising the xylanase of the present invention (or taught herein) compared with another comparable sample without the xylanase of the present invention (or taught herein).

Comparing the viscosity reduction profiles of the xylanase of the present invention with those of the market benchmark xylanases demonstrates the enzyme performance. The aim is to improve enzyme performance compared to the market benchmark. The benchmark enzymes for the individual applications are provided in the examples below In one embodiment of the present invention the xylanases taught herein are viscosity reducers.

Feed or Feedstuff

The enzyme or feed additive composition of the present invention may be used as—or in the preparation of—a feed.

The term "feed" is used synonymously herein with "feedstuff".

In one embodiment the feedstuff of the present invention comprises high fibre feed material and/or at least one by-product of the at least one high fibre feed material such as corn germ meal, corn bran, Hominy feed, corn gluten feed, Distillers Dried Grain Solubles (DDGS), Distillers Dried Grain (DDG), gluten meal, wheat shorts, wheat middlings or combinations thereof.

In one embodiment the subject to which the DFM, xylanase and β-glucanase combination (optionally in combination a further fibre degrading enzyme) of the present invention or feed additive composition of the present invention is administered, is also fed a feedstuff comprising a high fibre feed material and/or at least one by-product of the at least one high fibre feed material such as corn germ meal, corn bran, Hominy feed, corn gluten feed, Distillers Dried Grain Solubles (DDGS), Distillers Dried Grain (DDG), gluten meal, wheat shorts, wheat middlings or combinations thereof.

Suitably, in one embodiment the cereal component of a poultry subject's diet can be either wheat or barley with rye, wheat middlings, wheat bran, oats, oats hulls whilst vegetable components can be soybean meal with or without other protein ingredients such as canola, rape seed meal, etc. provided that the diet will contain wheat-barley as the main ingredients and formulated to meet the nutrient requirements of the birds being fed.

The feed according to the present invention may be in the form of a solution or as a solid—depending on the use and/or the mode of application and/or the mode of administration.

When used as—or in the preparation of—a feed—such as functional feed—the enzyme or composition of the present invention may be used in conjunction with one or more of: a nutritionally acceptable carrier, a nutritionally acceptable diluent, a nutritionally acceptable excipient, a nutritionally acceptable adjuvant, a nutritionally active ingredient.

In a preferred embodiment the enzyme or feed additive composition of the present invention is admixed with a feed component to form a feedstuff.

The term "feed component" as used herein means all or part of the feedstuff. Part of the feedstuff may mean one constituent of the feedstuff or more than one constituent of the feedstuff, e.g. 2 or 3 or 4. In one embodiment the term "feed component" encompasses a premix or premix constituents.

Preferably the feed may be a fodder, or a premix thereof, a compound feed, or a premix thereof. In one embodiment the feed additive composition according to the present invention may be admixed with a compound feed, a compound feed component or to a premix of a compound feed or to a fodder, a fodder component, or a premix of a fodder.

The term fodder as used herein means any food which is provided to an animal (rather than the animal having to forage for it themselves). Fodder encompasses plants that have been cut.

The term fodder includes silage, compressed and pelleted feeds, oils and mixed rations, and also sprouted grains and legumes.

Fodder may be obtained from one or more of the plants selected from: corn (maize), alfalfa (Lucerne), barley, birdsfoot trefoil, brassicas, Chau moellier, kale, rapeseed (canola), rutabaga (swede), turnip, clover, alsike clover, red clover, subterranean clover, white clover, fescue, brome, millet, oats, sorghum, soybeans, trees (pollard tree shoots for tree-hay), wheat, and legumes.

The term "compound feed" means a commercial feed in the form of a meal, a pellet, nuts, cake or a crumble. Compound feeds may be blended from various raw materials and additives. These blends are formulated according to the specific requirements of the target animal.

Compound feeds can be complete feeds that provide all the daily required nutrients, concentrates that provide a part of the ration (protein, energy) or supplements that only provide additional micronutrients, such as minerals and vitamins.

The main ingredients used in compound feed are the feed grains, which include corn, wheat, wheat bran, soybeans, sorghum, oats, and barley.

Suitably a premix as referred to herein may be a composition composed of microingredients such as vitamins, minerals, chemical preservatives, antibiotics, fermentation products, and other essential ingredients. Premixes are usually compositions suitable for blending into commercial rations.

Any feedstuff of the present invention may comprise one or more feed materials selected from the group comprising a) cereals, such as small grains (e.g., wheat, barley, rye, oats, triticale and combinations thereof) and/or large grains such as maize or sorghum; b) by products from cereals, such as corn germ meal, corn bran, Hominy feed, corn gluten feed, Distillers Dried Grain Solubles (DDGS), Distillers Dried Grain (DDG), gluten meal, wheat shorts, wheat middlings or combinations thereof; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; e) minerals and vitamins.

In one embodiment the feedstuff comprises or consists of corn, DDGS (such as cDDGS), wheat, wheat bran or a combination thereof.

In one embodiment the feed component may be corn, DDGS (e.g. cDDGS), wheat, wheat bran or a combination thereof.

In one embodiment the feedstuff comprises or consists of corn, DDGS (such as cDDGS) or a combination thereof.

In one embodiment a feed component may be corn, DDGS (such as corn DDGS (cDDGS)) or a combination thereof.

A feedstuff of the present invention may contain at least 30%, at least 40%, at least 50% or at least 60% by weight corn and soybean meal or corn and full fat soy, or wheat meal or sunflower meal.

A feedstuff of the present invention may contain between about 5 to about 40% corn DDGS.

For poultry—the feedstuff on average may contain between about 7 to 12% corn DDGS. For swine (pigs)—the feedstuff may contain on average 5 to 40% corn DDGS.

A feedstuff of the present invention may contain corn as a single grain, in which case the feedstuff may comprise between about 35% to about 85% corn.

In feedstuffs comprising mixed grains, e.g. comprising corn and wheat for example, the feedstuff may comprise at least 10% corn.

In addition or in the alternative, a feedstuff of the present invention may comprise at least one high fibre feed material and/or at least one by-product of the at least one high fibre feed material to provide a high fibre feedstuff. Examples of high fibre feed materials include: wheat, barley, rye, oats, by products from cereals, such as corn gluten meal, wet-cake, Distillers Dried Grain (DDG), Distillers Dried Grain with Solubles (DDGS), wheat bran, wheat middlings, wheat shorts, rice bran, rice hulls, oat hulls, palm kernel, and citrus pulp. Some protein sources may also be regarded as high fibre: protein obtained from sources such as sunflower, lupin, fava beans and cotton.

In one embodiment the feedstuff of the present invention comprises at least one high fibre material and/or at least one by-product of the at least one high fibre feed material selected from the group consisting of Distillers Dried Grain with Solubles (DDGS)—particularly corn DDGS (cDDGS), wet-cake, Distillers Dried Grain (DDG)—particularly corn DDG (cDDG), wheat bran, and wheat for example.

In one embodiment the feedstuff of the present invention comprises at least one high fibre material and/or at least one by-product of the at least one high fibre feed material selected from the group consisting of Distillers Dried Grain Solubles (DDGS)—particularly cDDGS, wheat bran, and wheat for example.

In the present invention the feed may be one or more of the following: a compound feed and premix, including pellets, nuts or (cattle) cake; a crop or crop residue: corn, soybeans, sorghum, oats, barley, copra, chaff, sugar beet waste; fish meal; meat and bone meal; molasses; oil cake and press cake; oligosaccharides; conserved forage plants: silage; seaweed; seeds and grains, either whole or prepared by crushing, milling etc.; sprouted grains and legumes; yeast extract.

The term feed in the present invention also encompasses in some embodiments pet food. A pet food is plant or animal material intended for consumption by pets, such as dog food or cat food. Pet food, such as dog and cat food, may be either in a dry form, such as kibble for dogs, or wet canned form. Cat food may contain the amino acid taurine.

The term feed in the present invention also encompasses in some embodiments fish food. A fish food normally contains macro nutrients, trace elements and vitamins necessary to keep captive fish in good health. Fish food may be in the form of a flake, pellet or tablet. Pelleted forms, some of which sink rapidly, are often used for larger fish or bottom feeding species. Some fish foods also contain additives, such as beta carotene or sex hormones, to artificially enhance the color of ornamental fish.

The term feed in the present invention also encompasses in some embodiment bird food. Bird food includes food that is used both in birdfeeders and to feed pet birds. Typically bird food comprises of a variety of seeds, but may also encompass suet (beef or mutton fat).

As used herein the term "contacted" refers to the indirect or direct application of the enzyme (or composition comprising the enzyme) of the present invention to the product (e.g. the feed). Examples of the application methods which may be used, include, but are not limited to, treating the product in a material comprising the feed additive composition, direct application by mixing the feed additive composition with the product, spraying the feed additive composition onto the product surface or dipping the product into a preparation of the feed additive composition.

In one embodiment the feed additive composition of the present invention is preferably admixed with the product (e.g. feedstuff). Alternatively, the feed additive composition may be included in the emulsion or raw ingredients of a feedstuff.

For some applications, it is important that the composition is made available on or to the surface of a product to be affected/treated. This allows the composition to impart one or more of the following favourable characteristics: performance benefits.

The enzyme (or composition comprising the enzyme) of the present invention may be applied to intersperse, coat and/or impregnate a product (e.g. feedstuff or raw ingredients of a feedstuff) with a controlled amount of said enzyme.

Suitably the feed additive composition may be simply administered to the subject at the same time as feeding the animal a feedstuff.

Preferably, the enzyme (or composition comprising the enzyme) of the present invention will be thermally stable to heat treatment up to about 70° C.; up to about 85° C.; or up to about 95° C. The heat treatment may be performed for up to about 1 minute; up to about 5 minutes; up to about 10 minutes; up to about 30 minutes; up to about 60 minutes. The term thermally stable means that at least about 75% of the enzyme that was present/active in the additive before heating to the specified temperature is still present/active after it cools to room temperature. Preferably, at least about 80% of the enzyme that is present and active in the additive before heating to the specified temperature is still present and active after it cools to room temperature.

In a particularly preferred embodiment the enzyme (or composition comprising the enzyme) of the present invention is homogenized to produce a powder.

In an alternative preferred embodiment, the enzyme (or composition comprising the enzyme) of the present invention is formulated to granules as described in WO2007/044968 (referred to as TPT granules) incorporated herein by reference.

In another preferred embodiment when the feed additive composition is formulated into granules the granules comprise a hydrated barrier salt coated over the protein core. The advantage of such salt coating is improved thermo-tolerance, improved storage stability and protection against other feed additives otherwise having adverse effect on the enzyme.

Preferably, the salt used for the salt coating has a water activity greater than 0.25 or constant humidity greater than 60% at 20° C.

Preferably, the salt coating comprises a $Na_2SO_4$.

The method of preparing an enzyme (or composition comprising the enzyme) of the present invention may also comprise the further step of pelleting the powder. The powder may be mixed with other components known in the art. The powder, or mixture comprising the powder, may be forced through a die and the resulting strands are cut into suitable pellets of variable length.

Optionally, the pelleting step may include a steam treatment, or conditioning stage, prior to formation of the pellets. The mixture comprising the powder may be placed in a conditioner, e.g. a mixer with steam injection. The mixture is heated in the conditioner up to a specified temperature, such as from 60-100° C., typical temperatures would be 70° C., 80° C., 85° C., 90° C. or 95° C. The residence time can be variable from seconds to minutes and even hours. Such as 5 seconds, 10 seconds, 15 seconds, 30 seconds, 1 minutes 2 minutes., 5 minutes, 10 minutes, 15 minutes, 30 minutes and 1 hour.

It will be understood that the enzyme (or composition comprising the enzyme) of the present invention is suitable for addition to any appropriate feed material.

It will be understood by the skilled person that different animals require different feedstuffs, and even the same animal may require different feedstuffs, depending upon the purpose for which the animal is reared.

Optionally, the feedstuff may also contain additional minerals such as, for example, calcium and/or additional vitamins.

Preferably, the feedstuff is a corn soybean meal mix.

In one embodiment, preferably the feed is not pet food.

In another aspect there is provided a method for producing a feedstuff. Feedstuff is typically produced in feed mills in which raw materials are first ground to a suitable particle size and then mixed with appropriate additives. The feedstuff may then be produced as a mash or pellets; the later typically involves a method by which the temperature is raised to a target level and then the feed is passed through a die to produce pellets of a particular size. The pellets are allowed to cool. Subsequently liquid additives such as fat and enzyme may be added. Production of feedstuff may also involve an additional step that includes extrusion or expansion prior to pelleting—in particular by suitable techniques that may include at least the use of steam.

The feedstuff may be a feedstuff for a monogastric animal, such as poultry (for example, broiler, layer, broiler breeders, turkey, duck, geese, water fowl), swine (all age categories), a pet (for example dogs, cats) or fish, preferably the feedstuff is for poultry.

The feedstuff may be a feedstuff for a monogastric animal, such as poultry (for example, broiler, layer, broiler breeders, turkey, duck, geese, water fowl), swine (all age categories), a pet (for example dogs, cats) or fish, preferably the feedstuff is for poultry.

In one embodiment the feedstuff is not for a layer.

By way of example only a feedstuff for chickens, e.g. broiler chickens may be comprises of one or more of the ingredients listed in the table below, for example in the % ages given in the table below:

| Ingredients | Starter (%) | Finisher (%) |
|---|---|---|
| Maize | 46.2 | 46.7 |
| Wheat Middlings | 6.7 | 10.0 |
| Maize DDGS | 7.0 | 7.0 |
| Soyabean Meal 48% CP | 32.8 | 26.2 |
| Animal/Vegetable Fat blend | 3.0 | 5.8 |
| L-Lysine HCl | 0.3 | 0.3 |
| DL-methionine | 0.3 | 0.3 |
| L-threonine | 0.1 | 0.1 |
| Salt | 0.3 | 0.4 |
| Limestone | 1.1 | 1.1 |
| Dicalcium Phosphate | 1.2 | 1.2 |
| Poultry Vitamins and Micro-minerals | 0.3 | 0.3 |

By way of example only the diet specification for chickens, such as broiler chickens, may be as set out in the Table below:

| Diet specification | | |
|---|---|---|
| Crude Protein (%) | 23.00 | 20.40 |
| Metabolizable Energy Poultry (kcal/kg) | 2950 | 3100 |
| Calcium (%) | 0.85 | 0.85 |
| Available Phosphorus (%) | 0.38 | 0.38 |
| Sodium (%) | 0.18 | 0.19 |
| Dig. Lysine (%) | 1.21 | 1.07 |
| Dig. Methionine (%) | 0.62 | 0.57 |
| Dig. Methionine + Cysteine (%) | 0.86 | 0.78 |
| Dig. Threonine (%) | 0.76 | 0.68 |

By way of example only a feedstuff laying hens may be comprises of one or more of the ingredients listed in the table below, for example in the % ages given in the table below:

| Ingredient | Laying phase (%) |
|---|---|
| Maize | 10.0 |
| Wheat | 53.6 |
| Maize DDGS | 5.0 |
| Soybean Meal 48% CP | 14.9 |
| Wheat Middlings | 3.0 |
| Soybean Oil | 1.8 |
| L-Lysine HCl | 0.2 |
| DL-methionine | 0.2 |
| L-threonine | 0.1 |
| Salt | 0.3 |
| Dicalcium Phosphate | 1.6 |
| Limestone | 8.9 |
| Poultry Vitamins and Micro-minerals | 0.6 |

By way of example only the diet specification for laying hens may be as set out in the Table below:

| Diet specification | |
| --- | --- |
| Crude Protein (%) | 16.10 |
| Metabolizable Energy Poultry (kcal/kg) | 2700 |
| Lysine (%) | 0.85 |
| Methionine (%) | 0.42 |
| Methionine + Cysteine (%) | 0.71 |
| Threonine (%) | 0.60 |
| Calcium (%) | 3.85 |
| Available Phosphorus (%) | 0.42 |
| Sodium (%) | 0.16 |

By way of example only a feedstuff for turkeys may be comprises of one or more of the ingredients listed in the table below, for example in the % ages given in the table below:

| Ingredient | Phase 1 (%) | Phase 2 (%) | Phase 3 (%) | Phase 4 (%) |
| --- | --- | --- | --- | --- |
| Wheat | 33.6 | 42.3 | 52.4 | 61.6 |
| Maize DDGS | 7.0 | 7.0 | 7.0 | 7.0 |
| Soyabean Meal 48% CP | 44.6 | 36.6 | 27.2 | 19.2 |
| Rapeseed Meal | 4.0 | 4.0 | 4.0 | 4.0 |
| Soyabean Oil | 4.4 | 4.2 | 3.9 | 3.6 |
| L-Lysine HCl | 0.5 | 0.5 | 0.4 | 0.4 |
| DL-methionine | 0.4 | 0.4 | 0.3 | 0.2 |
| L-threonine | 0.2 | 0.2 | 0.1 | 0.1 |
| Salt | 0.3 | 0.3 | 0.3 | 0.3 |
| Limestone | 1.0 | 1.1 | 1.1 | 1.0 |
| Dicalcium Phosphate | 3.5 | 3.0 | 2.7 | 2.0 |
| Poultry Vitamins and Micro-minerals | 0.4 | 0.4 | 0.4 | 0.4 |

By way of example only the diet specification for turkeys may be as set out in the Table below:

| Diet specification | | | | |
| --- | --- | --- | --- | --- |
| Crude Protein (%) | 29.35 | 26.37 | 22.93 | 20.00 |
| Metabolizable Energy Poultry (kcal/kg) | 2.850 | 2.900 | 2.950 | 3.001 |
| Calcium (%) | 1.43 | 1.33 | 1.22 | 1.02 |
| Available Phosphorus (%) | 0.80 | 0.71 | 0.65 | 0.53 |
| Sodium (%) | 0.16 | 0.17 | 0.17 | 0.17 |
| Dig. Lysine (%) | 1.77 | 1.53 | 1.27 | 1.04 |
| Dig. Methionine (%) | 0.79 | 0.71 | 0.62 | 0.48 |
| Dig. Methionine + Cysteine (%) | 1.12 | 1.02 | 0.90 | 0.74 |
| Dig. Threonine (%) | 1.03 | 0.89 | 0.73 | 0.59 |

By way of example only a feedstuff for piglets may be comprises of one or more of the ingredients listed in the table below, for example in the % ages given in the table below:

| Ingredient | Phase 1 (%) | Phase 2 (%) |
| --- | --- | --- |
| Maize | 20.0 | 7.0 |
| Wheat | 25.9 | 46.6 |
| Rye | 4.0 | 10.0 |
| Wheat middlings | 4.0 | 4.0 |
| Maize DDGS | 6.0 | 8.0 |
| Soyabean Meal 48% CP | 25.7 | 19.9 |
| Dried Whey | 10.0 | 0.0 |
| Soyabean Oil | 1.0 | 0.7 |
| L-Lysine HCl | 0.4 | 0.5 |
| DL-methionine | 0.2 | 0.2 |
| L-threonine | 0.1 | 0.2 |
| L-tryptophan | 0.03 | 0.04 |
| Limestone | 0.6 | 0.7 |
| Dicalcium Phosphate | 1.6 | 1.6 |
| Swine Vitamins and Micro-minerals | 0.2 | 0.2 |
| Salt | 0.2 | 0.4 |

By way of example only the diet specification for piglets may be as set out in the Table below:

| Diet specification | | |
| --- | --- | --- |
| Crude Protein (%) | 21.50 | 20.00 |
| Swine Digestible Energy (kcal/kg) | 3380 | 3320 |
| Swine Net Energy (kcal/kg) | 2270 | 2230 |
| Calcium (%) | 0.80 | 0.75 |
| Digestible Phosphorus (%) | 0.40 | 0.35 |
| Sodium (%) | 0.20 | 0.20 |
| Dig. Lysine (%) | 1.23 | 1.14 |
| Dig. Methionine (%) | 0.49 | 0.44 |
| Dig. Methionine + Cysteine (%) | 0.74 | 0.68 |
| Dig. Threonine (%) | 0.80 | 0.74 |

By way of example only a feedstuff for grower/finisher pigs may be comprises of one or more of the ingredients listed in the table below, for example in the % ages given in the table below:

| Ingredient | Grower/Finisher (%) |
| --- | --- |
| Maize | 27.5 |
| Soyabean Meal 48% CP | 15.4 |
| Maize DDGS | 20.0 |
| Wheat bran | 11.1 |
| Rice bran | 12.0 |
| Canola seed meal | 10.0 |
| Limestone | 1.6 |
| Dicalcium phosphate | 0.01 |
| Salt | 0.4 |
| Swine Vitamins and Micro-minerals | 0.3 |
| Lysine-HCl | 0.2 |
| Vegetable oil | 0.5 |

By way of example only the diet specification for grower/finisher pigs may be as set out in the Table below:

| Diet specification | |
| --- | --- |
| Crude Protein (%) | 22.60 |
| Swine Metabolizable Energy (kcal/kg) | 3030 |
| Calcium (%) | 0.75 |
| Available Phosphorus (%) | 0.29 |
| Digestible Lysine (%) | 1.01 |
| Dig. Methionine + Cysteine (%) | 0.73 |
| Digestible Threonine (%) | 0.66 |

Wet-Cake, Distillers Dried Grains (DDG) and Distillers Dried Grain Solubles (DDGS)

Wet-cake, Distillers Dried Grains and Distillers Dried Grains with Solubles are products obtained after the removal of ethyl alcohol by distillation from yeast fermentation of a grain or a grain mixture by methods employed in the grain distilling industry.

Stillage coming from the distillation (e.g. comprising water, remainings of the grain, yeast cells etc.) is separated into a "solid" part and a liquid part.

The solid part is called "wet-cake" and can be used as animal feed as such.

The liquid part is (partially) evaporated into a syrup (solubles).

When the wet-cake is dried it is Distillers Dried Grains (DDG).

When the wet-cake is dried together with the syrup (solubles) it is Distillers Dried Grans with Solubles (DDGS).

Wet-cake may be used in dairy operations and beef cattle feedlots.

The dried DDGS may be used in livestock, e.g. dairy, beef and swine) feeds and poultry feeds.

Corn DDGS is a very good protein source for dairy cows.

Corn Gluten Meal

In one aspect, the by-product of corn may be corn gluten meal (CGM).

CGM is a powdery by-product of the corn milling inductry. CGM has utility in, for example, animal feed. It can be used as an inexpensive protein source for feed such as pet food, livestock feed and poultry feed. It is an especially good source of the amino acid cysteine,-but must be balanced with other proteins for lysine.

Feed Additive Composition

The feed additive composition of the present invention and/or the feedstuff comprising same may be used in any suitable form.

The feed additive composition of the present invention may be used in the form of solid or liquid preparations or alternatives thereof. Examples of solid preparations include powders, pastes, boluses, capsules, pellets, tablets, dusts, and granules which may be wettable, spray-dried or freeze-dried. Examples of liquid preparations include, but are not limited to, aqueous, organic or aqueous-organic solutions, suspensions and emulsions.

In some applications, the feed additive compositions of the present invention may be mixed with feed or administered in the drinking water.

In one aspect the present invention relates to a method of preparing a feed additive composition, comprising admixing a xylanase, a β-glucanase (and optionally at least one further fibre degrading enzyme) and a DFM as taught herein with a feed acceptable carrier, diluent or excipient, and (optionally) packaging.

Premix

The feedstuff and/or feed additive composition may be combined with at least one mineral and/or at least one vitamin. The compositions thus derived may be referred to herein as a premix.

Forms

The feed additive composition of the present invention and other components and/or the feedstuff comprising same may be used in any suitable form.

The feed additive composition of the present invention may be used in the form of solid or liquid preparations or alternatives thereof. Examples of solid preparations include powders, pastes, boluses, capsules, pellets, tablets, dusts, and granules which may be wettable, spray-dried or freeze-dried. Examples of liquid preparations include, but are not limited to, aqueous, organic or aqueous-organic solutions, suspensions and emulsions.

In some applications, DFM or feed additive compositions of the present invention may be mixed with feed or administered in the drinking water. In one embodiment the dosage range for inclusion into water is about $1 \times 10^3$ CFU/animal/day to about $1 \times 10^{10}$ CFU/animal/day, and more preferably about $1 \times 10^7$ CFU/animal/day.

Suitable examples of forms include one or more of: powders, pastes, boluses, pellets, tablets, pills, capsules, ovules, solutions or suspensions, which may contain flavouring or colouring agents, for immediate-, delayed-, modified-, sustained-, pulsed- or controlled-release applications.

By way of example, if the composition of the present invention is used in a solid, e.g. pelleted form, it may also contain one or more of: excipients such as microcrystalline cellulose, lactose, sodium citrate, calcium carbonate, dibasic calcium phosphate and glycine; disintegrants such as starch (preferably corn, potato or tapioca starch), sodium starch glycollate, croscarmellose sodium and certain complex silicates; granulation binders such as polyvinylpyrrolidone, hydroxypropylmethylcellulose (HPMC), hydroxypropylcellulose (HPC), sucrose, gelatin and acacia; lubricating agents such as magnesium stearate, stearic acid, glyceryl behenate and talc may be included.

Examples of nutritionally acceptable carriers for use in preparing the forms include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

Preferred excipients for the forms include lactose, starch, a cellulose, milk sugar or high molecular weight polyethylene glycols.

For aqueous suspensions and/or elixirs, the composition of the present invention may be combined with various sweetening or flavouring agents, colouring matter or dyes, with emulsifying and/or suspending agents and with diluents such as water, propylene glycol and glycerin, and combinations thereof.

Non-hydroscopic whey is often used as a carrier for DFMs (particularly bacterial DFMs) and is a good medium to initiate growth.

Bacterial DFM containing pastes may be formulated with vegetable oil and inert gelling ingredients.

Fungal products may be formulated with grain by-products as carriers.

In one embodiment preferably the feed additive composition according to the present invention is not in the form of a microparticle system, such as the microparticle system taught in WO2005/123034.

Dosing

The DFM and/or feed additive composition according to the present invention may be designed for one-time dosing or may be designed for feeding on a daily basis.

The optimum amount of the composition (and each component therein) to be used in the combination of the present invention will depend on the product to be treated and/or the method of contacting the product with the composition and/or the intended use for the same. The amount of DFM and enzymes used in the compositions should be a sufficient amount to be effective and to remain sufficiently effective in improving the performance of the animal fed feed products containing said composition. This length of time for effectiveness should extend up to at least the time of utilisation of the product (e.g. feed additive composition or feed containing same).

Combination with Other Components

The DFM and enzyme(s) for use in the present invention may be used in combination with other components. Thus, the present invention also relates to combinations. The DFM in combination with the xylanase and a β-glucanase (and optionally at least one further fibre degrading enzyme) may be referred to herein as "the feed additive composition of the present invention".

In a preferred embodiment "the feed additive composition of the present invention" may comprise (or consist essentially of, or consist of) DFM in combination with the xylanase and a β-glucanase and a further fibre degrading enzyme as taught herein (e.g. suitably at least two, suitably at least three further fibre degrading enzymes).

In a further preferred embodiment "the feed additive composition of the present invention" may comprise (or consist essentially of, or consist of) DFM in combination with the xylanase and a β-glucanase and a further fibre degrading enzyme as taught herein (e.g. suitably at least four, suitably at least five further fibre degrading enzymes).

The combination of the present invention comprises the feed additive composition of the present invention (or one or more of the constituents thereof) and another component which is suitable for animal consumption and is capable of providing a medical or physiological benefit to the consumer.

In one embodiment preferably the "another component" is not a further enzyme or a further DFM.

The components may be prebiotics. Prebiotics are typically non-digestible carbohydrate (oligo- or polysaccharides) or a sugar alcohol which is not degraded or absorbed in the upper digestive tract. Known prebiotics used in commercial products and useful in accordance with the present invention include inulin (fructo-oligosaccharide, or FOS) and transgalacto-oligosaccharides (GOS or TOS). Suitable prebiotics include palatinoseoligosaccharide, soybean oligosaccharide, alginate, xanthan, pectin, locust bean gum (LBG), inulin, guar gum, galacto-oligosaccharide (GOS), fructo-oligosaccharide (FOS), non-degradable starch, lactosaccharose, lactulose, lactitol, maltitol, maltodextrin, polydextrose (i.e. Litesse®), lactitol, lactosucrose, soybean oligosaccharides, palatinose, isomalto-oligosaccharides, gluco-oligosaccharides and xylo-oligosaccharides.

In one embodiment the present invention relates to the combination of the feed additive composition according to the present invention (or one or more of the constituents thereof) with a prebiotic. In another embodiment the present invention relates to a feed additive composition comprising (or consisting essentially of or consisting of) a DFM in combination with a xylanase, a β-glucanase, an amylase, a phytase, a protease and a prebiotic.

The prebiotic may be administered simultaneously with (e.g. in admixture together with or delivered simultaneously by the same or different routes) or sequentially to (e.g. by the same or different routes) the feed additive composition (or constituents thereof) according to the present invention.

Other components of the combinations of the present invention include polydextrose, such as Litesse®, and/or a maltodextrin and/or lactitol. These other components may be optionally added to the feed additive composition to assist the drying process and help the survival of DFM.

Further examples of other suitable components include one or more of: thickeners, gelling agents, emulsifiers, binders, crystal modifiers, sweeteners (including artificial sweeteners), rheology modifiers, stabilisers, anti-oxidants, dyes, enzymes, carriers, vehicles, excipients, diluents, lubricating agents, flavouring agents, colouring matter, suspending agents, disintegrants, granulation binders etc. These other components may be natural. These other components may be prepared by use of chemical and/or enzymatic techniques.

In one embodiment the DFM and/or enzymes may be encapsulated. In one embodiment the feed additive composition and/or DFM and/or enzymes is/are formulated as a dry powder or granule as described in WO2007/044968 (referred to as TPT granules)—reference incorporated herein by reference.

In one preferred embodiment the DFM and/or enzymes for use in the present invention may be used in combination with one or more lipids.

For example, the DFM and/or enzymes for use in the present invention may be used in combination with one or more lipid micelles. The lipid micelle may be a simple lipid micelle or a complex lipid micelle.

The lipid micelle may be an aggregate of orientated molecules of amphipathic substances, such as a lipid and/or an oil.

As used herein the term "thickener or gelling agent" refers to a product that prevents separation by slowing or preventing the movement of particles, either droplets of immiscible liquids, air or insoluble solids. Thickening occurs when individual hydrated molecules cause an increase in viscosity, slowing the separation. Gelation occurs when the hydrated molecules link to form a three-dimensional network that traps the particles, thereby immobilising them.

The term "stabiliser" as used here is defined as an ingredient or combination of ingredients that keeps a product (e.g. a feed product) from changing over time.

The term "emulsifier" as used herein refers to an ingredient (e.g. a feed ingredient) that prevents the separation of emulsions. Emulsions are two immiscible substances, one present in droplet form, contained within the other. Emulsions can consist of oil-in-water, where the droplet or dispersed phase is oil and the continuous phase is water; or water-in-oil, where the water becomes the dispersed phase and the continuous phase is oil. Foams, which are gas-in-liquid, and suspensions, which are solid-in-liquid, can also be stabilised through the use of emulsifiers.

As used herein the term "binder" refers to an ingredient (e.g. a feed ingredient) that binds the product together through a physical or chemical reaction. During "gelation" for instance, water is absorbed, providing a binding effect. However, binders can absorb other liquids, such as oils, holding them within the product. In the context of the present invention binders would typically be used in solid or low-moisture products for instance baking products: pastries, doughnuts, bread and others.

"Carriers" or "vehicles" mean materials suitable for administration of the DFM and/or enzymes and include any such material known in the art such as, for example, any liquid, gel, solvent, liquid diluent, solubilizer, or the like, which is non-toxic and which does not interact with any components of the composition in a deleterious manner.

In one embodiment the feed additive composition, premix, feed or feedstuff of the present invention may be admixed with at least one physiologically acceptable carrier selected from at least one of maltodextrin, limestone (calcium carbonate), cyclodextrin, wheat or a wheat component, sucrose, starch, $Na_2SO_4$, Talc, PVA, sorbitol, benzoate, sorbiate, glycerol, sucrose, propylene glycol, 1,3-propane diol, glucose, parabens, sodium chloride, citrate, acetate, phosphate, calcium, metabisulfite, formate and mixtures thereof.

Examples of excipients include one or more of: microcrystalline cellulose and other celluloses, lactose, sodium citrate, calcium carbonate, dibasic calcium phosphate, glycine, starch, milk sugar and high molecular weight polyethylene glycols.

Examples of disintegrants include one or more of: starch (preferably corn, potato or tapioca starch), sodium starch glycollate, croscarmellose sodium and certain complex silicates.

Examples of granulation binders include one or more of: polyvinylpyrrolidone, hydroxypropylmethylcellulose (HPMC), hydroxypropylcellulose (HPC), sucrose, maltose, gelatin and acacia.

Examples of lubricating agents include one or more of: magnesium stearate, stearic acid, glyceryl behenate and talc.

Examples of diluents include one or more of: water, ethanol, propylene glycol and glycerin, and combinations thereof.

The other components may be used simultaneously (e.g. when they are in admixture together or even when they are delivered by different routes) or sequentially (e.g. they may be delivered by different routes).

Preferably, when the feed additive composition of the present invention is admixed with another component(s), the DFM remains viable.

In one embodiment preferably the feed additive composition according to the present invention does not comprise chromium or organic chromium In one embodiment preferably the feed additive according to the present invention does not contain sorbic acid.

Concentrates

The DFMs for use in the present invention may be in the form of concentrates. Typically these concentrates comprise a substantially high concentration of a DFM.

Feed additive compositions according to the present invention may have a content of viable cells (colony forming units, CFUs) which is in the range of at least $10^4$ CFU/g (suitably including at least $10^5$ CFU/g, such as at least $10^6$ CFU/g, e.g. at least $10^7$ CFU/g, at least $10^8$ CFU/g, such as at least $10^9$ CFU/g) to about $10^{10}$ CFU/g (or even about $10^{11}$ CFU/g or about $10^{12}$ CFU/g).

When the DFM is in the form of a concentrate the feed additive compositions according to the present invention may have a content of viable cells in the range of at least $10^9$ CFU/g to about $10^{12}$ CFU/g, preferably at least $10^{10}$ CFU/g to about $10^{12}$ CFU/g.

Powders, granules and liquid compositions in the form of concentrates may be diluted with water or resuspended in water or other suitable diluents, for example, an appropriate growth medium such as milk or mineral or vegetable oils, to give compositions ready for use.

The DFM or feed additive composition of the present invention or the combinations of the present invention in the form of concentrates may be prepared according to methods known in the art.

In one aspect of the present invention the enzymes or feed is contacted by a composition in a concentrated form.

The compositions of the present invention may be spray-dried or freeze-dried by methods known in the art.

Typical processes for making particles using a spray drying process involve a solid material which is dissolved in an appropriate solvent (e.g. a culture of a DFM in a fermentation medium). Alternatively, the material can be suspended or emulsified in a non-solvent to form a suspension or emulsion. Other ingredients (as discussed above) or components such as anti-microbial agents, stabilising agents, dyes and agents assisting with the drying process may optionally be added at this stage.

The solution then is atomised to form a fine mist of droplets. The droplets immediately enter a drying chamber where they contact a drying gas. The solvent is evaporated from the droplets into the drying gas to solidify the droplets, thereby forming particles. The particles are then separated from the drying gas and collected.

Subject

The term "subject", as used herein, means an animal that is to be or has been administered with a feed additive composition according to the present invention or a feedstuff comprising said feed additive composition according to the present invention.

The term "subject", as used herein, means an animal. Preferably, the subject is a mammal, bird, fish or crustacean including for example livestock or a domesticated animal (e.g. a pet). In one embodiment the "subject" is livestock.

The term "livestock", as used herein refers to any farmed animal. Preferably, livestock is one or more of cows or bulls (including calves), poultry, pigs (including piglets), poultry (including broilers, chickens and turkeys), birds, fish (including freshwater fish, such as salmon, cod, trout and carp, e.g. koi carp, and marine fish, such as sea bass), crustaceans (such as shrimps, mussels and scallops), horses (including race horses), sheep (including lambs).

In one embodiment the term livestock and/or poultry and/or chickens does not include egg layers.

In another embodiment the "subject" is a domesticated animal or pet or an animal maintained in a zoological environment.

The term "domesticated animal or pet or animal maintained in a zoological environment" as used herein refers to any relevant animal including canines (e.g. dogs), felines (e.g. cats), rodents (e.g. guinea pigs, rats, mice), birds, fish (including freshwater fish and marine fish), and horses.

Short Chain Fatty Acid (SCFA) Production

The term "short chain fatty acid" as used herein includes volatile fatty acids as well as lactic acid. In one embodiment the SCFA may be selected from the group consisting of: acetic acid, propionic acid, butyric acid, isobutyric acid, valeric acid, isovaleric acid, 2-methylbutyric acids and lactic acid, preferably propionic acid and/or butyric acid.

In one embodiment the SCFA may be butyric acid and/or propionic acid.

Short chain fatty acids (particularly volatile fatty acids, e.g. propionic acid and butyric acid, and lactic acid) may be analysed using the following method:

Chromatographic analysis of volatile fatty acids and lactic acid, e.g. SCFAs, to be performed from simulation samples with pivalic acid as internal standard as previously described (Ouwehand et al., 2009 Feb.; 101(3):367-75). Concentrations of acetic, propionic, butyric, isobutyric, valeric, isovaleric, 2-methylbutyric acids, and lactic acid are determined.

Performance

As used herein, "animal performance" may be determined by the feed efficiency and/or weight gain of the animal and/or by the feed conversion ratio and/or by the digestibility of a nutrient in a feed (e.g. amino acid digestibility) and/or digestible energy or metabolizable energy in a feed and/or by nitrogen retention.

Preferably "animal performance" is determined by feed efficiency and/or weight gain of the animal and/or by the feed conversion ratio.

By "improved animal performance" it is meant that there is increased feed efficiency, and/or increased weight gain and/or reduced feed conversion ratio and/or improved digestibility of nutrients or energy in a feed and/or by improved nitrogen retention resulting from the use of feed additive composition of the present invention in feed in comparison to feed which does not comprise said feed additive composition.

Preferably, by "improved animal performance" it is meant that there is increased feed efficiency and/or increased weight gain and/or reduced feed conversion ratio.

As used herein, the term "feed efficiency" refers to the amount of weight gain in an animal that occurs when the animal is fed ad-libitum or a specified amount of food during a period of time. By "increased feed efficiency" it is meant that the use of a feed additive composition according the present invention in feed results in an increased weight gain per unit of feed intake compared with an animal fed without said feed additive composition being present.

Feed Conversion Ratio (FCR)

As used herein, the term "feed conversion ratio" refers to the amount of feed fed to an animal to increase the weight of the animal by a specified amount.

An improved feed conversion ratio means a lower feed conversion ratio.

By "lower feed conversion ratio" or "improved feed conversion ratio" it is meant that the use of a feed additive composition in feed results in a lower amount of feed being required to be fed to an animal to increase the weight of the animal by a specified amount compared to the amount of feed required to increase the weight of the animal by the same amount when the feed does not comprise said feed additive composition.

Nutrient Digestibility

Nutrient digestibility as used herein means the fraction of a nutrient that disappears from the gastro-intestinal tract or a specified segment of the gastro-intestinal tract, e.g. the small intestine. Nutrient digestibility may be measured as the difference between what is administered to the subject and what comes out in the faeces of the subject, or between what is administered to the subject and what remains in the digesta on a specified segment of the gastro intestinal trace, e.g. the ileum.

Nutrient digestibility as used herein may be measured by the difference between the intake of a nutrient and the excreted nutrient by means of the total collection of excreta during a period of time; or with the use of an inert marker that is not absorbed by the animal, and allows the researcher calculating the amount of nutrient that disappeared in the entire gastro-intestinal tract or a segment of the gastro-intestinal tract. Such an inert marker may be titanium dioxide, chromic oxide or acid insoluble ash. Digestibility may be expressed as a percentage of the nutrient in the feed, or as mass units of digestible nutrient per mass units of nutrient in the feed. Nutrient digestibility as used herein encompasses starch digestibility, fat digestibility, protein digestibility, and amino acid digestibility.

Energy digestibility as used herein means the gross energy of the feed consumed minus the gross energy of the faeces or the gross energy of the feed consumed minus the gross energy of the remaining digesta on a specified segment of the gastro-intestinal tract of the animal, e.g. the ileum. Metabolizable energy as used herein refers to apparent metabolizable energy and means the gross energy of the feed consumed minus the gross energy contained in the faeces, urine, and gaseous products of digestion. Energy digestibility and metabolizable energy may be measured as the difference between the intake of gross energy and the gross energy excreted in the faeces or the digesta present in specified segment of the gastro-intestinal tract using the same methods to measure the digestibility of nutrients, with appropriate corrections for nitrogen excretion to calculate metabolizable energy of feed.

Nitrogen Retention

Nitrogen retention as used herein means as subject's ability to retain nitrogen from the diet as body mass. A negative nitrogen balance occurs when the excretion of nitrogen exceeds the daily intake and is often seen when the muscle is being lost. A positive nitrogen balance is often associated with muscle growth, particularly in growing animals.

Nitrogen retention may be measured as the difference between the intake of nitrogen and the excreted nitrogen by means of the total collection of excreta and urine during a period of time. It is understood that excreted nitrogen includes undigested protein from the feed, endogenous proteinaceous secretions, microbial protein, and urinary nitrogen.

Carcass Yield and Meat Yield

The term carcass yield as used herein means the amount of carcass as a proportion of the live body weight, after a commercial or experimental process of slaughter. The term carcass means the body of an animal that has been slaughtered for food, with the head, entrails, part of the limbs, and feathers or skin removed. The term meat yield as used herein means the amount of edible meat as a proportion of the live body weight, or the amount of a specified meat cut as a proportion of the live body weight.

Weight Gain

The present invention further provides a method of increasing weight gain in a subject, e.g. poultry or swine, comprising feeding said subject a feedstuff comprising a feed additive composition according to the present invention.

An "increased weight gain" refers to an animal having increased body weight on being fed feed comprising a feed additive composition compared with an animal being fed a feed without said feed additive composition being present.

Other Properties

In one embodiment the feed additive composition, feed, feedstuff or method according to the present invention may not modulate (e.g. improve) the immune response of the subject. In a further embodiment the feed additive composition, feed, feedstuff or method according to the present invention may not improve survival (e.g. reduce mortality) of the subject.

In a preferred embodiment the feed additive composition, feed, feedstuff or method according to the present invention may not modulate (e.g. improve) the immune response or improve survival (e.g. reduce mortality) of the subject.

Probiotic

For some applications, it is believed that the DFM in the composition of the present invention can exert a probiotic culture effect. It is also within the scope of the present invention to add to the composition of the present invention further probiotic and/or prebiotics.

Here, a prebiotic is:

"a non-digestible food ingredient that beneficially affects the host by selectively stimulating the growth and/or the activity of one or a limited number of beneficial bacteria".

The term "probiotic culture" as used herein defines live microorganisms (including bacteria or yeasts for example) which, when for example ingested or locally applied in sufficient numbers, beneficially affects the host organism, i.e. by conferring one or more demonstrable health benefits on the host organism. Probiotics may improve the microbial balance in one or more mucosal surfaces. For example, the mucosal surface may be the intestine, the urinary tract, the respiratory tract or the skin. Whilst there are no lower or upper limits for probiotic intake, it has been suggested that at least $10^6$-$10^{12}$, preferably at least $10^6$-$10^{10}$, preferably $10^8$-$10^9$, cfu as a daily dose will be effective to achieve the beneficial health effects in a subject.

Isolated

In one aspect, preferably the enzyme used in the present invention is in an isolated form. The term "isolated" means that the enzyme is at least substantially free from at least one other component with which the enzyme is naturally associated in nature and as found in nature. The enzyme of the present invention may be provided in a form that is substantially free of one or more contaminants with which the substance might otherwise be associated. Thus, for example it may be substantially free of one or more potentially contaminating polypeptides and/or nucleic acid molecules.

Purified

In one aspect, preferably the enzyme and/or DFM according to the present invention is in a purified form. The term "purified" means that the enzyme and/or DFM is present at a high level. The enzyme and/or DFM is desirably the predominant component present in a composition. Preferably, it is present at a level of at least about 90%, or at least about 95% or at least about 98%, said level being determined on a dry weight/dry weight basis with respect to the total composition under consideration.

It is envisaged within the scope of the present invention that the embodiments of the invention can be combined such that combinations of any of the features described herein are included within the scope of the present invention. In particular, it is envisaged within the scope of the present invention that any of the therapeutic effects of the bacteria may be exhibited concomitantly.

Amino Acid Sequences

The scope of the present invention also encompasses amino acid sequences of enzymes having the specific properties as defined herein.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The amino acid sequence may be prepared/isolated from a suitable source, or it may be made synthetically or it may be prepared by use of recombinant DNA techniques.

Preferably the amino acid sequence when relating to and when encompassed by the perse scope of the present invention is not a native enzyme. In this regard, the term "native enzyme" means an entire enzyme that is in its native environment and when it has been expressed by its native nucleotide sequence.

Sequence Identity or Sequence Homology

The present invention also encompasses the use of sequences having a degree of sequence identity or sequence homology with amino acid sequence(s) of a polypeptide having the specific properties defined herein or of any nucleotide sequence encoding such a polypeptide (hereinafter referred to as a "homologous sequence(s)"). Here, the term "homologue" means an entity having a certain homology with the subject amino acid sequences and the subject nucleotide sequences. Here, the term "homology" can be equated with "identity".

The homologous amino acid sequence and/or nucleotide sequence should provide and/or encode a polypeptide which retains the functional activity and/or enhances the activity of the enzyme.

The term "nucleotide sequence" in relation to the present invention includes genomic DNA, cDNA, synthetic DNA, and RNA. Preferably it means DNA, more preferably cDNA sequence coding for the present invention.

In the present context, in some embodiments a homologous sequence is taken to include an amino acid or a nucleotide sequence which may be at least 97% identical, preferably at least 98 or 99% identical to the subject sequence.

In some embodiments a homologous sequence is taken to include an amino acid or a nucleotide sequence which may be at least 85% identical, preferably at least 90 or 95% identical to the subject sequence.

Typically, the homologues will comprise the same active sites etc. as the subject amino acid sequence for instance. Although homology can also be considered in terms of similarity (i.e. amino acid residues having similar chemical properties/functions), in the context of the present invention it is preferred to express homology in terms of sequence identity.

In one embodiment, a homologous sequence is taken to include an amino acid sequence or nucleotide sequence which has one or several additions, deletions and/or substitutions compared with the subject sequence.

In one embodiment the present invention relates to a protein whose amino acid sequence is represented herein or a protein derived from this (parent) protein by substitution, deletion or addition of one or several amino acids, such as 2, 3, 4, 5, 6, 7, 8, 9 amino acids, or more amino acids, such as 10 or more than 10 amino acids in the amino acid sequence of the parent protein and having the activity of the parent protein.

Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology. However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons.

Calculation of maximum % homology therefore firstly requires the production of an optimal alignment, taking into consideration gap penalties. A suitable computer program for carrying out such an alignment is the Vector NTI (Invitrogen Corp.). Examples of software that can perform sequence comparisons include, but are not limited to, the BLAST package (see Ausubel et al 1999 Short Protocols in Molecular Biology, 4th Ed-Chapter 18), BLAST 2 (see FEMS Microbiol Lett 1999 174(2): 247-50; FEMS Microbiol Lett 1999 177(1): 187-8 and tatiana@ncbi.nlm.nih.gov), FASTA (Altschul et al 1990 J. Mol. Biol. 403-410) and AlignX for example. At least BLAST, BLAST 2 and FASTA are available for offline and online searching (see Ausubel et al 1999, pages 7-58 to 7-60).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. Vector NTI programs generally use either the public default values or a custom symbol comparison table if supplied (see user manual for further details). For some applications, it is preferred to use the default values for the Vector NTI package.

Alternatively, percentage homologies may be calculated using the multiple alignment feature in Vector NTI (Invitrogen Corp.), based on an algorithm, analogous to CLUSTAL (Higgins D G & Sharp P M (1988), Gene 73(1), 237-244).

Once the software has produced an optimal alignment, it is possible to calculate % homology, preferably % sequence identity. The software typically does this as part of the sequence comparison and generates a numerical result.

Should Gap Penalties be used when determining sequence identity, then preferably the following parameters are used for pairwise alignment:

| FOR BLAST | |
|---|---|
| GAP OPEN | 0 |
| GAP EXTENSION | 0 |

| FOR CLUSTAL | DNA | PROTEIN | |
|---|---|---|---|
| WORD SIZE | 2 | 1 | K triple |
| GAP PENALTY | 15 | 10 | |
| GAP EXTENSION | 6.66 | 0.1 | |

In one embodiment, CLUSTAL may be used with the gap penalty and gap extension set as defined above.

Suitably, the degree of identity with regard to an amino acid sequence is determined over at least 20 contiguous amino acid residues, preferably over at least 30 contiguous residues, preferably over at least 40 contiguous residues, preferably over at least 50 contiguous residues, preferably over at least 60 contiguous residues, preferably over at least 100 contiguous residues.

Suitably, the degree of identity with regard to amino acid sequence may be determined over the whole sequence taught herein.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
|---|---|---|
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I -phenylalanine*, L-allyl-glycine*, ß-alanine*, L-α-amino butyric acid*, L-γ-amino butyric acid*, L-α-amino isobutyric acid*, L-ε-amino caproic acid #, 7-amino heptanoic acid*, L-methionine sulfone #*, L-norleucine*, L-norvaline*, p-nitro-L-phenylalanine*, L-hydroxyproline #, L-thioproline*, methyl derivatives of phenylalanine (Phe) such as 4-methyl-Phe*, pentamethyl-Phe*, L-Phe (4-amino) #, L-Tyr (methyl)*, L-Phe (4-isopropyl)*, L-Tic (1,2,3,4-tetrahydroisoquinoline-3-carboxyl acid)*, L-diaminopropionic acid #and L-Phe (4-benzyl)*. The notation * has been utilised for the purpose of the discussion above (relating to homologous or non-homologous substitution), to indicate the hydrophobic nature of the derivative whereas #has been utilised to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Norwell D C, Trends Biotechnol. (1995) 13(4), 132-134.

In one embodiment the xylanase for use in the present invention may comprise a polypeptide sequence herein with a conservative substitution of at least one of the amino acids.

Suitably there may be at least 2 conservative substitutions, such as at least 3 or at least 4 or at least 5.

Suitably there may be less than 15 conservative substitutions, such as less than 12, less than 10, or less than 8 or less than 5.

EXAMPLES

Example 1: Responses of Broiler Chickens Fed Wheat-Based Diets Containing Xylanase, β-Glucanase and Direct Fed Microbials Material and Methods The use of animals and experimental protocol was approved by the Institutional Animal Experiment Committee. A diet was formulated to be balanced for energy and nutrients for young broiler chicks (0-21 days of life) (Table 1, Diet I). The cereal component of the diet was either wheat, barley, rye, wheat middlings, wheat bran or combinations thereof whilst the protein component was soybean meal and the source of fat was rapeseed oil. No synthetic antimicrobials or anti-coccidial drugs were included, and the diet was supplied as a mash. The basal diet was divided into portions and the respective enzymes and DFMs added to constitute experimental diets identified in Table 2.

Each supplement was provided in a premix and added to the mixer during diet preparation. Diets containing the DFM were mixed first and the mixer was flushed between each diet to prevent cross contamination. Samples were collected from each treatment diet from the beginning, middle, and end of each batch and blended together to confirm enzyme activities and DFM presence in feed before commencement of the animal trial. Additional samples from each treatment diet were retained and stored until required at −20° C.±2° C. for analysis.

Male broiler (Ross 308) chicks were obtained as day-olds from a commercial hatchery. The chicks were individually weighed and allocated to 32 brooder cages (8 chicks per cage) so that the average bird weight per cage was similar. The 4 dietary treatments (Table 2) were then randomly assigned to 8 cages each. On day 12, the birds were transferred to grower cages.

The space allocation per bird in brooder and grower cages was 530 and 640 $cm^2$, respectively. The brooder and grower cages were housed in environmentally controlled rooms. The temperature was maintained at 31° C. in the first week and then gradually reduced to 22° C. by the end of third week. The birds received 20 hours fluorescent illumination and, allowed free access to the diets and water. The diets were offered from d 0 to 21. Body weights were recorded at weekly intervals throughout the 21-d experimental period. Mortality was recorded daily. The data were analyzed using the GLM procedure of SAS.

TABLE 1

Diet composition of broiler wheat-basal diets (% as fed)

| Ingredients | Diet I | Diet II | Diet III |
|---|---|---|---|
| Wheat | 44.9 | 43.9 | 44.36 |
| Wheat middlings | 3.00 | 2.83 | — |
| Barley | 10.0 | 10.0 | — |
| Rye | — | 5.00 | — |
| Wheat bran | — | — | 22.8 |
| Soybean Meal | 30.9 | 29.3 | 23.9 |
| Fat | 5.89 | 4.25 | — |
| Rapeseed oil | — | — | 4.5 |
| L-Lysine HCl | 0.40 | 0.32 | 0.59 |
| DL-Methionine | 0.34 | 0.24 | 0.23 |
| L-Threonine | 0.19 | 0.10 | 0.25 |
| Sodium Bicarbonate | — | 0.20 | — |
| Salt | 0.17 | 0.23 | 0.36 |
| Limestone | 1.69 | 1.32 | 1.00 |
| Monocalcium Phosphate | 1.55 | 1.00 | 1.61 |
| Trace minerals/vitamins premix | 0.50 | 1.00 | 0.40 |
| Titanium dioxide | — | 0.30 | — |
| Calculated Provisions | | | |
| Crude protein, % | 22.1 | 21.8 | 21.8 |
| Metabolizable energy, MJ/kg | 12.7 | 11.60 | 11.63 |
| Calcium, % | 1.05 | 0.88 | 0.88 |
| Available Phosphorous, % | 0.50 | 0.38 | 0.38 |
| Digestible Lysine, % | 1.27 | 1.15 | 1.15 |
| Digestible Methionine % | 0.63 | 0.51 | 0.51 |

TABLE 2

Identification of treatments

| ID | Description[1] |
|---|---|
| 1 | Control, no additive |
| 2 | NC + Xylanase (2500 XU/kg) |
| 3 | NC + Xylanase (2500 XU/kg) + β-glucanase (200 BGU/kg) |
| 4 | NC + Xylanase (2500 XU/kg) + β-glucanase (200 BGU/kg) + DFM[2](7.5e+04) |

[1]The enzymes (xylanase (Danisco Xylanase an endo-1,4-β-D-xylanase (E.C. 3.2.1.8)) and β-glucanase Axtra ® XB) are commercial products supplied by Danisco Animal nutrition.
[2]A three-strain Bacillus based direct fed microbial, selected for the ability to secrete enzymes supplied by Danisco Animal nutritionas equal proportions of strains AGTP BS918 (NRRL B-50508), AGTP BS3BP5 (NRRL B-50510) and AGTP BS1013 (NRRL B-50509).

Results

TABLE 3

Effects of xylanase, β-glucanase and a bacillus based direct fed microbials on growth performance of a young broiler chick.

| | Body weight at 21 days, g | Body weight gain, g |
|---|---|---|
| 1 | 863.8b | 827.4b |
| 2 | 897.0ab | 860.4ab |
| 3 | 899.6ab | 863.4ab |
| 4 | 906.3a | 869.6a |
| Std. error | 16.98 | 16.92 |

N.B. Different letters following the values show statistical differences ($P \leq 0.10$) between values in that column Chicks fed combination of xylanase, a fibre degrading enzyme (β-glucanase) and a bacillus based DFM grew faster than control and numerically better than chicks fed enzymes only diets. The body weight at 21 days and the body weight gain was numerically better in chicks fed three way combinations of xylanase, β-glucanase and DFM relative to the control.

II. Nutrients and Energy Retention/Digestibility

Material and Methods

The use of animals and experimental protocol was approved by the Institutional Animal Experiment Committee. A wheat-barley based diet was formulated to be balanced for energy and nutrients for young broiler chicks (0-21 days of life) (Table 1, Diet II). Titanium dioxide was included at 0.30% to allow determination of dietary component retention. No synthetic antimicrobials or anti-coccidial drugs were included, and the diet was supplied as a mash. The basal diet was divided into portions and the respective enzymes and DFMs added to constitute experimental diets identified in Table 4. Each supplement was pre-mixed and the mixer was flushed to prevent cross contamination of treated diets. Samples were collected from each treatment diet from the beginning, middle, and end of each batch and blended together to confirm enzyme activities and DFM presence in feed before commencement of the animal trial. Additional samples from each treatment diet are retained and stored until required at −20° C.±2° C. for analysis.

TABLE 4

Identification of treatments

| ID | Description[1] |
|---|---|
| 1 | Control, no additive |
| 2 | NC + Xylanase (2500 XU/kg) |
| 3 | NC + Xylanase (2500 XU/kg) + β-glucanase (200 XBGU/kg) |
| 4 | NC + Xylanase (2500 XU/kg) + β-glucanase (200 BGU/kg) + DFM[2]((7.5e+04) |

[1]The enzymes (xylanase (Danisco Xylanase an endo-1,4-β-D-xylanase (E.C. 3.2.1.8)) and β-glucanase (Axtra ® XB)) are commercial products supplied by Danisco Animal nutrition.
[2]A three-strain Bacillus based direct fed microbials, selected for their ability to secrete enzymes supplied by Danisco Animal nutrition as equal proportions of strains AGTP BS918 (NRRL B-50508), AGTP BS3BP5 (NRRL B-50510) and AGTP BS1013 (NRRL B-50509).

The study involved a cage trial, which was conducted to obtain excreta samples for energy and nutrients digestibility measurements. Day-old male broiler chicks (Ross 308) were obtained from a commercial hatchery. The chicks were individually weighed upon arrival and stratified by body weight and allocated to 30 cages (five chicks per cage) so that the average bird weight per cage was similar. The four dietary treatments were then randomly assigned to six replicate cages. The trial was conducted from day 0 to 21 during which the birds had free access to their assigned dietary treatments and water. The brooder and room temperatures were set at 32 and 29° C., respectively, during the first week. Thereafter, heat supply in the brooder was switched off and room temperature was maintained at 29° C. throughout the experiment. Light was provided for 24 h throughout the experiment. On days 17, 18, 19 and 20, samples of excreta were collected and stored frozen at −20° C. for the determination of energy and nutrients retention/digestibility. Care was taken during the collection of excreta samples to avoid contamination from feathers and other foreign materials. Excreta samples were pooled within a cage mixed well using a blender and two representative samples per cage were taken. The samples were freeze-dried. Dried samples were ground to pass through a 0.5 mm sieve and stored in airtight plastic containers at −4° C. until chemical analyses. Samples of diets and excreta were analyzed for dry matter, crude protein (as nitrogen), gross energy, fat (as hexane extracts) and neutral detergent fibre according to AOAC official methods of analysis). Titanium (digestibility marker) was analyzed according to the procedures described by Lomer et al. (2000, Analyst 125:2339-2343). Retention/Digestibility was calculated using the standard procedures (Adeola, O. 2001. Digestion and balance techniques in pigs. Pages 903-916 in Swine Nutrition, 2nd ed. A. J. Lewis, and L. L. Southern, ed. CRC Press, Washington, DC). Data were analyzed using the General Linear Models procedure of SAS (2004).

Results

TABLE 5

Effects of xylanase, a fiber degrading enzyme and a bacillus based direct fed microbials on nutrients retention/digestibility and energy metabolizability in a young broiler chick.

| | Apparent retention/digestibility, % | | | | |
|---|---|---|---|---|---|
| Treatment | Dry matter | Crude protein | Fat | Neutral detergent fiber | ME, kcal/kg |
| 1 | 67.4d | 62.2c | 78.3c | 29.0c | 2875c |
| 2 | 71.2b | 64.7b | 81.5b | 37.1a | 3033b |
| 3 | 70.9c | 63.8bc | 82.9b | 33.1b | 3040b |
| 4 | 73.9a | 68.8a | 86.0a | 38.9a | 3154a |
| Std. error | 0.06 | 0.70 | 0.71 | 1.06 | 2.92 |

N.B. Different letters following the values show statistical differences (P ≤ 0.10) between values in that column A combination of xylanase, β-glucanase and a *bacillus* based direct fed microbial improved utilization of dietary energy young broiler compared to either, the control or xylanase alone or a combination of xylanase and β-glucanase (Table 5). This could be linked increased retention of energy yielding nutrients such as fibre, fat and nitrogen (Table 5). The enhanced fat retention due to the three way combinations is noteworthy and could be linked to enhanced digestion and absorption of dietary fat and also production and absorption of short chain fatty acids from fermentation. The observed benefits of the three way combination of xylanase, β-glucanase, *bacillus*/propionic DFM better in energy and nutrients utilization could also be speculatively linked to improved gut health and function through positive microbiota modulation and gut digestive/absorptive function.

III. Lactic Acid Production in the Caecum

Materials and Methods

In Vitro Simulation of Chicken Caecum

A chicken caecum model was developed from an earlier described human colon in vitro system (Mäkivuokko et al. 2006; Nutrition and Cancer 52:94-104, Mäkeläinen et al. 2009; International Dairy Journal 19:675-683). This caecum in vitro model is comprised of four connected vessels inoculated with fresh caecal microbes. A wheat-wheat bran based basal diet was formulated to be balanced for energy and nutrients for young broiler chicks (Table 1, Diet III). No synthetic antimicrobials or anti-coccidial drugs were included in the basal diet. The basal diet was divided into portions and the respective enzymes and DFMs added to constitute experimental diets identified in Table 6. The different feeds underwent a simulated digestion of the upper gastrointestinal tract before they were fed to the in vitro caecum system during a 5-hour simulation. The vessels model the caecum compartments of the chicken, each having the same pH (6.25). Chromatographic analysis of lactic acid from the caecal simulation samples was performed with pivalic acid as internal standard in a similar matter as previously described (Ouwehand et al. 2009; *The British Journal of Nutrition* 101:367-375).

TABLE 6

Identification of treatments

| ID | Description |
|---|---|
| 1 | Xylanase[1] (2500 XU/kg) |
| 2 | Xylanase + FDE mix[2] |
| 3 | Xylanase (2500 XU/kg) + FDE mix[2] + DFM[3] |

[1]Danisco xylanase, Danisco Animal Nutrition
[2]ACCELLERASE ® TRIO ™ enzyme complex contains a potent combination of multiple enzyme activities including β-glucanases (200 CMC U/kg), xylanases (e.g. endoxylanases - endo-1,4-β-D-xylanase (E.C. 3.2.1.8))(>1200 ABX U/kg) and β-glucosidases (>800 pNPG U/kg) supplied by DuPont Industrial Biosciences.
[3]a three-strain *Bacillus* based direct fed microbial selected for their ability to secrete enzymes supplied by Danisco Animal Nutrition as equal proportions of strains AGTP BS918 (NRRL B-50508), AGTP BS3BP5 (NRRL B-50510) and AGTP BS1013 (NRRL B-50509).

Results

TABLE 7

Effects of xylanase, a mixture of fiber degrading enzymes and a direct fed microbial on lactic acid production in a chicken cecum

| Treatment | Lactic acid, μmol/ml |
|---|---|
| 1 | 17.51b |
| 2 | 19.67b |
| 3 | 42.23a |
| SEM | 7.525 |

N.B. Different letters following the values show statistical differences (P ≤ 0.10) between values in that column The combination of xylanase+a mix of other fibre degrading enzymes+*bacillus* based direct fed microbials increased the caecal lactic acid production compared with single, enzyme or enzyme combinations alone. Lactic acid is produced by lactic acid bacteria, in which lactobacilli and streptococci predominate; these bacteria are known to have health-promoting properties in the gut (Walter, 2008; *Applied and Environmental Microbiology* 74: 4985-4996). Lactic acid has antibacterial effects on pathogens such as *E. coli* and *Salmonella* species (Nout et al. 1989; *International Journal of Food Microbiology* 8, 351-361), and lactobacilli can inhibit adhesion of *E. coli* to the intestines (Hillman et al. 1994; *Journal of Applied Microbiology* 76: 294-300.). High concentrations of lactic acid due to a three way combination of xylanase, fibre degrading enzymes and direct fed microbial should therefore reflect an increased population and activity of these gut health related microbes.

IV. Caecal Microbial Population

Materials and Methods

Broiler chickens are assigned to pens based on initial body weight and experimental diets randomly allocated using a recognized experimental design. The birds are allowed free access to experimental diets for a period between day 0 to 21.

Excreta samples are collected daily from day d18 to d20 and stored at −20° C. On d 21, the birds are euthanized by cervical dislocation, and contents of caeca obtained and stored frozen at −20° C. for determination of caecal VFA.

DNA extraction: 0.2 g of caecal digesta suspended in PBS, and then further isolated by a bead beating step and then automatically with MagMax using a commercial kit, MagMAX™ Total Nucleic Acid Isolation Kit (Applied biosystems). The amount of isolated DNA was determined by using a Nanodrop ND-1000 Full-spectrum UV/Vis Spectrophotometer (Wilmington, DE, USA). Flow cytometry utilised as previously described (Apajalahti et al. 2002, Appl Environ Microbiol 68(10): 4986-4995) for enumeration of total or specific bacteria from the samples.

PCR procedures: Isolated DNA is analysed by qPCR (quantitative polymerase chain reaction) using a applied biosystem. Specific primers are used to detect specifically interesting microbial genus as described in 3.

TABLE 8

References where genus specific primers can be found for the quantification by qPCR of digesta microbial population

| Genus of interest | Reference from which specific primers are obtained |
|---|---|
| Enterobacteriaceae | Matsuda et al. (2007), Appl Environ Microbiol 73(1): 32-39 |
| Propionibacterium | Peng et al. 2011 |
| Lactobacillus | Heilig et al (2002) Appl Environ Microbiol 68:114-123, Walter et al (2001) Appl Environ Microbiol 67: 2578-2585 |
| Ruminococcus | Rinttilä et al (2004), J Appl Microbiol 97, 1166-1177, Mosoni et al. J Appl Microbiol, 2007, 103: 2676-85 http://www.ncbi.nlm.nih.gov/pubmed/18045448 |
| Fibrobacter | MvDonald et al. 2008. Environ. Microbiol. 1: 1310-1319 |
| Roseburia | Mäkivuokko et al. 2010. Beneficial Microbes, 1; 131-137 |
| Faecalibacterium | Rinttilä et al. J Appl Microbiol, 2004, 97, 1166-1177 |
| Bacteroides | Mulugeta et al., 2012. J Environ Manage. 2012 Jul. 30; 103: 95-101. |

The combination of xylanase+(mannanase or β-Glucanase)+DFMs induces a shift in caecal microbial population in favour of *Lactobacillus* and/or other specific groups known as fibrolytic bacteria: Ruminococcus, *Bacteroides*, *Roseburia*.

Example 2: Effect of 2 Xylanases and Other Fibre Degrading Enzymes (FDE-Mix) and DFM (*Bacillus* Based Direct Fed Microbial; *Lactobacillus* Based Direct Fed Microbials when Fed Singly or in Combination on Growth Performance and Cecal Volatile Fatty Acids in Young Broiler Chickens Fed Corn-Based Diets Experiment 1
Material and Methods The use of animals and experimental protocol is approved by the institutional Animal Experiment Committee. The basal diet, as fed, is formulated to be balanced for energy and protein, and to match the requirements for growing birds of this age and genotype (Table 9). The cereal component of the diet is corn, and protein component can be soybean meal with or without other protein ingredients such as canola, rape seed meal, etc. Corn co-products such as DDGS or corn gem meal or corn gluten feed can be included either singly or in combination provided that the diet is formulated to meet the nutrient requirements of the birds being fed. No synthetic antimicrobials or anti-coccidial drugs are included, and the diet is supplied as a mash. A common digestibility marker (Titanium dioxide, chromic oxide or celite) is included at 3 g/kg to allow determination of digestibility of dietary components. The basal diet is divided into portions and the respective enzymes and DFMs added to constitute experimental diets identified in Table 10. Each supplement is pre-mixed and the mixer is flushed to prevent cross contamination of treated diets. Samples are collected from each treatment diet from the beginning, middle, and end of each batch and blended together to confirm enzyme activities and DFM presence in feed before commencement of the animal trial. Additional samples from each treatment diet are retained and stored until required at −20° C.±2° C. for analysis.

TABLE 9

Composition of the corn basal diet (%, as fed) for broilers d 0-21

|  | Diet I | Diet II |
|---|---|---|
| Corn | 54.7 | 58.2 |
| Corn DDGS | 11.0 | — |
| Rapeseed meal | — | 16.2 |
| Soybean Meal | 28.9 | 19.4 |
| Fat | 1.00 | — |
| Rapeseed oil | — | 2.11 |
| L-Lysine HCl | 0.43 | 0.50 |
| DL-Methionine | 0.27 | 0.17 |
| L-Threonine | 0.11 | 0.16 |
| Sodium Bicarbonate | 0.20 | — |
| Salt | 0.22 | 0.35 |
| Limestone | 1.53 | 0.70 |
| Monocalcium phosphate | 0.56 | 1.90 |
| Vitamin/mineral premix | 1.00 | 0.40 |
| Calculated provisions |  |  |
| Crude protein, % | 21.1 | 21.1 |
| Metabolizable energy, MJ/kg | 11.5 | 11.6 |
| Calcium | 0.89 | 0.89 |
| Digestible phosphorous, % | 0.28 | 0.28 |
| Digestible Lysine, % | 1.15 | 1.15 |
| Digestible Methionine, % | 0.55 | 0.55 |

TABLE 10

Experimental diets identification

| Treatment | Description |
|---|---|
| 1 | Control, basal (NC) |
| 2 | NC + Xylanase[1] 1 |
| 3 | NC + Xylanase 1 + FDE mix[4] |
| 4 | NC + Xylanase 1 + *Bacillus* DFM[2] |
| 5 | NC + Xylanase 1 + *Lactobacillus* DFM[3] |
| 6 | NC + Xylanase 1 + FDE mix[4] + *Bacillus* DFM[2] |
| 7 | NC + Xylanase 1 + FDE mix[4] + *Lactobacillus* DFM[3] |
| 8 | NC + Xylanase[1] 2 |
| 9 | NC + Xylanase 2 + FDE mix[4] |
| 10 | NC + Xylanase 2 + *Bacillus* DFM[2] |
| 11 | NC + Xylanase 2 + *Lactobacillus* DFM[3] |
| 12 | NC + Xylanase 2 + FDE mix[4] + *Bacillus* DFM[2] |
| 13 | NC + Xylanase 2 + FDE mix[4] + *Lactobacillus* DFM[3] |

[1]Xylanases (e.g. endo-1,4-β-D-xylanase (E.C. 3.2.1.8) from two different origin organisms
[2]*Bacillus* DFM selected as an enzyme producing strain
[3]*Lactobacillus* DFM known to be a C5 sugar-fermenting strain; a short-chain fatty acid-producing strain; a fibrolytic, endogenous microflora-promoting strain; or combinations thereof
[4]FDE mix: Combination of fiber degrading enzyme activities including beta-glucanase, beta-glucosidase, beta-xylosidase and/or alpha-arabinofuranosidase Broiler chickens are assigned to pens based on initial body weight and experimental diets randomly allocated using a recognized experimental design. The birds are allowed free access to experimental diets for a period between day 0 to 21. The body weight (BW), feed intake (FI) and mortalities are recorded to calculate body weight gain (BWG), feed conversion ratio (FCR) and feed conversion efficiency (FCE).

Excreta samples are collected daily from day d18 to d20 and stored at −20° C. for determination of nutrients and fibre retention, and AME and AMEn contents. On d 21, the birds are euthanized by cervical dislocation, and contents of ileum (from Meckel's diverticulum to approximately 1 cm above the ileal-cecal junction) and ceca obtained and stored frozen at −20° C. for determination of ileal digestibility of components and cecal VFA.

Daily excreta samples are pooled for each cage and oven-dried at 60° C., whereas ileal digesta samples were pooled on cage/pen basis and freeze-dried. Samples of the diets, excreta and ileal digesta are finely ground and thoroughly mixed for analysis. All samples are analyzed for dry matter, nitrogen, fat and gross energy according to A.O.A.C. (2005) procedures. Soluble and insoluble non-starch polysaccharides are assayed in diets and excreta according to Englyst et al. (1988) whereas neutral detergent fibre, neutral detergent insoluble nitrogen are assayed according to the methods of Tilley and Terry (1962). Digestibility marker is analyzed according to standard procedure of selected marker.

Chromatographic analysis of volatile fatty acids and lactic acid, e.g. SCFAs, to be performed from simulation samples with pivalic acid as internal standard in a similar matter as previously described (Ouwehand et al., 2009 Feb.; 101(3): 367-75). Concentrations of acetic, propionic, butyric, isobutyric, valeric, isovaleric, 2-methylbutyric acids, and lactic acid are determined.

Coefficient of ileal apparent digestibility and coefficient of apparent retention of components are calculated according to Adeola et al., 2010 (Poult Sci. 2010 Sep.; 89(9):1947-54).

The cage (pen) is the experimental unit. ANOVA is conducted using the General Linear Models of SAS (SAS Inst. Inc., Cary, NC). When F-ratios indicate significance, treatment means are separated.

Results

Treated groups fed the whole combination: xylanase plus a secondary fibre degrading enzyme(s) and a DFM (*Bacillus* or LB), have higher BWG (g/bird/day), and/or a lower FCR (g BW gain/g feed intake) and/or better nutrients, energy and fibre digestibility/retention than either the control, or these additives fed alone or in two-way combination.

The combination of xylanases (xylanase 1 and/or 2)+an FDE mix+DFMs significantly increases the ileal and/or caecal total VFA and the concentration of butyric acid or propionic acid in the ileal and/or caecal digesta of broilers.

II. Growth Performance

Experiment I

Materials and Methods

The use of animals and experimental protocol was approved by the Institutional Animal Experiment Committee. A corn/soy based diet was formulated to be balanced for energy and nutrients for young broiler chicks (0-21 days of life) (Table 9, Diet I). No synthetic antimicrobials or anticoccidial drugs were included, and the diet was supplied as a mash. The basal diet was divided into portions and the respective enzymes and DFMs added to constitute experimental diets identified in Table 11.

TABLE 11

Treatments identification used in experiment I

| ID | Description |
|---|---|
| 1 | Negative Control, no additive (NC) |
| 2 | NC + Xylanase[a] 1 |
| 3 | NC + Xylanase 1 + B-glucanase[a] |
| 4 | NC + Xylanase 1 + *Bacillus* DFM[b] |
| 5 | NC + Xylanase 1 + B-glucanase + *Bacillus* DFM |

TABLE 11-continued

Treatments identification used in experiment I

| ID | Description |
|---|---|
| 6 | NC + Xylanase 2[c] |
| 7 | NC + Xylanase 2 + B-glucanase |
| 8 | NC + Xylanase 2 + *Bacillus* DFM |
| 9 | NC + Xylanase 2 + B-glucanase + *Bacillus* DFM |

[a]The enzymes (xylanase (Danisco Xylanase an endo-1,4-β-D-xylanase (E.C. 3.2.1.8)) and β-glucanase (Axtra ® XB)) are commercial products supplied by Danisco Animal nutrition
[b]Three-strain *Bacillus* based DFM (equal proportions of strains AGTP BS918 (NRRL B-50508), AGTP BS3BP5 (NRRL B-50510) and AGTP BS1013 (NRRL B-50509)), selected for their ability to secrete enzymes
[c]FveXyn4 xylanase (an endo-1,4-β-D-xylanase (E.C. 3.2.1.8)) shown as SEQ ID No. 3 herein (also described in PCT/CN2012/079650 which is incorporated herein by reference), Danisco Animal Nutrition.

All supplements were provided in a premix which was added to the mixer during diet preparation. Diets containing the DFM were mixed first and the mixer was flushed between each diet to prevent cross contamination. Samples were collected from each treatment diet from the beginning, middle, and end of each batch and blended together to confirm enzyme activities and DFM presence in feed before commencement of the animal trial. Additional samples from each treatment diet were retained and stored until required at −20° C.±2° C. for analysis. Male broiler (Hubbard-Cobb) chicks were obtained as day-olds from a commercial hatchery. On day 0 the chicks were individually weighed and allocated to 72 cages (8 chicks per cage) so that the average bird weight per cage was similar. The 9 dietary treatments (Table 11) were then randomly assigned to 8 cages each. The cages were housed in environmentally controlled rooms. The temperature was maintained at 31° C. in the first week and then gradually reduced to 22° C. by the end of third week. The birds received 20 hours fluorescent illumination and, allowed free access to the diets and water for the duration of the study. Body weights and feed intake were recorded the beginning and end of the 21-d experimental period. Mortality was recorded daily. Feed conversion ratios were calculated by dividing total feed intake by weight gain of live plus dead birds. Data was analysed using the General Linear Models of SAS (SAS Inst. Inc., Cary, NC). When F-ratios indicate significance, treatment means are separated.

Results, Experiment I

TABLE 12

Effects of xylanase, β-glucanase and a bacillus based direct fed microbials on growth performance of a young broiler chick.

| | Body Weight Gain (g) | Feed Intake (g) | Feed Conversion (g/g) |
|---|---|---|---|
| 1 | 652.5[d] | 980.8 | 1.498[a] |
| 2 | 670.6[bc] | 982.3 | 1.465[bc] |
| 3 | 673.6[abc] | 978.3 | 1.452[cde] |
| 4 | 681.7[ab] | 982.3 | 1.441[def] |
| 5 | 688.2[a] | 977.2 | 1.420[f] |
| 6 | 665.7[cd] | 985.4 | 1.477[ab] |
| 7 | 671.2[bc] | 982.4 | 1.464[bcd] |
| 8 | 677.0[abc] | 979.0 | 1.446[cde] |
| 9 | 684.5[ab] | 981.5 | 1.430[ef] |
| Std. error | 6.4 | 11.5 | 0.009 |

N.B. Different letters following the values show statistical differences (P ≤ 0.10) between values in that column Treated groups fed the whole combination: xylanase+β-glucanase+*Bacillus* DFM combination had higher BWG (g/bird/day), and lower FCR (g BW gain/g feed intake) than either the control, or these additives fed alone or in two-way combination (Table 12). This was the case when both Xylanase 1 and Xylanase 2 were administered.

Experiment II

Materials and Methods

The use of animals and experimental protocol was approved by the Institutional Animal Experiment Committee. A corn/soy based diet was formulated to be balanced for energy and nutrients for young broiler chicks (0-21 days of life) (Table 9, Diet I). No synthetic antimicrobials or anti-coccidial drugs were included, and the diet was supplied as a mash. The basal diet was divided into portions and the respective enzymes and DFMs added to constitute experimental diets identified in Table 13.

TABLE 13

Treatments identification for Experiment II

| ID | Description |
|---|---|
| 1 | Negative Control, no additive (NC) |
| 2 | NC + Xylanase 1 (2500 XU/kg) |
| 3 | NC + Xylanase 1 (2500 XU/kg) + β-glucanase (200 BGU/kg) |
| 4 | NC + Xylanase 1 (2500 XU/kg) + *Enterococcus* DFM |
| 5 | NC + Xylanase 1 (2500 XU/kg) + β-glucanase (200 BGU/kg) + *Enterococcus* DFM |
| 6 | NC + Xylanase 2 (2500 XU/kg) |
| 7 | NC + Xylanase 2 (2500 XU/kg) + β-glucanase (200 BGU/kg) |
| 8 | NC + Xylanase 2 (2500 XU/kg) + *Enterococcus* DFM |
| 9 | NC + Xylanase 2 (2500 XU/kg) + β-glucanase (200 BGU/kg) + *Enterococcus* DFM |

[a]The enzymes (xylanase (Danisco Xylanase an endo-1,4-β-D-xylanase (E.C. 3.2.1.8)) and β-glucanase (Axtra ® XB)) are commercial products supplied by Danisco Animal nutrition
[b]*Enterococcus* based DFM (*Enterococcus faecium* ID7 (referred to as *Lactococcus lactis* ID7 in granted U.S. Pat. No. 7,384,628 and deposited at the ATCC depository as PTA-6103 and later reclassified as *Enterococcus faecium* ID7)),
[c]FveXyn4 xylanase (an endo-1,4-β-D-xylanase (E.C. 3.2.1.8)) shown as SEQ ID No. 3 herein (also described in PCT/CN2012/079650 which is incorporated herein by reference), Danisco Animal Nutrition All supplements were provided in a premix which was added to the mixer during diet preparation. Diets containing the DFM were mixed first and the mixer was flushed between each diet to prevent cross contamination. Samples were collected from each treatment diet from the beginning, middle, and end of each batch and blended together to confirm enzyme activities and DFM presence in feed before commencement of the animal trial. Additional samples from each treatment diet were retained and stored until required at −20° C.±2° C. for analysis. Male broiler (Hubbard-Cobb) chicks were obtained as day-olds from a commercial hatchery. On day 0 the chicks were individually weighed and allocated to 72 cages (8 chicks per cage) so that the average bird weight per cage was similar. The 9 dietary treatments (Table 13) were then randomly assigned to 8 cages each. The cages were housed in environmentally controlled rooms. The temperature was maintained at 31° C. in the first week and then gradually reduced to 22° C. by the end of third week. The birds received 20 hours fluorescent illumination and, allowed free access to the diets and water for the duration of the study. Body weights were recorded the beginning and end of the 21-d experimental period. Mortality was recorded daily. The data were analyzed using the GLM procedure of SAS.

Results, Experiment II

TABLE 14

Effects of xylanase, β-glucanase and an *Enterococcus* based direct fed microbials on growth performance of a young broiler chick.

| | Body Weight Gain (g) |
|---|---|
| 1 | 652.5$^c$ |
| 2 | 670.6$^{ab}$ |
| 3 | 673.6$^{ab}$ |
| 4 | 677.7$^{ab}$ |
| 5 | 684.4$^a$ |
| 6 | 665.7$^{bc}$ |
| 7 | 671.2$^{ab}$ |
| 8 | 673.7$^{ab}$ |
| 9 | 682.4$^a$ |
| Std. Error | 6.5 |

N.B. Different letters following the values show statistical differences (P ≤ 0.10) between values in that column There was a numerical improvement in broiler body weight gain, when the combination of xylanase+β-glucanase+*Enterococcus* DFM was supplemented on top of xylanase+β-glucanase or xylanase+*Enterococcus* DFM (Table 14).

III. Volatile Fatty Acid Production in the Caecum

Materials and Methods

A corn-soybean meal-rapeseed meal based basal diet was formulated to be balanced for energy and nutrients for young broiler chicks (Table 9, Diet II). No synthetic antimicrobials or anti-coccidial drugs were included in the basal diet. The basal diet was divided into portions and the respective enzymes and DFMs added to constitute experimental diets identified in Table 15. Subsequent procedures were similar to the ones described for Example 1, part III. followed. Chromatographic analysis of volatile fatty acids from simulation samples (see Example 1, part III) was performed with pivalic acid as internal standard in a similar matter as previously described (Ouwehand et al. 2009; *The British Journal of Nutrition* 101: 367-375 the teaching of which is incorporated herein by reference). Concentrations of acetic, propionic, butyric, isobutyric, valeric, isovaleric, and 2-methylbutyric acids were determined.

TABLE 15

Treatments identification

| ID | Description |
|---|---|
| 1 | Control |
| 2 | Xylanase (2500 XU/kg) |
| 3 | Xylanase (2500 XU/kg) + β-glucanase (200 BGU/kg) |
| 4 | Xylanase (2500 XU/kg) + β-glucanase (200 BGU/kg) + DFM)7.5e+04)[1] |

[1]A three-strain *Bacillus* based direct fed microbial (equal proportions of strains AGTP BS918 (NRRL B-50508), AGTP BS3BP5 (NRRL B-50510) and AGTP BS1013 (NRRL B-50509)), selected for their ability to secrete enzymes supplied by Danisco Animal Nutrition.
The enzymes (xylanase (Danisco Xylanase an endo-1,4-β-D-xylanase (E.C. 3.2.1.8)) and β-glucanase (Axtra ® XB)) are commercial products supplied by Danisco Animal nutrition Results

TABLE 16

Effects of xylanase, β-glucanase and a direct fed microbial on acetic and butyric and total volatile fatty acids (VFA) production in chicken cecum

| | Concentration, μmol/ml | | |
|---|---|---|---|
| | Acetic | Butyric | VFA |
| 1 | 61.36b | 6.06c | 68.59b |
| 2 | 112.6ab | 33.0b | 148.3ab |
| 3 | 133.6ab | 43.5ab | 181.3ab |
| 4 | 164.6a | 59.0a | 227.2a |
| Pooled std. error | 27.40 | 5.26 | 35.99 |

N.B. Different letters following the values show statistical differences (P ≤ 0.10) between values in that column The combination of xylanase+β-glucanase+direct fed microbials increased the caecal acetic acid, butyric acid and volatile fatty acid (VFA) production compared with single DFM, enzymes or enzyme combinations alone (Table 16). Volatile fatty acids can provide significant amount of energy to the chicken. Butyric acid is also known to improve gastrointestinal health and reduced incidence of colon cancer in humans (Brons et al., 2002, *Trends Food Science and Technology* 13:251-261 which is incorporated herein by reference).

Example 3: Effect of Xylanase and Other Fibrolytic Enzymes (β-Glucanase or Fibre Degrading Enzyme Mix (FDE-Mix)) and DFM (*Bacillus* Based Direct Fed Microbial) when Fed Singly or in Combination on Growth Performance and Nutrients Digestibility in Pigs (25 to 60 kg) Fed Mixed Grains-Based Diets Material and Methods The use of animals and experimental protocol is approved by the Animal Experiment Committee. The basal diet, as fed, is formulated to be balanced for energy and protein, and to match the requirements for growing pigs of this age and genotype (Table 17). The major ingredients composition (type and inclusion levels) in the basal diet can vary as shown in table 17 provided that the diet is formulated to meet the nutrient requirements of the pigs being fed. A common digestibility marker (Titanium dioxide, chromic oxide or celite) is included at 3 g/kg to allow determination of digestibility of dietary components. No synthetic antimicrobials or anti-coccidial drugs are included, and the diet is supplied as a mash. The basal diet is divided into portions which are then treated with the enzymes and DFMs identified in Table 18. During feed mixing, the mixer is flushed to prevent cross contamination of diet. Samples are collected from each treatment diet from the beginning, middle, and end of each batch and blended together to confirm enzyme activities and DFM presence in feed. Samples from each treatment diet are retained during mixing and stored at −20° C. until required.

TABLE 17

Examples of basal diet composition for pigs 20 to 60 kg body weight (%, as fed)

| | Diet I | Diet II |
|---|---|---|
| Corn | 45.4 | 9.50 |
| Wheat | — | 25.0 |
| Barley | — | 25.0 |

TABLE 17-continued

Examples of basal diet composition for pigs 20 to 60 kg body weight (%, as fed)

| | Diet I | Diet II |
|---|---|---|
| corn DDGS | 25.0 | 10.0 |
| Corn germ meal | 15.0 | — |
| Wheat middlings/rice bran | — | 7.00 |
| Soybean Meal | 10.0 | 10.0 |
| Canola Meal | — | 9.00 |
| Fat | 0.56 | 1.23 |
| Molasses | — | — |
| L-Lysine HCl | 0.59 | 0.47 |
| DL-methionine | 0.02 | 0.02 |
| L-threonine | 0.13 | 0.09 |
| L-tryptophan | — | 0.01 |
| Salt | 0.46 | 0.54 |
| Limestone | 1.16 | 0.63 |
| Dicalcium Phosphate | 0.39 | 1.12 |
| Vitamin and mineral premix | 1.00 | 0.10 |
| Inert marker digestibility marker | 0.30 | 0.30 |
| Crude protein, % | 19.1 | 18.3 |
| Digestible energy, MJ/kg | 13.8 | 13.6 |
| Digestible lysine, % | 1.03 | 0.98 |
| Calcium, % | 0.66 | 0.66 |
| Digestible phosphorous, % | 0.31 | 0.31 |

TABLE 18

Experimental diets identification

| Treatment | Description |
|---|---|
| 1 | Control, basal (NC) |
| 2 | NC + xylanase |
| 3 | NC + xylanase + β-Glucanase |
| 4 | NC + xylanase + FDE mix[1] |
| 5 | NC + xylanase + Bacillus DFM[2] |
| 6 | NC + xylanase + FDE mix + Bacillus DFM[2] |
| 7 | NC + xylanase + β-Glucanase + Bacillus DFM[2] |

[1] FDE mix: Combination of fibre degrading enzyme activities including beta-glucanase, beta-glucosidase, beta-xylosidase and/or alpha-arabinofuranosidase
[2] Bacillus DFM selected as an enzyme producing strain The experiment is planned and conducted to correspond to growing phase (≤25 to ~60 kg body weight). The experimental diets are fed for 42 days of 6 weeks. A group of female and male pigs close to the target initial body are procured from the same herd (genetics). Upon arrival pigs are weighed and allotted to the dietary treatments using a recognised experimental design such that each treatment has a minimum of 8 replicate pens. The body weight and feed intake are monitored weekly for calculation of feed conversion efficiency of gain efficiency corrected for mortalities. Fresh grab fecal samples are collected in week 3 and 6 to allow for calculation of dietary component digestibility.

Growing barrows (initial body weight of 30 kg) are equipped with a T-cannula in the distal ileum for the purpose of the experiment. Pigs are housed in individual pens (1.2×1.5 m) in an environmentally controlled room. Each pen was equipped with a feeder and a nipple drinker and had fully slatted concrete floors. The experiment is designed and conducted to give a minimum of 6 replicates per treatment. All pigs are fed at a level of 3 times their maintenance energy requirement (106 kcal ME per $kg^{0.75}$; NRC, 1998), and provided at two equal portions at 0800 and 1700 h. Animals are allowed free access to water through a bowl-type drinker. Pig weights are recorded at the beginning and at the end of each period and the amount of feed supplied each day are recorded. Experimental period lasts for 15 d. The initial 10 days of each period are considered an adaptation period to the diet. Fresh grab fecal samples are collected on d 11 to 13 and Ileal digesta are collected for 8 hon d 14 and 15 using standard operating procedures. For ileal digesta collection, a plastic bag is attached to the cannula barrel and digesta flowing into the bag collected. Bags are removed whenever they are filled with digesta—or at least once every 30 min and immediately frozen at −20° C.

Fecal and ileal samples are thawed, mixed within animal and diet, and a sub-sample collected for chemical analysis. A sample of basal diet is also collected and analyzed. Digesta samples were lyophilized and finely ground prior to chemical analysis. Fecal samples are dried in an oven and finely ground for analysis. All samples were analyzed for dry matter, digestibility marker, gross energy, crude protein, fat and neutral detergent fibre according to standard procedures (AOAC, 2005).

The values for apparent ileal and total digestibility of energy and nutrients are calculated as described previously (Stein et al., 2007. J. Anim. Sci. 85:172-180). The pen is the experimental unit. Data are subjected the MIXED procedures of SAS.

Results

Treated groups fed the whole combination: xylanase plus a secondary fibre degrading enzyme (β-Glucanase or FDE-mix) and a DFM (Bacillus based direct fed microbial), have higher BWG, and/or a lower FCR (g BW gain/g feed intake) and/or high digestibility of nutrients and/or energy and/or dry matter and/or fibre.

Example 4: Effects of Xylanase, β-Glucanase and a Propionic Acid Producing Strain of Bacteria Based Direct Fed Microbials on Nutrients Retention/Digestibility and Energy Metabolizability in a Young Broiler Chick Composition of the wheat based experimental diets used in Example 4

TABLE 19

Diet composition of broiler wheat-basal diets (% as fed)

| Ingredients | % |
|---|---|
| Wheat | 43.9 |
| Wheat middlings | 2.83 |
| Barley | 10.0 |
| Rye | 5.00 |
| Soybean Meal | 29.3 |
| Fat | 4.25 |
| L-Lysine HCl | 0.32 |
| DL-Methionine | 0.24 |
| L-Threonine | 0.10 |
| Sodium Bicarbonate | 0.20 |
| Salt | 0.23 |
| Limestone | 1.32 |
| Monocalcium Phosphate | 1.00 |
| Trace minerals/vitamins premix | 1.00 |
| Titanium dioxide | 0.30 |
| Calculated Provisions | |
| Crude protein, % | 21.8 |
| Metabolizable energy, MJ/kg | 11.60 |
| Calcium, % | 0.88 |
| Available Phosphorous, % | 0.38 |
| Digestible Lysine, % | 1.15 |
| Digestible Methionine % | 0.51 |

Material and Methods

The use of animals and experimental protocol was approved by the Institutional Animal Experiment Committee. A wheat-barley based diet was formulated to be balanced for energy and nutrients for young broiler chicks (0-21 days of life) (Table 19). Titanium dioxide was included at 0.30% to allow determination of dietary component retention. No synthetic antimicrobials or anti-coccidial drugs were included, and the diet was supplied as a mash. The basal diet was divided into portions and the respective enzymes and DFMs added to constitute experimental diets identified in Table 20. Each supplement was pre-mixed and the mixer was flushed to prevent cross contamination of treated diets. Samples were collected from each treatment diet from the beginning, middle, and end of each batch and blended together to confirm enzyme activities and DFM presence in feed before commencement of the animal trial. Additional samples from each treatment diet are retained and stored until required at −20° C.±2° C. for analysis.

TABLE 20

Identification of treatments

| ID | Description |
|---|---|
| 1 | Control, no additive |
| 2 | NC + Xylanase (2500 XU/kg) |
| 3 | NC + Xylanase (2500 XU/kg) + β-glucanase (200 BGU/kg) |
| 4 | NC + Xylanase (2500 XU/kg) + β-glucanase (200 BGU/kg) + DFM[1] (7.5e+04) |

[1]Propionic acid producing strains based direct fed microbials (*Propionibacterium acidipropionici* P169 PTA-5271, Omni-Bos ® P169). The enzymes (xylanase (Danisco Xylanase an endo-1,4-β-D-xylanase (E.C. 3.2.1.8)) and β-glucanase (Axtra ® XB)) are commercial products supplied by Danisco Animal nutrition.

The study involved a cage trial, which was conducted to obtain excreta samples for energy and nutrients digestibility measurements. Day-old male broiler chicks (Ross 308) were obtained from a commercial hatchery. The chicks were individually weighed upon arrival and stratified by body weight and allocated to 30 cages (five chicks per cage) so that the average bird weight per cage was similar. The four dietary treatments were then randomly assigned to six replicate cages. The trial was conducted from day 0 to 21 during which the birds had free access to their assigned dietary treatments and water. The brooder and room temperatures were set at 32 and 29° C., respectively, during the first week. Thereafter, heat supply in the brooder was switched off and room temperature was maintained at 29° C. throughout the experiment. Light was provided for 24 h throughout the experiment. On days 17, 18, 19 and 20, samples of excreta were collected and stored frozen at −20° C. for the determination of energy and nutrients retention/digestibility. Care was taken during the collection of excreta samples to avoid contamination from feathers and other foreign materials. Excreta samples were pooled within a cage mixed well using a blender and two representative samples per cage were taken. The samples were freeze-dried. Dried samples were ground to pass through a 0.5 mm sieve and stored in airtight plastic containers at −4° C. until chemical analyses. Samples of diets and excreta were analyzed for dry matter, crude protein (as nitrogen), gross energy, fat (as hexane extracts) and neutral detergent fibre according to AOAC official methods of analysis). Titanium (digestibility marker) was analyzed according to the procedures described by Lomer et al. (2000, Analyst 125.2339-2343), which is incorporated herein by reference. Retention/Digestibility was calculated using the standard procedures (Adeola, O. 2001. Digestion and balance techniques in pigs. Pages 903-916 in Swine Nutrition, 2nd ed. A. J. Lewis, and L. L. Southern, ed. CRC Press, Washington, DC which is incorporated herein by reference). Data were analyzed using the General Linear Models procedure of SAS (2004).

Results

TABLE 21

Effects of xylanase, a fibre degrading enzyme and a propionic acid producing strain of bacteria based direct fed microbials on nutrients retention/digestibility and energy metabolizability in a young broiler chick.

| | Apparent retention/digestibility, % | | ME, |
|---|---|---|---|
| Treatment | Dry matter | Fat | kcal/kg |
| 1 | 67.4d | 78.3c | 2875c |
| 2 | 71.2b | 81.5b | 3033b |
| 3 | 70.9c | 82.9b | 3040b |
| 4 | 72.7a | 86.1a | 3160a |
| Std. error | 0.06 | 0.89 | 15.1 |

N.B. Different letters following the values show statistical differences (P ≤ 0.10) between values in that column A combination of xylanase, β-glucanase and a *bacillus* based direct fed microbial improved utilization of dietary energy compared to either, the control or xylanase alone or a combination of xylanase and β-glucanase (Table 20). This could be linked increased retention of energy yielding nutrients in the dry matter such as fat (Table 20). The enhanced fat retention due to the three way combinations is noteworthy and could be linked to enhanced digestion and absorption of dietary fat and also production and absorption of short chain fatty acids from fermentation. The observed benefits of the three way combination of xylanase, β-glucanase, *bacillus*/propionic DFM better in energy and nutrients utilization could also be speculatively linked to improved gut health and function through positive microbiota modulation and gut digestive/absorptive function.

Example 5: Responses of Broiler Chicken when Fed Corn-Based Diets Containing Xylanase, Other Fibre Degrading Enzymes and Propionic Acid Producing Direct Fed Microbials Composition of the experimental diets used in Example 5

TABLE 22

Diet composition of broiler corn-basal diets (% as fed)

| | Composition (%) |
|---|---|
| Corn | 54.7 |
| Corn DDGS | 11.0 |
| Soybean Meal | 28.9 |
| Fat | 1.00 |
| L-Lysine HCl | 0.43 |
| DL-Methionine | 0.27 |
| L-Threonine | 0.11 |
| Sodium Bicarbonate | 0.20 |
| Salt | 0.22 |
| Limestone | 1.53 |
| Monocalcium phosphate | 0.56 |
| Vitamin/mineral premix | 1.00 |
| Calculated provisions | |
| Crude protein, % | 21.1 |
| Metabolizable energy, MJ/kg | 11.5 |
| Calcium | 0.89 |
| Digestible phosphorous, % | 0.28 |
| Digestible Lysine, % | 1.15 |
| Digestible Methionine, % | 0.55 |

Materials and Methods

The use of animals and experimental protocol was approved by the Institutional Animal Experiment Committee. A corn based diet was formulated to be balanced for energy and nutrients for young broiler chicks (0-21 days of life) (Table 22). No synthetic antimicrobials or anti-coccidial drugs were included, and the diet was supplied as a mash. The basal diet was divided into portions and the respective enzymes and DFMs added to constitute experimental diets identified in Table 23. Each supplement was pre-mixed and the mixer was flushed to prevent cross contamination of treated diets. Samples were collected from each treatment diet from the beginning, middle, and end of each batch and blended together to confirm enzyme activities and DFM presence in feed before commencement of the animal trial. Additional samples from each treatment diet are retained and stored until required at −20° C.±2° C. for analysis.

TABLE 23

Treatments identification

| ID | Description |
|---|---|
| 1 | Control |
| 2 | Xylanase (2500 XU/kg)[1] |
| 3 | Xylanase + FDE mix[2] |
| 4 | Xylanase (2500 XU/kg) + FDE mix + DFM[3] (7.5e+04) |

[1]Danisco xylanase, Danisco Animal nutrition
[2]ACCELLERASE ® TRIO ™ enzyme complex contains a potent combination of multiple enzyme activities including β-glucanases (200 CMC U/kg), xylanases (e.g. endoxylanases, endo-1,4-β-xylanase (E.C. 3.2.1.8)) (>1200 ABX U/kg),and β-glucosidases (>800 pNPG U/kg) (DuPont Industrial Biosciences).
[3]Propionic acid producing strains based direct fed microbials (*Propionibacterium acidipropionici* P169 PTA-5271, Omni-Bos ® P169)

Day old chicks were procured from a commercial hatchery and upon arrival the birds were weighed and tagged for identification and allocated into six blocks by body weight, and randomly allotted to 4 treatments (Table 23) within a block with ten birds per pen in a randomized completed block design. From d 1 and were also allowed ad libitum access to clean drinking water. The chicks were weighed on days 0 and 21 and their weights were recorded, feed consumption was also monitored and documented on chick weigh days. The chicks were monitored daily and variations in their appearance or behaviour were recorded. At the end of each feeding period, parameters such as weight gain, feed intake, feed conversion ratio, feed efficiency, and mortality were determined. Data were analyzed as a randomized complete block design using the GLM procedure of SAS software (SAS Institute, Inc. 2006).

Results

TABLE 24

Effects of xylanase, a mixture of other fibre degrading enzymes and a propionic based direct fed microbials on growth performance of a young broiler chick.

| | Body weight at 21 days, g | Body weight gain, g | Feed intake, g | Feed conversion efficiency, g/g |
|---|---|---|---|---|
| 1 | 830.4 | 783.5 | 1006.6 | 1.284a |
| 2 | 804.2 | 757.3 | 964.0 | 1.273ab |
| 3 | 817.6 | 770.7 | 983.3 | 1.275ab |
| 4 | 813.2 | 766.4 | 953.9 | 1.245b |
| Std. error | 12.96 | 11.82 | 23.37 | 0.017 |

N.B. Different letters following the values show statistical differences (P ≤ 0.10) between values in that column Chicks fed combination of xylanase, a mixture of other fibre degrading enzymes and a propionic based DFM had better FCR than control and numerically better than chicks fed enzymes only diets (Table 24).

Example 6: Effects of Xylanase and β-Glucanase without or with *Bacillus* Strains Based Direct Fed Microbial on Growth Performance, Microbial Counts and Nutrients Digestibility in Growing Finishing Pigs Composition of the experimental diets used in Example 6

TABLE 25

Diet composition of growing pig feed (20-60 kg body weight) (% as fed)

| | Diet I | Diet II |
|---|---|---|
| Corn | 45.4 | 42.3 |
| Wheat | — | 5.00 |
| corn DDGS | 25.0 | 20 |
| Corn germ meal | 15.0 | — |
| Wheat middlings/rice bran | — | 3.00 |
| Soybean Meal | 10.0 | 19.8 |
| Canola Meal | — | 2.00 |
| Fat | 0.56 | 2.00 |
| Molasses | — | 3.00 |
| L-Lysine HCl | 0.59 | 0.24 |
| DL-methionine | 0.02 | 0.02 |
| L-threonine | 0.13 | — |
| Salt | 0.46 | 0.30 |
| Limestone | 1.16 | 1.18 |
| Dicalcium Phosphate | 0.39 | 0.45 |
| Vitamin and mineral premix | 1.00 | 0.30 |
| Inert marker digestibility marker | 0.30 | 0.30 |
| Calculated provisions | | |
| Crude protein, % | 19.1 | 19.2 |
| Digestible energy, MJ/kg | 13.8 | 14.6 |
| Digestible lysine, % | 1.03 | 0.91 |
| Calcium, % | 0.66 | 0.72 |
| Digestible phosphorous, % | 0.31 | 0.33 |

Materials and Methods

Two experiments were conducted to evaluate growth performance, fecal microbial counts and digestibility effects of a xylanase and β-glucanase enzyme blend fed without or with *bacillus* strains based direct fed microbial in growing finishing pigs. The Institutional Animal Care and Use Committee approved the use of the pigs and relevant welfare guidelines for the Country were used. A total of 42 pigs ([♀ Yorkshire×Landrace]×♂ Duroc) housed in groups of two were used in experiment 1 and 72 pigs of the same breed housed in groups of three were used in experiment 2. Each pen had smooth transparent plastic sides and plastic-covered expanded metal sheet flooring in a temperature-controlled room (22±2° C.).

Respective basal diets were formulated to meet the NRC nutrient recommendations for swine (NRC, 1998 Table 25 diet I for experiment 1 and diet II for experiment 2). In each experiment, one batch of the basal diet is manufactured and split into two portions and each portion subsequently mixed with additives identified in Table 26.

TABLE 26

Identification of Treatments

| ID | Description |
|----|-------------|
| 1 | Control |
| 2 | Xylanase (4000 XU/kg) + β-glucanase (360 BGU/kg) |
| 3 | Xylanase (4000U/kg) + β-glucanase (360 U/kg) + DFM[1] (3.0e+08) |

[1] a three-strain *Bacillus* based direct fed microbial (equal proportions of strains AGTP BS918 (NRRL B-50508), AGTP BS3BP5 (NRRL B-50510) and AGTP BS1013 (NRRL B-50509)), selected for their ability to secrete enzymes supplied by Danisco Animal Nutrition. The enzymes (xylanase (Danisco Xylanase an endo-1,4-β-D-xylanase (E.C. 3.2.1.8)) and β-glucanase (Axtra ® XB)) are commercial products supplied by Danisco Animal nutrition The treatments identified in table 26, were allocated to 7 and 8 replicate pens in experiment 1 and 2, respectively. Pen allocation to the treatments was randomized based on pig body weight at the start of the experiment. Body weight and Feed intake were recorded on a weekly basis and used to calculate feed conversion ratio. Pigs were offered the experimental diets for 42 days in both experiments. Feed and water were freely available at all times during experimentation. In experiment 2, fresh fecal samples were collected on days, 38,39 and 40 for determination of nutrients, energy and fibre digestibility as well as fecal microbial counts. One gram of the composite fecal sample from each pen was diluted with 9 mL of 1% peptone broth (Becton, Dickinson and Co., Franklin Lakes, NJ) and then homogenized. Viable counts of bacteria in the fecal samples were then conducted by plating serial 10-fold dilutions (in 1% peptone solution) onto Mac-Conkey agar plates (Difco Laboratories, Detroit, MI) and lactobacilli medium III agar plates (Medium 638, DSMZ, Braunschweig, Germany) to isolate the *E. coli* and *Lactobacillus*, respectively. The lactobacilli medium III agar plates were then incubated for 48 h at 39° C. under anaerobic conditions. The MacConkey agar plates were incubated for 24 h at 37° C. The *E. coli* and *Lactobacillus* colonies were counted immediately after removal from the incubator. Before chemical analysis, the fecal samples were thawed and dried at 60° C. for 72 h, after which they were finely ground to a size that could pass through a 1-mm screen. All feed and fecal samples were, then, analyzed for dry matter, gross energy and acid detergent fibre following the procedures outlined by the AOAC (Official Methods of Analysis). Chromium (digestibility marker) was analyzed following the method described by Williams et al. 1962, J. Anim. Sci. 59:381-389, which is incoporporated herein by reference. Digestibility was calculated using standard procedures (Adeola, O. 2001. Digestion and balance techniques in pigs. Pages 903-916 in Swine Nutrition, 2nd ed. A. J. Lewis, and L. L. Southern, ed. CRC Press, Washington, DC—the teaching of which is incorporated herein by reference). The growth performance data (BW, ADFI, ADG and FCR) were subjected to the GLM procedures of SAS with treatments, experiment and interactions as effects in the model. Initial analysis revealed interactions were not significant and as such dropped in further analysis, subsequently treatments main effects are presented. The microbial count data were log transformed and along with digestibility subjected to one-way anova using the GLM procedures of SAS.

Results

TABLE 27

Effects of xylanase and β-glucanase without or with bacillus strains based direct fed microbial on growth performance in growing finishing pigs

| Treatments | Initial body weight, kg | Final body weight, kg | Daily gain, grams/day | Feed intake, grams/day | Feed conversion efficiency, g/g |
|---|---|---|---|---|---|
| 1 | 17.4 | 50.6b | 719.4b | 1411.1a | 1.967 |
| 2 | 17.5 | 51.7ab | 743.9ab | 1431.3ab | 1.942 |
| 3 | 17.4 | 52.6a | 764.1a | 1471.5a | 1.922 |
| Std. err. | 0.35 | 0.81 | 14.00 | 19.20 | 0.041 |

N.B. Different letters following the values show statistical differences ($P \leq 0.10$) between values in that column

TABLE 28

Effects of xylanase and β-glucanase without or with bacillus strains based direct fed microbial on dry matter, nitrogen, fibre and energy digestibility (%) in growing finishing pigs

| Treatments | Dry matter | Nitrogen | Acid detergent fibre | Energy |
|---|---|---|---|---|
| 1 | 80.4b | 77.4b | 44.2b | 79.3b |
| 2 | 80.8b | 77.8b | 44.6b | 78.6b |
| 3 | 82.0a | 79.4a | 56.1a | 80.5a |
| Std. err. | 0.41 | 0.51 | 1.65 | 0.47 |

Figure 1B:
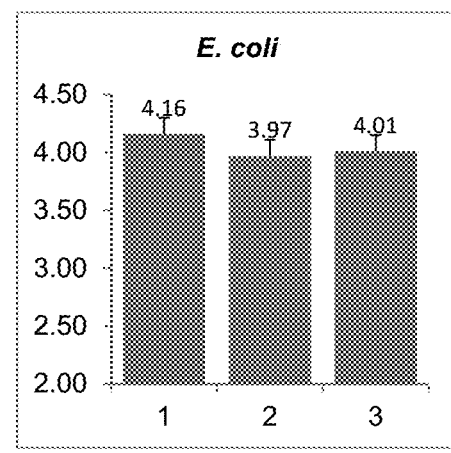

N.B. Different letters following the values show statistical differences ($P \leq 0.10$) between values in that column A combination of xylanase, β-glucanase and a direct fed microbial containing either *bacillus* improved growing pig growth performance and utilization of dietary nutrients and energy compared to either, the control or enzyme only (Tables 27 & 28). Three way combinations were also seen to result in more fibre degradation and promoted proliferation of *lactobacillus* bacteria in the gut (FIG. 1A and FIG. 1B).

Example 7: Effects of Xylanase, Other Fibre Degrading Enzymes and Direct Fed Microbials on Short Chain Fatty Acids Production in Swine Hind Gut Composition of the experimental diets used in Example 7

TABLE 29

Diet composition of growing pig feed (20-60 kg body weight) (% as fed)

| | Diet I | Diet II |
|---|---|---|
| Corn | 45.7 | 9.50 |
| Wheat | — | 25.3 |
| Barley | — | 25.00 |
| corn DDGS | 25.0 | 10.0 |
| Corn germ meal | 15.0 | — |
| Wheat middlings/rice bran | — | 7.00 |
| Soybean Meal | 10.0 | 10.0 |
| Canola Meal | — | 9.00 |
| Fat | 0.56 | 1.23 |
| Molasses | — | — |
| L-Lysine HCl | 0.59 | 0.47 |
| DL-methionine | 0.02 | 0.02 |
| L-threonine | 0.13 | 0.09 |
| L-tryptophan | — | 0.01 |
| Salt | 0.46 | 0.54 |
| Limestone | 1.16 | 0.63 |

TABLE 29-continued

Diet composition of growing pig feed
(20-60 kg body weight) (% as fed)

| | Diet I | Diet II |
|---|---|---|
| Dicalcium Phosphate | 0.39 | 1.12 |
| Vitamin and mineral premix | 1.00 | 0.10 |
| Calculated chemical concentration | | |
| Crude protein, % | 19.1 | 18.3 |
| Digestible energy, MJ/kg | 13.8 | 13.6 |
| Digestible lysine, % | 1.03 | 0.98 |
| Calcium, % | 0.66 | 0.66 |
| Digestible phosphorous, % | 0.31 | 0.31 |
| Neutral detergent fibre, % | 23.8 | 21.8 |
| Dry matter, % | 89.7 | 90.8 |

Materials and Methods

In order to establish a swine hindgut model, a method was adapted from (Boisen and Fernandez 1997, *Animal Feed Science and Technology* 68: 277-286 the teaching of which is incorporated herein by reference) to generate swine ileal effluent in vitro. In brief, 1.35 kg of complete mash feed (corn and wheat based, details see table 29) was combined with 3.00 L of phosphate buffer (0.1 M, pH 6) and 1.20 L of 0.2 M HCl in a 3 gallon bucket with a re-sealable lid. The pH was adjusted to 2 using 10 M HCl or NaOH. Then 120 mL of a pre-prepared Pepsin solution (250 mg of Pepsin (Sigma-Aldrich, Inc., St. Louis, MO) per mL of water) was added. The bucket was sealed and incubated at 39° C. for 2 hours with shaking in order to simulate stomach digestion. For small intestine digestion simulation, 1.20 L phosphate buffer (0.2 M, pH 6.8) and 600 mL of 0.6 M NaOH were added to the solution and the pH adjusted to 6.8 using 10 M NaOH or HCl as before. After neutralization, 120 mL of pre-prepared pancreatin solution (1000 mg Pancreatin (Sigma-Aldrich) per mL of water) were added, the bucket sealed and incubated at 39° C. for 4 hours with shaking. Following the incubation, the liquid was filtered off using a double layered and twice folded in half brew bag (Jumbo Nylon Coarse, LD Carlson Company, Kent, OH). The remaining slurry was homogenized and divided into portions of 128 g, each weighed into separate 250 mL Pyrex bottles. The bottles were subsequently stored at −20° C. As inoculant for large bowl microbiota, cecal content was collected from 12 grower pigs. Contents were homogenized, mixed with 10% glycerol and 14 g aliquots weighed into 15 mL conicals. Conicals were then sealed and stored at −80° C.

Swine hindgut simulation experiments were performed in duplicate runs, each with 1 control and 3 treatments (Table 30). Each treatment was tested in triplicate. For each in vitro swine hindgut fermentation trial, a total of 24 Pyrex bottles with simulated ileal effluent and one 15 mL conical with cecal content were used. Bottles were thawed overnight and 240 mL sterile 0.1 M phosphate buffer solution (pH 6) with 4 g/L mucin (Sigma-Aldrich) added to each bottle, similar to methods described in (Christensen et al. 1999, *Journal of the Science of Food and Agriculture* 79, 755-762) and Aristoteli and Willcox, 2003, *Infection and immunity* 71: 5565-5575) the teaching of these documents being incorporated herein by reference. The inoculant was thawed for 30 minutes at room temperature while Pyrex bottles were pre-warmed at 39° C. for 30 minutes in a shaking water bath, then treatments in 1 mL 1% peptone solution and 450 μL 0.1 M phosphate buffer (see table 30) were added.

TABLE 30

Treatments tested for swine in vitro hindgut fermentation[*]

| Experiment | Control Basal diet only[#] | Treatment 1 Control with Xylanase enzyme [†] | Treatment 2 Treatment 1 with fibre degrading enzyme [‡] | Treatment 3 Treatment 2 + direct-fed microbial (DFM) [+] |
|---|---|---|---|---|
| 1 | CC | NGX | Accel. | P169 |
| 2 | CC | NGX | Accel. | *Bacillus* |
| 3 | CW | Y5 | Accel. | P169 |
| 4 | CW | Y5 | Axtra ® XB | *Bacillus* |
| 5 | CW | Y5 | Accel. | *Bacillus* |

[*]enzyme and direct-fed microbial products were included at a rate similar to 500 g per metric ton in feed inclusion, each experiment was performed in duplicate runs, treatments were measured in triplicate in each run;
[#]Basal diet is either corn control diet (CC) or wheat control diet (CW), as described in table 29;
[†]Xylanase is either Y5 (Danisco Xylanase an endo-1,4-β-D-xylanase (E.C. 3.2.1.8)) or NGX (FveXyn4 (an endo-1,4-β-D-xylanase (E.C. 3.2.1.8)) shown as SEQ ID No. 3 herein (also described in PCT/CN2012/079650 which is incorporated herein by reference), Danisco Animal Nutrition) with a guaranteed activity of 4000 XU/kg of feed;
[‡]Fibre degrading enzyme is either Accel. (Accelerase Trio, ACCELLERASE ® TRIO ™ enzyme complex contains a combination of multiple enzyme activities including β-glucanases (200 CMC U/kg), xylanases (e.g. endoxylanases, endo-1,4-β-D-xylanase (E.C. 3.2.1.8)) (>1200 ABX U/kg) and β-glucosidases (>800 pNPG U/kg)) (DuPont Industrial Biosciences) enzyme mix or Axtra ® XB β-glucanase with a guaranteed activity of 360 BGU of β-glucanase/kg of feed.
[+] Direct-fed microbial is either *Bacillus* based (equal proportions of strains AGTP BS918 NRRLB-50508, AGTP BS1013 NRRL B-50509 and AGTP BS3BP5 NRRL B-50510) with a guaranteed activity of $3.0 \times 10^8$ cfu per gram of product, or *Propionibacterium acidipropionici* P169 PTA-5271 Omni-Bos ® P169 with a guaranteed activity of $2.1 \times 10^9$ cfu per gram of product.

Bottles were flushed with $CO_2$ gas for 30 seconds while 250 μL of cecal inoculant were added (based on Coles et al. 2005, *Animal Feed Science and Technology* 123: 421-444 the teaching of which is incorporated herein by reference) and a 10 mL baseline sample was collected, baseline pH determined and sample stored at −20° C. Bottles were capped, gently mixed and placed into a shaking water bath at 39° C. and 160 rpm. After 12 h, another 10 mL sample was collected, pH determined and sample stored at −20° C. For volatile fatty acid (VFA) quantification by high-performance liquid chromatography (HPLC) samples were thawed and centrifuged at 16.1 rad for 20 minutes, and the supernatant filtered through a 0.22 μm mixed cellulose ester membrane (Milex-GS, EMD Millipore Corp., Billerica, MA). Of the filtrate, 20 μL was injected into a Waters Alliance 2695 Separations Module (Waters Corp., Milford, MA) equipped with a Shodex SH-G guard column (Waters) and 300×7.8 mm Aminex HPX-87H column (Biorad Laboratories, Inc., Hercules, CA). An isocratic method was applied with a mobile phase consisting of 16.8 mM phosphoric acid in water/acetonitrile (98:2, v/v) at 0.525 mL/min flow rate and 35° C. column temperature. Volatile fatty acids were detected using a Waters 2996 photo diode array (PDA) detector (Waters) at 211 nm absorption. Instrument control, data acquisition, and data processing were achieved with Waters Empower 3 software (Waters). Volatile fatty acids were quantified using standard curves generated from high grade (≥99.9%) reagents (Sigma Aldrich, St. Louis, MO). Linear dilutions of standards in 16.8 mM phosphoric acid in water/acetonitrile (98:2, v/v) were prepared at 6 concentrations ranging from 0.05% to 2.0%. Concentration of acetic acid, propionic acid, butyric acid, iso-butyric acid, valeric acid, iso-valeric acid (the sum of which is presented as total VFA) and lactic acid were determined. Statistical analysis for each experiment was performed as one-way ANOVA blocked by run using GLM procedure of SPSS (version 17, SPSS Inc., Chicago, IL). Significance was declared for P≥0.10, treatment means were separated using Duncan's multiple range test.

Results

In wheat based diets, a significant increase in total VFA and lactic acid production after 12 h of swine hindgut simulation was observed when NGX xylanase, Accelerase Trio fibre degrading enzyme mix and a DFM were added and compared to control without supplementation (Table 31, experiment 1 and 2). Usage of *Propionibacterium acidipropionici* P169 based DFM further significantly increased propionate levels and had a greater acidification of simulated colonic content in the combination treatment compared to the control (Table 31, experiment 1). In corn based diets, the combination treatment of Y5 xylanase, Accelerase Trio fibre degrading enzyme and DFM significantly increased butyrate levels compared to control after 12 h simulated swine hindgut fermentation, with an additional increase of total VFA when *Propionibacterium acidipropionici* P169 based DFM was used (Table 31, experiment 3 and 5). Replacement of Accelerase Trio enzyme mix with Axtra® XB β-glucanase and usage of *Bacillus* based DFM in corn diet with Y5 resulted in significant increase of total VFA and lactate compared to control treatment (Table 31, experiment 4).

Example 8 Effects of Xylanase, Other Fibrolytic Enzymes and Direct Fed Microbials on Swine Hindgut Fibre Degradation Composition of the experimental diet used in Example 8

TABLE 32

| Diet composition of growing pig feed (20-60 kg body weight) (% as fed) | |
|---|---|
| | Diet |
| Corn | 9.50 |
| Wheat | 25.0 |
| Barley | 25.0 |
| corn DDGS | 10.0 |
| Corn germ meal | — |
| Wheat middlings | 7.00 |
| Soybean Meal | 10.0 |
| Canola Meal | 9.00 |
| Fat | 1.23 |
| L-Lysine HCl | 0.47 |

TABLE 31

Mean abundance of Propionate, Butyrate, total volatile fatty acids (VFA) and lactate (% as is), as well as pH differences comparing to baseline samples after 12 h of swine hindgut fermentation in vitro.

| Trt # | Treatment | Propionate | Butyrate | Total VFA | Lactate | Δ pH |
|---|---|---|---|---|---|---|
| | | | Experiment 1 | | | |
| 1 | Corn control (CC) | $0.010^b$ | | $0.457^b$ | $1.193^b$ | $2.452^c$ |
| 2 | CC + NGX | $0.010^b$ | | $0.501^b$ | $1.254^{ab}$ | $2.462^{bc}$ |
| 3 | CC + NGX + Accel. | $0.022^{ab}$ | NS | $0.624^{ab}$ | $1.360^{ab}$ | $2.472^{ab}$ |
| 4 | CC + NGX + Accel. + P169 | $0.056^a$ | | $0.865^a$ | $1.595^a$ | $2.485^a$ |
| | SEM | 0.008 | | 0.073 | 0.086 | 0.005 |
| | | | Experiment 2 | | | |
| 1 | Corn control (CC) | | | $0.531^b$ | $1.341^b$ | |
| 2 | CC + NGX | | | $0.605^{ab}$ | $1.433^b$ | |
| 3 | CC + NGX + Accel. | NS | NS | $0.607^{ab}$ | $1.406^b$ | NS |
| 4 | CC + NGX + Accel. + *Bacillus* | | | $0.773^a$ | $1.681^a$ | |
| | SEM | | | 0.049 | 0.087 | |
| | | | Experiment 3 | | | |
| 1 | Wheat control (CW) | | $0.145^b$ | $0.685^b$ | | |
| 2 | CW + Y5 | | $0.154^{ab}$ | $0.706^{ab}$ | | |
| 3 | CW + Y5 + Accel. | NS | $0.155^{ab}$ | $0.713^{ab}$ | NS | NS |
| 4 | CW + Y5 + Accel. + P169 | | $0.163^a$ | $0.731^a$ | | |
| | SEM | | 0.006 | 0.011 | | |
| | | | Experiment 4 | | | |
| 1 | Wheat control (CW) | | | $0.7720^b$ | $1.970^b$ | |
| 2 | CW + Y5 | | | $0.8258^{ab}$ | $1.993^{ab}$ | |
| 3 | CW + Y5 + Axtra® XB | NS | NS | $0.7885^{ab}$ | $2.014^{ab}$ | NS |
| 4 | CW + Y5 + Axtra® XB + *Bacillus* | | | $0.8600^a$ | $2.027^a$ | |
| | SEM | | | 0.031 | 0.021 | |
| | | | Experiment 5 | | | |
| 1 | Wheat control (CW) | | $0.0627^b$ | | | |
| 2 | CW + Y5 | | $0.0930^{ab}$ | | | |
| 3 | CW + Y5 + Accel. | NS | $0.1242^{ab}$ | NS | NS | NS |
| 4 | CW + Y5 + Accel. + *Bacillus* | | $0.1728^a$ | | | |
| | SEM | | 0.031 | | | |

$^{a,b}$values with differing superscripts within a column are significantly different at P ≤ 0.10;
NS, not significant; SEM, standard error of the mean; treatment details see Table 26

TABLE 32-continued

Diet composition of growing pig feed
(20-60 kg body weight) (% as fed)

|  | Diet |
| --- | --- |
| DL-methionine | 0.02 |
| L-threonine | 0.09 |
| L-tryptophan | 0.01 |
| Salt | 0.54 |
| Limestone | 0.63 |
| Dicalcium Phosphate | 1.12 |
| Vitamin and mineral premix | 0.10 |
| Inert marker digestibility marker | 0.30 |
| Calculated chemical concentration | |
| Crude protein, % | 18.3 |
| Digestible energy, MJ/kg | 13.6 |
| Digestible lysine, % | 0.98 |
| Calcium, % | 0.66 |
| Digestible phosphorous, % | 0.31 |
| Neutral detergent fibre, % | 21.8 |
| Dry matter, % | 90.8 |

To demonstrate disappearance of dry matter (DM) and degradation of fibre, ileal effluents were generated and hindgut fermentation set up as described in example 7. In brief, the wheat based diet (CW, see Table 32) was used as control without any treatment, as well as CW in addition with Y5 xylanase (Treatment 1), CW with Y5 and Accelerase Trio fibre degrading enzyme mix (Treatment 2), CW with Y5, Accelerase in combination with a three strain Bacillus direct-fed microbial (Treatment 3), details to enzyme and DFM treatments see Table 33.

TABLE 33

Identification of Treatments*

| Control Basal diet only # | Treatment 1 Control with Xylanase enzyme † | Treatment 2 Treatment 1 with fibre degrading enzyme ‡ | Treatment 3 Treatment 2 + direct-fed microbial (DFM) + |
| --- | --- | --- | --- |
| CW | Y5 | Accel. | Bacillus |

*enzyme and direct-fed microbial products were included at a rate similar to 500 g per metric ton in feed inclusion, each experiment was performed in duplicate runs, treatments were measured in triplicate in each run;
Basal diet is a wheat control diet (CW), as described in table 32;
† Xylanase is Y5 (Danisco Xylanase an endo-1,4-β-D-xylanase (E.C. 3.2.1.8)) with a guaranteed activity of 4000 XU/kg of feed;
‡ Fibre degrading enzyme is either Accel. (Accelerase Trio, ACCELLERASE ® TRIO ™ enzyme complex contains a potent combination of multiple enzyme activities including β-glucanases (200 CMC U/kg), xylanases (e.g. endoxylanases, endo-1,4-β-D-xylanase (E.C. 3.2.1.8)) (>1200 ABX U/kg) and β-glucosidases (>800 pNPG U/kg) (DuPont Industrial Biosciences) the enzyme mix was dosed to ensure a guaranteed activity of 360 BGU of β-glucanase/kg of feed.
+ Direct-fed microbial is either Bacillus based (equal proportions of strains AGTP BS918 NRRL B-50508, AGTP BS1013 NRRL B-50509 and AGTP BS3BP5 NRRL B-50510) with a guaranteed activity of $3.0 \times 10^8$ cfu per gram of product, or Propionibacterium acidipropionici P169 PTA-5271 Omni-Bos ® P169 with a guaranteed activity of $2.1 \times 10^9$ cfu per gram of product.

Treatment effects on DM and fibre disappearance. At 0 and 48 hours of the experiment, liquid was filtered off and remaining solids were collected and send for approximate nutrient analysis of dry matter (DM), acid and neutral detergent fibre (ADF and NDF, respectively), the latter were generated on DM basis according to methods described in (Association of Analytical Chemists (AOAC) 2007, $18^{th}$ edition. AOAC, Washington, D. C). Data was calculated as percent disappearance, statistical analysis was performed as one-way ANOVA blocked by run using GLM procedure of SPSS (version 17, SPSS Inc., Chicago, IL). Significance was declared for P≤0.10, treatment means were separated using Duncan's multiple range test.

Results

In the tested wheat based diet, the combination treatment with Y5 Xylanase, Accelerase Trio fibre degrading enzyme mix and three Bacillus based DFM had the greatest disappearance of DM, ADF and NDF compared to CW without any enzyme and DFM supplementation (Table 34).

TABLE 34

Percent disappearance of dry matter, acid and neutral detergent fibre during 48 h swine hindgut fermentation in vitro

| Trt # | Treatment | Δ DM (%) | Δ ADF (%) | Δ NDF (%) |
| --- | --- | --- | --- | --- |
| 1 | Wheat control (CW) | 3.95 $^b$ | 2.31 $^b$ | 4.27 $^b$ |
| 2 | CW + Y5 | 3.97 $^b$ | 3.26 $^{ab}$ | 5.87 $^{ab}$ |
| 3 | CW + Y5 + Accel. | 4.19 $^{ab}$ | 3.46 $^{ab}$ | 5.77 $^{ab}$ |
| 4 | CW + Y5 + Accel. + Bacillus | 4.57 $^a$ | 3.66 $^a$ | 7.37 $^a$ |
|  | SEM | 0.17 | 0.31 | 0.88 |

$^{a,b}$ values with differing superscripts within a column are significantly different at P ≤ 0.10;
SEM, standard error of the mean;
treatment details see Table 7.2.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. A method for improving the performance of a subject or for improving digestibility of a raw material in a feed, or for improving nitrogen retention, or for improving feed conversion ratio (FCR), or for improving weight gain in a subject, or for improving feed efficiency in a subject, or for shifting the fermentation process in the subject's gastrointestinal tract towards the production of butyric acid and/or volatile fatty acids (VFA), the method comprising
administering a direct fed microbial (DFM) comprising Bacillus strains AGTP BS3BP5 (NRRL B—50510), AGTP BS918 (NRRL B—50508), and AGTP BS1013 (NRRL B—50509), to the subject, in combination with a xylanase and a β-glucanase.

2. The method of claim 1, wherein the DFM comprises viable bacteria.

3. The method of claim 1, wherein the DFM comprises endospores.

4. The method of claim 1, wherein the xylanase is an endo-1,4-β-d-xylanase.

5. The method of claim 1, further comprising administration of a further fiber-degrading enzyme.

6. The method of claim 5, wherein the further fiber-degrading enzyme is selected from the group consisting of a cellobiohydrolase (E.C. 3.2.1.176 and E.C. 3.2.1.91), a β-glucosidase (E.C. 3.2.1.21), a β-xylosidase (E.C. 3.2.1.37), a feruloyl esterase (E.C. 3.1.1.73), an α-arabinofuranosidase (E.C. 3.2.1.55), a pectinase (E.C. 3.2.1.15), an exopolygalacturonase (E.C. 3.2.1.67), a pectate lyase (E.C. 4.2.2.2), and combinations thereof.

7. The method of claim 5, wherein the further fiber-degrading enzyme is selected from the group consisting of a cellobiohydrolase (E.C. 3.2.1.176 and E.C. 3.2.1.91), a β-glucosidase (E.C. 3.2.1.21), and combinations thereof.

8. The method of claim 1, further comprising administering at least one vitamin and/or at least one mineral to the subject.

* * * * *

SEQUENCE LISTING

<160> NUMBER OF SEQ ID NOS: 20

<210> SEQ ID NO 1
<211> LENGTH: 328
<212> TYPE: PRT
<213> ORGANISM: Artificial Sequence
<220> FEATURE:
<223> OTHER INFORMATION: Xylanase sequence

<400> SEQUENCE: 1

```
Met Lys Leu Ser Ser Phe Leu Tyr Thr Ala Ser Leu Val Ala Ala Ile
1               5                   10                  15

Pro Thr Ala Ile Glu Pro Arg Gln Ala Ala Asp Ser Ile Asn Lys Leu
            20                  25                  30

Ile Lys Asn Lys Gly Lys Leu Tyr Tyr Gly Thr Ile Thr Asp Pro Asn
        35                  40                  45

Leu Leu Gly Val Ala Lys Asp Thr Ala Ile Ile Lys Ala Asp Phe Gly
50                  55                  60

Ala Val Thr Pro Glu Asn Ser Gly Lys Trp Asp Ala Thr Glu Pro Ser
65                  70                  75                  80

Gln Gly Lys Phe Asn Phe Gly Ser Phe Asp Gln Val Val Asn Phe Ala
            85                  90                  95

Gln Gln Asn Gly Leu Lys Val Arg Gly His Thr Leu Val Trp His Ser
            100                 105                 110

Gln Leu Pro Gln Trp Val Lys Asn Ile Asn Asp Lys Ala Thr Leu Thr
            115                 120                 125

Lys Val Ile Glu Asn His Val Thr Gln Val Val Gly Arg Tyr Lys Gly
        130                 135                 140

Lys Ile Tyr Ala Trp Asp Val Val Asn Glu Ile Phe Glu Trp Asp Gly
145                 150                 155                 160

Thr Leu Arg Lys Asp Ser His Phe Asn Asn Val Phe Gly Asn Asp Asp
            165                 170                 175

Tyr Val Gly Ile Ala Phe Arg Ala Ala Arg Lys Ala Asp Pro Asn Ala
            180                 185                 190

Lys Leu Tyr Ile Asn Asp Tyr Ser Leu Asp Ser Gly Ser Ala Ser Lys
            195                 200                 205

Val Thr Lys Gly Met Val Pro Ser Val Lys Lys Trp Leu Ser Gln Gly
        210                 215                 220

Val Pro Val Asp Gly Ile Gly Ser Gln Thr His Leu Asp Pro Gly Ala
225                 230                 235                 240

Ala Gly Gln Ile Gln Gly Ala Leu Thr Ala Leu Ala Asn Ser Gly Val
            245                 250                 255

Lys Glu Val Ala Ile Thr Glu Leu Asp Ile Arg Thr Ala Pro Ala Asn
            260                 265                 270

Asp Tyr Ala Thr Val Thr Lys Ala Cys Leu Asn Val Pro Lys Cys Ile
            275                 280                 285

Gly Ile Thr Val Trp Gly Val Ser Asp Lys Asn Ser Trp Arg Lys Glu
            290                 295                 300

His Asp Ser Leu Leu Phe Asp Ala Asn Tyr Asn Pro Lys Pro Ala Tyr
305                 310                 315                 320

Thr Ala Val Val Asn Ala Leu Arg
                325

<210> SEQ ID NO 2
<211> LENGTH: 313
<212> TYPE: PRT
<213> ORGANISM: Artificial Sequence
<220> FEATURE:
<223> OTHER INFORMATION: Xylanase sequence

<400> SEQUENCE: 2

Ile Pro Thr Ala Ile Glu Pro Arg Gln Ala Ala Asp Ser Ile Asn Lys
1               5                   10                  15

Leu Ile Lys Asn Lys Gly Lys Leu Tyr Tyr Gly Thr Ile Thr Asp Pro
            20                  25                  30
```

```
Asn Leu Leu Gly Val Ala Lys Asp Thr Ala Ile Ile Lys Ala Asp Phe
             35                  40                  45

Gly Ala Val Thr Pro Glu Asn Ser Gly Lys Trp Asp Ala Thr Glu Pro
 50                  55                  60

Ser Gln Gly Lys Phe Asn Phe Gly Ser Phe Asp Gln Val Val Asn Phe
 65                  70                  75                  80

Ala Gln Gln Asn Gly Leu Lys Val Arg Gly His Thr Leu Val Trp His
                 85                  90                  95

Ser Gln Leu Pro Gln Trp Val Lys Asn Ile Asn Asp Lys Ala Thr Leu
            100                 105                 110

Thr Lys Val Ile Glu Asn His Val Thr Gln Val Val Gly Arg Tyr Lys
            115                 120                 125

Gly Lys Ile Tyr Ala Trp Asp Val Val Asn Glu Ile Phe Glu Trp Asp
        130                 135                 140

Gly Thr Leu Arg Lys Asp Ser His Phe Asn Asn Val Phe Gly Asn Asp
145                 150                 155                 160

Asp Tyr Val Gly Ile Ala Phe Arg Ala Ala Arg Lys Ala Asp Pro Asn
                165                 170                 175

Ala Lys Leu Tyr Ile Asn Asp Tyr Ser Leu Asp Ser Gly Ser Ala Ser
            180                 185                 190

Lys Val Thr Lys Gly Met Val Pro Ser Val Lys Lys Trp Leu Ser Gln
        195                 200                 205

Gly Val Pro Val Asp Gly Ile Gly Ser Gln Thr His Leu Asp Pro Gly
        210                 215                 220

Ala Ala Gly Gln Ile Gln Gly Ala Leu Thr Ala Leu Ala Asn Ser Gly
225                 230                 235                 240

Val Lys Glu Val Ala Ile Thr Glu Leu Asp Ile Arg Thr Ala Pro Ala
                245                 250                 255

Asn Asp Tyr Ala Thr Val Thr Lys Ala Cys Leu Asn Val Pro Lys Cys
            260                 265                 270

Ile Gly Ile Thr Val Trp Gly Val Ser Asp Lys Asn Ser Trp Arg Lys
        275                 280                 285

Glu His Asp Ser Leu Leu Phe Asp Ala Asn Tyr Asn Pro Lys Pro Ala
        290                 295                 300

Tyr Thr Ala Val Val Asn Ala Leu Arg
305                 310

<210> SEQ ID NO 3
<211> LENGTH: 305
<212> TYPE: PRT
<213> ORGANISM: Trichoderma reesei

<400> SEQUENCE: 3

Gln Ala Ala Asp Ser Ile Asn Lys Leu Ile Lys Asn Lys Gly Lys Leu
 1               5                  10                  15

Tyr Tyr Gly Thr Ile Thr Asp Pro Asn Leu Leu Gly Val Ala Lys Asp
                 20                  25                  30

Thr Ala Ile Ile Lys Ala Asp Phe Gly Ala Val Thr Pro Glu Asn Ser
             35                  40                  45

Gly Lys Trp Asp Ala Thr Glu Pro Ser Gln Gly Lys Phe Asn Phe Gly
 50                  55                  60

Ser Phe Asp Gln Val Val Asn Phe Ala Gln Gln Asn Gly Leu Lys Val
 65                  70                  75                  80

Arg Gly His Thr Leu Val Trp His Ser Gln Leu Pro Gln Trp Val Lys
                 85                  90                  95
```

Asn Ile Asn Asp Lys Ala Thr Leu Thr Lys Val Ile Glu Asn His Val
            100                 105                 110

Thr Gln Val Val Gly Arg Tyr Lys Gly Lys Ile Tyr Ala Trp Asp Val
        115                 120                 125

Val Asn Glu Ile Phe Glu Trp Asp Gly Thr Leu Arg Lys Asp Ser His
130                 135                 140

Phe Asn Asn Val Phe Gly Asn Asp Tyr Val Gly Ile Ala Phe Arg
145                 150                 155                 160

Ala Ala Arg Lys Ala Asp Pro Asn Ala Lys Leu Tyr Ile Asn Asp Tyr
                165                 170                 175

Ser Leu Asp Ser Gly Ser Ala Ser Lys Val Thr Lys Gly Met Val Pro
            180                 185                 190

Ser Val Lys Lys Trp Leu Ser Gln Gly Val Pro Val Asp Gly Ile Gly
        195                 200                 205

Ser Gln Thr His Leu Asp Pro Gly Ala Ala Gly Gln Ile Gln Gly Ala
210                 215                 220

Leu Thr Ala Leu Ala Asn Ser Gly Val Lys Glu Val Ala Ile Thr Glu
225                 230                 235                 240

Leu Asp Ile Arg Thr Ala Pro Ala Asn Asp Tyr Ala Thr Val Thr Lys
                245                 250                 255

Ala Cys Leu Asn Val Pro Lys Cys Ile Gly Ile Thr Val Trp Gly Val
            260                 265                 270

Ser Asp Lys Asn Ser Trp Arg Lys Glu His Asp Ser Leu Leu Phe Asp
        275                 280                 285

Ala Asn Tyr Asn Pro Lys Pro Ala Tyr Thr Ala Val Val Asn Ala Leu
290                 295                 300

Arg
305

<210> SEQ ID NO 4
<211> LENGTH: 328
<212> TYPE: PRT
<213> ORGANISM: Artificial Sequence
<220> FEATURE:
<223> OTHER INFORMATION: Xylanase sequence

<400> SEQUENCE: 4

Met Lys Leu Ser Ser Phe Leu Tyr Thr Ala Ser Leu Val Ala Ala Ile
1               5                   10                  15

Pro Thr Ala Ile Glu Pro Arg Gln Ala Ser Asp Ser Ile Asn Lys Leu
            20                  25                  30

Ile Lys Asn Lys Gly Lys Leu Tyr Tyr Gly Thr Ile Thr Asp Pro Asn
        35                  40                  45

Leu Leu Gly Val Ala Lys Asp Thr Ala Ile Ile Lys Ala Asp Phe Gly
    50                  55                  60

Ala Val Thr Pro Glu Asn Ser Gly Lys Trp Asp Ala Thr Glu Pro Ser
65                  70                  75                  80

Gln Gly Lys Phe Asn Phe Gly Ser Phe Asp Gln Val Val Asn Phe Ala
                85                  90                  95

Gln Gln Asn Gly Leu Lys Val Arg Gly His Thr Leu Val Trp His Ser
            100                 105                 110

Gln Leu Pro Gln Trp Val Lys Asn Ile Asn Asp Lys Ala Thr Leu Thr
        115                 120                 125

Lys Val Ile Glu Asn His Val Thr Asn Val Val Gly Arg Tyr Lys Gly
    130                 135                 140

```
Lys Ile Tyr Ala Trp Asp Val Val Asn Glu Ile Phe Asp Trp Asp Gly
145                 150                 155                 160

Thr Leu Arg Lys Asp Ser His Phe Asn Asn Val Phe Gly Asn Asp Asp
            165                 170                 175

Tyr Val Gly Ile Ala Phe Arg Ala Ala Arg Lys Ala Asp Pro Asn Ala
            180                 185                 190

Lys Leu Tyr Ile Asn Asp Tyr Ser Leu Asp Ser Gly Ser Ala Ser Lys
            195                 200                 205

Val Thr Lys Gly Met Val Pro Ser Val Lys Lys Trp Leu Ser Gln Gly
210                 215                 220

Val Pro Val Asp Gly Ile Gly Ser Gln Thr His Leu Asp Pro Gly Ala
225                 230                 235                 240

Ala Gly Gln Ile Gln Gly Ala Leu Thr Ala Leu Ala Asn Ser Gly Val
            245                 250                 255

Lys Glu Val Ala Ile Thr Glu Leu Asp Ile Arg Thr Ala Pro Ala Asn
            260                 265                 270

Asp Tyr Ala Thr Val Thr Lys Ala Cys Leu Asn Val Pro Lys Cys Ile
            275                 280                 285

Gly Ile Thr Val Trp Gly Val Ser Asp Lys Asn Ser Trp Arg Lys Glu
            290                 295                 300

His Asp Ser Leu Leu Phe Asp Ala Asn Tyr Asn Pro Lys Ala Ala Tyr
305                 310                 315                 320

Thr Ala Val Val Asn Ala Leu Arg
                325

<210> SEQ ID NO 5
<211> LENGTH: 313
<212> TYPE: PRT
<213> ORGANISM: Artificial Sequence
<220> FEATURE:
<223> OTHER INFORMATION: Xylanase sequence

<400> SEQUENCE: 5

Ile Pro Thr Ala Ile Glu Pro Arg Gln Ala Ser Asp Ser Ile Asn Lys
1               5                   10                  15

Leu Ile Lys Asn Lys Gly Lys Leu Tyr Tyr Gly Thr Ile Thr Asp Pro
            20                  25                  30

Asn Leu Leu Gly Val Ala Lys Asp Thr Ala Ile Ile Lys Ala Asp Phe
            35                  40                  45

Gly Ala Val Thr Pro Glu Asn Ser Gly Lys Trp Asp Ala Thr Glu Pro
50                  55                  60

Ser Gln Gly Lys Phe Asn Phe Gly Ser Phe Asp Gln Val Val Asn Phe
65                  70                  75                  80

Ala Gln Gln Asn Gly Leu Lys Val Arg Gly His Thr Leu Val Trp His
            85                  90                  95

Ser Gln Leu Pro Gln Trp Val Lys Asn Ile Asn Asp Lys Ala Thr Leu
            100                 105                 110

Thr Lys Val Ile Glu Asn His Val Thr Asn Val Val Gly Arg Tyr Lys
            115                 120                 125

Gly Lys Ile Tyr Ala Trp Asp Val Val Asn Glu Ile Phe Asp Trp Asp
            130                 135                 140

Gly Thr Leu Arg Lys Asp Ser His Phe Asn Asn Val Phe Gly Asn Asp
145                 150                 155                 160

Asp Tyr Val Gly Ile Ala Phe Arg Ala Ala Arg Lys Ala Asp Pro Asn
                165                 170                 175
```

Ala Lys Leu Tyr Ile Asn Asp Tyr Ser Leu Asp Ser Gly Ser Ala Ser
                180                 185                 190

Lys Val Thr Lys Gly Met Val Pro Ser Val Lys Lys Trp Leu Ser Gln
            195                 200                 205

Gly Val Pro Val Asp Gly Ile Gly Ser Gln Thr His Leu Asp Pro Gly
210                 215                 220

Ala Ala Gly Gln Ile Gln Gly Ala Leu Thr Ala Leu Ala Asn Ser Gly
225                 230                 235                 240

Val Lys Glu Val Ala Ile Thr Glu Leu Asp Ile Arg Thr Ala Pro Ala
                245                 250                 255

Asn Asp Tyr Ala Thr Val Thr Lys Ala Cys Leu Asn Val Pro Lys Cys
            260                 265                 270

Ile Gly Ile Thr Val Trp Gly Val Ser Asp Lys Asn Ser Trp Arg Lys
            275                 280                 285

Glu His Asp Ser Leu Leu Phe Asp Ala Asn Tyr Asn Pro Lys Ala Ala
        290                 295                 300

Tyr Thr Ala Val Val Asn Ala Leu Arg
305                 310

<210> SEQ ID NO 6
<211> LENGTH: 305
<212> TYPE: PRT
<213> ORGANISM: Artificial Sequence
<220> FEATURE:
<223> OTHER INFORMATION: Xylanase sequence

<400> SEQUENCE: 6

Gln Ala Ser Asp Ser Ile Asn Lys Leu Ile Lys Asn Lys Gly Lys Leu
1               5                   10                  15

Tyr Tyr Gly Thr Ile Thr Asp Pro Asn Leu Leu Gly Val Ala Lys Asp
                20                  25                  30

Thr Ala Ile Ile Lys Ala Asp Phe Gly Ala Val Thr Pro Glu Asn Ser
            35                  40                  45

Gly Lys Trp Asp Ala Thr Glu Pro Ser Gln Gly Lys Phe Asn Phe Gly
        50                  55                  60

Ser Phe Asp Gln Val Val Asn Phe Ala Gln Gln Asn Gly Leu Lys Val
65                  70                  75                  80

Arg Gly His Thr Leu Val Trp His Ser Gln Leu Pro Gln Trp Val Lys
                85                  90                  95

Asn Ile Asn Asp Lys Ala Thr Leu Thr Lys Val Ile Glu Asn His Val
            100                 105                 110

Thr Asn Val Val Gly Arg Tyr Lys Gly Lys Ile Tyr Ala Trp Asp Val
        115                 120                 125

Val Asn Glu Ile Phe Asp Trp Asp Gly Thr Leu Arg Lys Asp Ser His
    130                 135                 140

Phe Asn Asn Val Phe Gly Asn Asp Asp Tyr Val Gly Ile Ala Phe Arg
145                 150                 155                 160

Ala Ala Arg Lys Ala Asp Pro Asn Ala Lys Leu Tyr Ile Asn Asp Tyr
                165                 170                 175

Ser Leu Asp Ser Gly Ser Ala Ser Lys Val Thr Lys Gly Met Val Pro
            180                 185                 190

Ser Val Lys Lys Trp Leu Ser Gln Gly Val Pro Val Asp Gly Ile Gly
        195                 200                 205

Ser Gln Thr His Leu Asp Pro Gly Ala Ala Gly Gln Ile Gln Gly Ala
    210                 215                 220

Leu Thr Ala Leu Ala Asn Ser Gly Val Lys Glu Val Ala Ile Thr Glu
225                 230                 235                 240

Leu Asp Ile Arg Thr Ala Pro Ala Asn Asp Tyr Ala Thr Val Thr Lys
            245                 250                 255

Ala Cys Leu Asn Val Pro Lys Cys Ile Gly Ile Thr Val Trp Gly Val
        260                 265                 270

Ser Asp Lys Asn Ser Trp Arg Lys Glu His Asp Ser Leu Leu Phe Asp
    275                 280                 285

Ala Asn Tyr Asn Pro Lys Ala Ala Tyr Thr Ala Val Val Asn Ala Leu
290                 295                 300

Arg
305

<210> SEQ ID NO 7
<211> LENGTH: 229
<212> TYPE: PRT
<213> ORGANISM: Artificial Sequence
<220> FEATURE:
<223> OTHER INFORMATION: Xylanase sequence

<400> SEQUENCE: 7

Met Val Ser Phe Lys Tyr Leu Phe Leu Ala Ala Ser Ala Leu Gly Ala
1               5                   10                  15

Leu Ala Ala Pro Val Glu Val Glu Glu Ser Ser Trp Phe Asn Glu Thr
            20                  25                  30

Ala Leu His Glu Phe Ala Glu Arg Ala Gly Thr Pro Ser Ser Thr Gly
        35                  40                  45

Trp Asn Asn Gly Tyr Tyr Tyr Ser Phe Trp Thr Asp Asn Gly Gly Thr
    50                  55                  60

Val Asn Tyr Gln Asn Gly Asn Gly Gly Ser Tyr Ser Val Gln Trp Lys
65                  70                  75                  80

Asp Thr Gly Asn Phe Val Gly Gly Lys Gly Trp Asn Pro Gly Ser Ala
                85                  90                  95

Arg Thr Ile Asn Tyr Ser Gly Ser Phe Asn Pro Ser Gly Asn Ala Tyr
            100                 105                 110

Leu Thr Val Tyr Gly Trp Thr Thr Asn Pro Leu Val Glu Tyr Tyr Ile
        115                 120                 125

Val Glu Asn Tyr Gly Thr Tyr Asn Pro Gly Asn Gly Gly Thr Tyr Arg
    130                 135                 140

Gly Ser Val Tyr Ser Asp Gly Ala Asn Tyr Asn Ile Tyr Thr Ala Thr
145                 150                 155                 160

Arg Tyr Asn Ala Pro Ser Ile Glu Gly Asp Lys Thr Phe Thr Gln Tyr
                165                 170                 175

Trp Ser Val Arg Gln Ser Lys Arg Thr Gly Gly Thr Val Thr Thr Ala
            180                 185                 190

Asn His Phe Asn Ala Trp Ala Gln Leu Gly Met Ser Leu Gly Thr His
        195                 200                 205

Asn Tyr Gln Ile Val Ala Thr Glu Gly Tyr Gln Ser Ser Gly Ser Ser
    210                 215                 220

Ser Ile Thr Val Tyr
225

<210> SEQ ID NO 8
<211> LENGTH: 211
<212> TYPE: PRT
<213> ORGANISM: Artificial Sequence
<220> FEATURE:
<223> OTHER INFORMATION: Xylanase sequence

<400> SEQUENCE: 8

Ala Pro Val Glu Val Glu Ser Ser Trp Phe Asn Glu Thr Ala Leu
1               5                   10                  15

His Glu Phe Ala Glu Arg Ala Gly Thr Pro Ser Ser Thr Gly Trp Asn
            20                  25                  30

Asn Gly Tyr Tyr Tyr Ser Phe Trp Thr Asp Asn Gly Gly Thr Val Asn
        35                  40                  45

Tyr Gln Asn Gly Asn Gly Gly Ser Tyr Ser Val Gln Trp Lys Asp Thr
    50                  55                  60

Gly Asn Phe Val Gly Gly Lys Gly Trp Asn Pro Gly Ser Ala Arg Thr
65                  70                  75                  80

Ile Asn Tyr Ser Gly Ser Phe Asn Pro Ser Gly Asn Ala Tyr Leu Thr
                85                  90                  95

Val Tyr Gly Trp Thr Thr Asn Pro Leu Val Glu Tyr Tyr Ile Val Glu
            100                 105                 110

Asn Tyr Gly Thr Tyr Asn Pro Gly Asn Gly Gly Thr Tyr Arg Gly Ser
        115                 120                 125

Val Tyr Ser Asp Gly Ala Asn Tyr Asn Ile Tyr Thr Ala Thr Arg Tyr
    130                 135                 140

Asn Ala Pro Ser Ile Glu Gly Asp Lys Thr Phe Thr Gln Tyr Trp Ser
145                 150                 155                 160

Val Arg Gln Ser Lys Arg Thr Gly Gly Thr Val Thr Thr Ala Asn His
                165                 170                 175

Phe Asn Ala Trp Ala Gln Leu Gly Met Ser Leu Gly Thr His Asn Tyr
            180                 185                 190

Gln Ile Val Ala Thr Glu Gly Tyr Gln Ser Ser Gly Ser Ser Ser Ile
        195                 200                 205

Thr Val Tyr
    210

<210> SEQ ID NO 9
<211> LENGTH: 189
<212> TYPE: PRT
<213> ORGANISM: Artificial Sequence
<220> FEATURE:
<223> OTHER INFORMATION: Xylanase sequence

<400> SEQUENCE: 9

Ala Gly Thr Pro Ser Ser Thr Gly Trp Asn Asn Gly Tyr Tyr Tyr Ser
1               5                   10                  15

Phe Trp Thr Asp Asn Gly Gly Thr Val Asn Tyr Gln Asn Gly Asn Gly
            20                  25                  30

Gly Ser Tyr Ser Val Gln Trp Lys Asp Thr Gly Asn Phe Val Gly Gly
        35                  40                  45

Lys Gly Trp Asn Pro Gly Ser Ala Arg Thr Ile Asn Tyr Ser Gly Ser
    50                  55                  60

Phe Asn Pro Ser Gly Asn Ala Tyr Leu Thr Val Tyr Gly Trp Thr Thr
65                  70                  75                  80

Asn Pro Leu Val Glu Tyr Tyr Ile Val Glu Asn Tyr Gly Thr Tyr Asn
                85                  90                  95

Pro Gly Asn Gly Gly Thr Tyr Arg Gly Ser Val Tyr Ser Asp Gly Ala
            100                 105                 110

Asn Tyr Asn Ile Tyr Thr Ala Thr Arg Tyr Asn Ala Pro Ser Ile Glu

```
            115                 120                 125
Gly Asp Lys Thr Phe Thr Gln Tyr Trp Ser Val Arg Gln Ser Lys Arg
        130                 135                 140

Thr Gly Gly Thr Val Thr Thr Ala Asn His Phe Asn Ala Trp Ala Gln
145                 150                 155                 160

Leu Gly Met Ser Leu Gly Thr His Asn Tyr Gln Ile Val Ala Thr Glu
                165                 170                 175

Gly Tyr Gln Ser Ser Gly Ser Ser Ile Thr Val Tyr
            180                 185
```

<210> SEQ ID NO 10
<211> LENGTH: 232
<212> TYPE: PRT
<213> ORGANISM: Artificial Sequence
<220> FEATURE:
<223> OTHER INFORMATION: Xylanase sequence

<400> SEQUENCE: 10

```
Met Val Ser Phe Thr Ser Leu Leu Ala Ala Val Ser Ala Val Thr Gly
1               5                   10                  15

Val Met Ala Leu Pro Ser Ala Gln Pro Val Asp Gly Met Ser Val Val
            20                  25                  30

Glu Arg Asp Pro Pro Thr Asn Val Leu Asp Lys Arg Thr Gln Pro Thr
        35                  40                  45

Thr Gly Thr Ser Gly Gly Tyr Tyr Phe Ser Phe Trp Thr Asp Thr Pro
    50                  55                  60

Asn Ser Val Thr Tyr Thr Asn Gly Asn Gly Gly Gln Phe Ser Met Gln
65                  70                  75                  80

Trp Ser Gly Asn Gly Asn His Val Gly Gly Lys Gly Trp Met Pro Gly
                85                  90                  95

Thr Ser Arg Thr Ile Lys Tyr Ser Gly Ser Tyr Asn Pro Asn Gly Asn
            100                 105                 110

Ser Tyr Leu Ala Val Tyr Gly Trp Thr Arg Asn Pro Leu Ile Glu Tyr
        115                 120                 125

Tyr Ile Val Glu Asn Phe Gly Thr Tyr Asn Pro Ser Ser Gly Gly Gln
    130                 135                 140

Lys Lys Gly Glu Val Asn Val Asp Gly Ser Val Tyr Asp Ile Tyr Val
145                 150                 155                 160

Ser Thr Arg Val Asn Ala Pro Ser Ile Asp Gly Asn Lys Thr Phe Gln
                165                 170                 175

Gln Tyr Trp Ser Val Arg Arg Asn Lys Arg Ser Ser Gly Ser Val Asn
            180                 185                 190

Thr Gly Ala His Phe Gln Ala Trp Lys Asn Val Gly Leu Asn Leu Gly
        195                 200                 205

Thr His Asp Tyr Gln Ile Leu Ala Val Glu Gly Tyr Tyr Ser Ser Gly
    210                 215                 220

Ser Ala Ser Met Thr Val Ser Gln
225                 230
```

<210> SEQ ID NO 11
<211> LENGTH: 213
<212> TYPE: PRT
<213> ORGANISM: Artificial Sequence
<220> FEATURE:
<223> OTHER INFORMATION: Xylanase sequence

<400> SEQUENCE: 11

```
Leu Pro Ser Ala Gln Pro Val Asp Gly Met Ser Val Val Glu Arg Asp
1               5                   10                  15

Pro Pro Thr Asn Val Leu Asp Lys Arg Thr Gln Pro Thr Thr Gly Thr
            20                  25                  30

Ser Gly Gly Tyr Tyr Phe Ser Phe Trp Thr Asp Thr Pro Asn Ser Val
        35                  40                  45

Thr Tyr Thr Asn Gly Asn Gly Gly Gln Phe Ser Met Gln Trp Ser Gly
    50                  55                  60

Asn Gly Asn His Val Gly Lys Gly Trp Met Pro Gly Thr Ser Arg
65                  70                  75                  80

Thr Ile Lys Tyr Ser Gly Ser Tyr Asn Pro Asn Gly Asn Ser Tyr Leu
                85                  90                  95

Ala Val Tyr Gly Trp Thr Arg Asn Pro Leu Ile Glu Tyr Tyr Ile Val
            100                 105                 110

Glu Asn Phe Gly Thr Tyr Asn Pro Ser Ser Gly Gln Lys Lys Gly
            115                 120                 125

Glu Val Asn Val Asp Gly Ser Val Tyr Asp Ile Tyr Val Ser Thr Arg
    130                 135                 140

Val Asn Ala Pro Ser Ile Asp Gly Asn Lys Thr Phe Gln Gln Tyr Trp
145                 150                 155                 160

Ser Val Arg Arg Asn Lys Arg Ser Ser Gly Ser Val Asn Thr Gly Ala
                165                 170                 175

His Phe Gln Ala Trp Lys Asn Val Gly Leu Asn Leu Gly Thr His Asp
            180                 185                 190

Tyr Gln Ile Leu Ala Val Glu Gly Tyr Tyr Ser Ser Gly Ser Ala Ser
            195                 200                 205

Met Thr Val Ser Gln
            210

<210> SEQ ID NO 12
<211> LENGTH: 188
<212> TYPE: PRT
<213> ORGANISM: Artificial Sequence
<220> FEATURE:
<223> OTHER INFORMATION: Xylanase sequence

<400> SEQUENCE: 12

Thr Gln Pro Thr Thr Gly Thr Ser Gly Gly Tyr Tyr Phe Ser Phe Trp
1               5                   10                  15

Thr Asp Thr Pro Asn Ser Val Thr Tyr Thr Asn Gly Asn Gly Gly Gln
            20                  25                  30

Phe Ser Met Gln Trp Ser Gly Asn Gly Asn His Val Gly Lys Gly
        35                  40                  45

Trp Met Pro Gly Thr Ser Arg Thr Ile Lys Tyr Ser Gly Ser Tyr Asn
50                  55                  60

Pro Asn Gly Asn Ser Tyr Leu Ala Val Tyr Gly Trp Thr Arg Asn Pro
65                  70                  75                  80

Leu Ile Glu Tyr Tyr Ile Val Glu Asn Phe Gly Thr Tyr Asn Pro Ser
                85                  90                  95

Ser Gly Gly Gln Lys Lys Gly Glu Val Asn Val Asp Gly Ser Val Tyr
            100                 105                 110

Asp Ile Tyr Val Ser Thr Arg Val Asn Ala Pro Ser Ile Asp Gly Asn
        115                 120                 125

Lys Thr Phe Gln Gln Tyr Trp Ser Val Arg Arg Asn Lys Arg Ser Ser
    130                 135                 140
```

Gly Ser Val Asn Thr Gly Ala His Phe Gln Ala Trp Lys Asn Val Gly
145                 150                 155                 160

Leu Asn Leu Gly Thr His Asp Tyr Gln Ile Leu Ala Val Glu Gly Tyr
            165                 170                 175

Tyr Ser Ser Gly Ser Ala Ser Met Thr Val Ser Gln
            180                 185

<210> SEQ ID NO 13
<211> LENGTH: 19
<212> TYPE: DNA
<213> ORGANISM: Artificial Sequence
<220> FEATURE:
<223> OTHER INFORMATION: Primer 28F
<220> FEATURE:
<221> NAME/KEY: misc_feature
<222> LOCATION: (11)..(11)
<223> OTHER INFORMATION: n is a, c, g, or t

<400> SEQUENCE: 13
gagtttgatc ntggctcag                                              19

<210> SEQ ID NO 14
<211> LENGTH: 18
<212> TYPE: DNA
<213> ORGANISM: Artificial Sequence
<220> FEATURE:
<223> OTHER INFORMATION: Primer 519R
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 14
gtnttacngc ggckgctg                                               18

<210> SEQ ID NO 15
<211> LENGTH: 10
<212> TYPE: DNA
<213> ORGANISM: Artificial Sequence
<220> FEATURE:
<223> OTHER INFORMATION: Primer 1

<400> SEQUENCE: 15
ggtgcgggaa                                                        10

<210> SEQ ID NO 16
<211> LENGTH: 10
<212> TYPE: DNA
<213> ORGANISM: Artificial Sequence
<220> FEATURE:
<223> OTHER INFORMATION: Primer 2

<400> SEQUENCE: 16
gtttcgctcc                                                        10

<210> SEQ ID NO 17
<211> LENGTH: 10
<212> TYPE: DNA
<213> ORGANISM: Artificial Sequence
<220> FEATURE:
<223> OTHER INFORMATION: Primer 3

<400> SEQUENCE: 17

```
gtagacccgt                                                                10

<210> SEQ ID NO 18
<211> LENGTH: 10
<212> TYPE: DNA
<213> ORGANISM: Artificial Sequence
<220> FEATURE:
<223> OTHER INFORMATION: Primer 4

<400> SEQUENCE: 18
aagagcccgt                                                                10

<210> SEQ ID NO 19
<211> LENGTH: 10
<212> TYPE: DNA
<213> ORGANISM: Artificial Sequence
<220> FEATURE:
<223> OTHER INFORMATION: Primer 5

<400> SEQUENCE: 19
aacgcgcaac                                                                10

<210> SEQ ID NO 20
<211> LENGTH: 10
<212> TYPE: DNA
<213> ORGANISM: Artificial Sequence
<220> FEATURE:
<223> OTHER INFORMATION: Primer 6

<400> SEQUENCE: 20
cccgtcagca                                                                10
```